(12) United States Patent
Yukawa et al.

(10) Patent No.: US 9,090,900 B2
(45) Date of Patent: Jul. 28, 2015

(54) CORYNEFORM BACTERIUM TRANSFORMANT AND PROCESS FOR PRODUCING PHENOL USING THE SAME

(75) Inventors: Hideaki Yukawa, Kizugawa (JP); Masayuki Inui, Kizugawa (JP)

(73) Assignee: GREEN PHENOL DEVELOPMENT CO., LTD., Kyoto (JP)

( * ) Notice: Subject to any disclaimer, the term of this patent is extended or adjusted under 35 U.S.C. 154(b) by 0 days.

(21) Appl. No.: 13/884,536

(22) PCT Filed: Nov. 9, 2011

(86) PCT No.: PCT/JP2011/075825
§ 371 (c)(1),
(2), (4) Date: Jun. 28, 2013

(87) PCT Pub. No.: WO2012/063860
PCT Pub. Date: May 18, 2012

(65) Prior Publication Data
US 2013/0266999 A1    Oct. 10, 2013

(30) Foreign Application Priority Data
Nov. 10, 2010  (JP) ................... 2010-252264

(51) Int. Cl.
C12P 7/22        (2006.01)
C12N 1/20        (2006.01)
C12N 15/77       (2006.01)
C12N 9/88        (2006.01)

(52) U.S. Cl.
CPC  *C12N 15/77* (2013.01); *C12N 9/88* (2013.01); *C12P 7/22* (2013.01); *C12Y 401/01061* (2013.01)

(58) Field of Classification Search
CPC ............... C12P 7/24; C12P 7/22; C12N 9/88; C12N 15/77; C12Y 401/01061
USPC ............................................ 435/156, 252.32
See application file for complete search history.

(56) References Cited

U.S. PATENT DOCUMENTS

| | | | |
|---|---|---|---|
| 6,210,937 B1 * | 4/2001 | Ward et al. ................. | 435/146 |
| 7,368,268 B2 * | 5/2008 | Murakami et al. ........... | 435/145 |
| 2007/0087423 A1 | 4/2007 | Murakami et al. | |
| 2011/0117612 A1 | 5/2011 | Yukawa et al. | |

FOREIGN PATENT DOCUMENTS

| | | | | |
|---|---|---|---|---|
| JP | 2006-50914 | * | 2/2006 | ............ C12N 15/09 |
| JP | 2006-050914 A | | 2/2006 | |
| WO | WO-2005010182 A1 | | 2/2005 | |
| WO | WO-2009154122 A1 | | 12/2009 | |

OTHER PUBLICATIONS

Tsuyoshi Matsui et al., Purification, characterization, and gene cloning of 4-hydroxybenzoate decarboxylase of *Enterobacter cloacae* P240. Arch. Microbiol. 186: 21-29, 2006.*
Burgess et al, Possible Dissociation of the Heparin-binding and Mitogenic Activities of Heparin-binding (Acidic Fibroblast) Growth Factor-I from Its Receptor-binding Activities by Site-directed Mutagenesis of a Single Lysine Residue. Journal of Cell Biology vol. 111: 2129-2138, 1990.*
Lazar et al. Transforming Growth Factor ox: Mutation of Aspartic Acid 47 and Leucine 48 Results in Different Biological Activities Molecular and Cellular Biology. vol. 8 No. 3 1247-1252, 1988.*
Shen et al., Genomic Analysis and Identification of Catabolic Pathways for Aromatic Compounds in Coryllebacterium glutamicum. Microbes and Environments. vol. 20, No. 3, 160 167, 2005.*
Powlowski et al., Genetics and biochemistry of phenol degradation by *Pseudomonas* sp. CF600. Biodtgradalion 5: 219-236, 1994.*
Huang et al., Genetic and biochemical characterization of a 4-hydroxybenzoate hydroxylase from *Corynebacterium glutamicum*, Appl Microbiol Biotechnol, vol. 78, pp. 75-83 (2008).
Ho et al., "Biodegradation of phenol using *Corynebacterium* sp. DJ1 aerobic granules," Bioresource Technology, vol. 100, pp. 5051-5055 (2009).
Zhang et al., "Reversible Conversion of 4-Hydroxybenzoate and Phenol by *Clostridium hydroxybenzoicum*," Applied and Environmental Microbiology, pp. 4182-4185 (1994).
Extended European Search Report for PCT/JP2011/075825 dated Apr. 10, 2014.
International Preliminary Report on Patentability in corresponding PCT/JP2011/075825 dated May 14, 2013. (English Translation).
Matsui et al., "Purification, characterization, and gene cloning of 4-hydroxybenzoate decarboxylase of *Enterobacter cloacae* P240," Arch Microbiol, 186: 21-29 (2006).
Breitenstein et al., "Reclassification of *Clostridium hydroxybenzoicum* as *Sedimentibacter hydroxybenzoicus* gen. nov., comb. nov., and description of *Sedimentibacter saalensis* sp. nov.," International Journal of Systematic and Evolutionary Microbiology, 52: 801-807 (2002).
International Search Report for PCT/JP2011/075825 dated Dec. 6, 2011.
Written Opinion for PCT/JP2011/075825 dated Dec. 6, 2011. (no translation).
Eppink et al., "Purification and Properties of 4-Hydroxybenzoate 1-Hydroxylase (Decarboxylating), a Novel Flavin Adenine Dinucleotide-Dependent Monooxygenase from *Candida parapsilosis* CBS604," Journal of Bacteriology, pp. 6680-6687 (1997).

* cited by examiner

*Primary Examiner* — Ganapathirama Raghu

(57) ABSTRACT

Provided is a phenol-producing transformant constructed by transferring a gene which encodes an enzyme having 4-hydroxybenzoate decarboxylase activity into *Corynebacterium glutamicum* as a host. Also provided is a process for producing phenol, which comprises a step of allowing the transformant to react in a reaction mixture containing 4-hydroxybenzoate or a salt thereof under reducing conditions, and a step of collecting phenol from the reaction mixture.

10 Claims, 1 Drawing Sheet

SEQUENCE LISTING

<160> NUMBER OF SEQ ID NOS: 59

<210> SEQ ID NO 1
<211> LENGTH: 1195
<212> TYPE: DNA
<213> ORGANISM: Corynebacterium casei

<400> SEQUENCE: 1

```
atgaaaaccg accgtgcacg ctcgtgtgag aaagtcagct acatgagacc aactacccgc        60
cctgagggac gctttgagca gctgtggctg ccgctgtggc cattggcaag cgatgacctc       120
cgtgagggca tttaccgcac ctcacggaag aacgcgctgg ataagcgcta cgtcgaagcc       180
aatcccgacg cgctctctaa cctcctggtc gttgacatcg accaggagga cgcgcttttg       240
cgctctttgt gggacaggga ggactggaga cctaacgcgg tggttgaaaa cccccttaaac      300 gggcacgcac acgctgtctg ggcgctcgcg gagccattta cccgcaccga atacgccaaa       360
cgcaagcctt tggcctatgc cgcggctgtc accgaaggcc tacggcgctc tgtcgatggc       420
gatagcggat actccgggct gatcaccaaa aacccccgagc acactgcatg ggatagtcac       480
tggatcaccg ataagctgta tacgctcgat gagctgcgct tttggctcga agaaaccggc       540
tttatgccgc ctgcgtcctg gaggaaaacg cggcggttct cgccagttgg tctaggtcgt       600
aattgcgcac tcttttgaaag cgcacgtacg tgggcatatc gggaggtcag aaagcatttt       660
ggagacgctg acggcctagg ccgcgcaatc caaaccaccg cgcaagcact taaccaagag       720
ctgtttgatg aaccactacc tgtggccgaa gttgactgta ttgccaggtc aatccataaa       780
tggatcatca ccaagtcacg catgtggaca gacgcgccg ccgtctacga cgccacattc       840
accgcaatgc aatccgcacg cgggaagaaa ggctggcaac gaagcgctga ggtgcgtcgt       900
gaggctggac atactctttg gaggaacatt ggctaaggtt tatgcacgtt atccacgcaa       960
cggaaaaaca gcccgcgagc tggcagaacg tgccggtatg tcggtgagaa cagctcaacg      1020
atggacttcc gaaccgcgtg aagtgttcat taaacgtgcc aacgagaagc gtgctcgcgt      1080
ccaggagctg cgcgccaaag gtctgtccat gcgcgctatc gcggcagaga ttggttgctc      1140
ggtgggcacg gttcaccgct acgtcaaaga agttgaagag aagaaaaccg cgtaa          1195
```

<210> SEQ ID NO 2
<211> LENGTH: 2675
<212> TYPE: DNA
<213> ORGANISM: Unknown
<220> FEATURE:
<223> OTHER INFORMATION: pHSG298

<400> SEQUENCE: 2

| | | | | | |
|---|---|---|---|---|---|
| gaggtctgcc | tcgtgaagaa | ggtgttgctg | actcatacca | ggcctgaatc | gccccatcat | 60 |
| ccagccagaa | agtgagggag | ccacggttga | tgagagcttt | gttgtaggtg | gaccagttgg | 120 |
| tgattttgaa | cttttgcttt | gccacggaac | ggtctgcgtt | gtcgggaaga | tgcgtgatct | 180 |
| gatccttcaa | ctcagcaaaa | gttcgattta | ttcaacaaag | ccacgttgtg | tctcaaaatc | 240 |
| tctgatgtta | cattgcacaa | gataaaaata | tatcatcatg | aacaataaaa | ctgtctgctt | 300 |
| acataaacag | taatacaagg | ggtgttatga | gccatattca | acgggaaacg | tcttgctcga | 360 |
| agccgcgatt | aaattccaac | atggatgctg | atttatatgg | gtataaatgg | gctcgcgata | 420 |
| atgtcgggca | atcaggtgcg | acaatctatc | gattgtatgg | gaagcccgat | gcgccagagt | 480 |
| tgtttctgaa | acatggcaaa | ggtagcgttg | ccaatgatgt | tacagatgag | atggtcagac | 540 |
| taaactggct | gacggaattt | atgcctcttc | cgaccatcaa | gcattttatc | cgtactcctg | 600 |
| atgatgcatg | gttactcacc | actgcgatcc | ccgggaaaac | agcattccag | gtattagaag | 660 |
| aatatcctga | ttcaggtgaa | aatattgttg | atgcgctggc | agtgttcctg | cgccggttgc | 720 |
| attcgattcc | tgtttgtaat | tgtcctttta | acagcgatcg | cgtatttcgt | ctcgctcagg | 780 |
| cgcaatcacg | aatgaataac | ggtttggttg | atgcgagtga | ttttgatgac | gagcgtaatg | 840 |
| gctggcctgt | tgaacaagtc | tggaaagaaa | tgcataagct | tttgccattc | tcaccggatt | 900 |
| cagtcgtcac | tcatggtgat | ttctcacttg | ataaccttat | ttttgacgag | gggaaattaa | 960 |
| taggttgtat | tgatgttgga | cgagtcggaa | tcgcagaccg | ataccaggat | cttgccatcc | 1020 |
| tatggaactg | cctcggtgag | ttttctcctt | cattacagaa | acggcttttt | caaaaatatg | 1080 |
| gtattgataa | tcctgatatg | aataaattgc | agtttcattt | gatgctcgat | gagtttttct | 1140 |
| aatcagaatt | ggttaattgg | ttgtaacact | ggcagagcat | tacgctgact | tgacgggacg | 1200 |
| gcggctttgt | tgaataaatc | gcattcgcca | ttcaggctgc | gcaactgttg | ggaagggcga | 1260 |
| tcggtgcggg | cctcttcgct | attacgccag | ctggcgaaag | gggatgtgc | tgcaaggcga | 1320 |
| ttaagttggg | taacgccagg | gttttcccag | tcacgacgtt | gtaaaacgac | ggccagtgcc | 1380 |
| aagcttgcat | gcctgcaggt | cgactctaga | ggatccccgg | gtaccgagct | cgaattcgta | 1440 |
| atcatgtcat | agctgtttcc | tgtgtgaaat | tgttatccgc | tcacaattcc | acacaacata | 1500 |
| cgagccggaa | gcataaagtg | taaagcctgg | ggtgcctaat | gagtgagcta | actcacatta | 1560 |
| attgcgttgc | gctcactgcc | cgctttccag | tcgggaaacc | tgtcgtgcca | gctgcattaa | 1620 |
| tgaatcggcc | aacgcgcggg | gagaggcggt | ttgcgtattg | gcgaactttt | gctgagttga | 1680 |
| aggatcagat | cacgcatctt | cccgacaacg | cagaccgttc | cgtggcaaag | caaaagttca | 1740 |
| aaatcagtaa | ccgtcagtgc | cgataagttc | aaagttaaac | ctggtgttga | taccaacatt | 1800 |
| gaaacgctga | tcgaaaacgc | gctgaaaaac | gctgctgaat | gtgcgagctt | cttccgcttc | 1860 |
| ctcgctcact | gactcgctgc | gctcggtcgt | tcggctgcgg | cgagcggtat | cagctcactc | 1920 |
| aaaggcggta | atacggttat | ccacagaatc | aggggataac | gcaggaaaga | acatgtgagc | 1980 |
| aaaaggccag | caaaaggcca | ggaaccgtaa | aaaggccgcg | ttgctggcgt | ttttccatag | 2040 |
| gctccgcccc | cctgacgagc | atcacaaaaa | tcgacgctca | agtcagaggt | ggcgaaaccc | 2100 |

-continued

```
gacaggacta taaagatacc aggcgtttcc ccctggaagc tccctcgtgc gctctcctgt    2160
tccgaccctg ccgcttaccg gatacctgtc cgcctttctc ccttcgggaa gcgtggcgct    2220
ttctcaatgc tcacgctgta ggtatctcag ttcggtgtag gtcgttcgct ccaagctggg    2280
ctgtgtgcac gaaccccccg ttcagcccga ccgctgcgcc ttatccggta actatcgtct    2340
tgagtccaac ccggtaagac acgacttatc gccactggca gcagccactg gtaacaggat    2400
tagcagagcg aggtatgtag gcggtgctac agagttcttg aagtggtggc ctaactacgg    2460
ctacactaga aggacagtat ttggtatctg cgctctgctg aagccagtta ccttcggaaa    2520
aagagttggt agctcttgat ccggcaaaca accaccgct ggtagcggtg gttttttgt      2580 ttgcaagcag cagattacgc gcagaaaaaa aggatctcaa gaagatcctt tgatcttttc    2640
tacggggtct gacgctcagt ggaacgatcc gtcga                                2675
```

```
<210> SEQ ID NO 3
<211> LENGTH: 25
<212> TYPE: DNA
<213> ORGANISM: Artificial sequence
<220> FEATURE:
<223> OTHER INFORMATION: PCR primer

<400> SEQUENCE: 3
atagatctag aacgtccgta ggagc                                            25

<210> SEQ ID NO 4
<211> LENGTH: 26
<212> TYPE: DNA
<213> ORGANISM: Artificial sequence
<220> FEATURE:
<223> OTHER INFORMATION: PCR primer

<400> SEQUENCE: 4
atagatctga cttggttacg atggac                                           26

<210> SEQ ID NO 5
<211> LENGTH: 27
<212> TYPE: DNA
<213> ORGANISM: Artificial sequence
<220> FEATURE:
<223> OTHER INFORMATION: PCR primer

<400> SEQUENCE: 5
atagatctag gtttccgac tggaaag                                           27

<210> SEQ ID NO 6
<211> LENGTH: 28
<212> TYPE: DNA
<213> ORGANISM: Artificial sequence
<220> FEATURE:
<223> OTHER INFORMATION: PCR primer

<400> SEQUENCE: 6
atagatctcg tgccagctgc attaatga                                         28

<210> SEQ ID NO 7
<211> LENGTH: 551
<212> TYPE: DNA
<213> ORGANISM: Corynebacterium glutamicum

<400> SEQUENCE: 7
ccgaagatct gaagattcct gatacaaatt ctgttgtgac ggaagatttg ttggaagaaa     60
```

| | |
|---|---|
| tctagtcgct cgtctcataa aaacgaccga gcctattggg attaccattg aagccagtgt | 120 |
| gagttgcatc acactggctt caaatctgag actttacttt gtggattcac ggggtgtag | 180 |
| tgcaattcat aattagcccc attcggggga gcagatcgcg gcgcgaacga tttcaggttc | 240 |
| gttccctgca aaactatttt agcgcaagtg ttggaaatgc cccgtctgg ggtcaatgtc | 300 |
| tattttgaa tgtgtttgta tgattttgaa tccgctgcaa aatctttgtt tccccgctaa | 360 |
| agttggggac aggttgacac ggagttgact cgacgaatta ccaatgtga gtaggtttgg | 420 |
| tgcgtgagtt ggaaaatttc gccatactcg cccttgggtt ctgtcagctc aagaattctt | 480 |
| gagtgaccga tgctctgatt gacctaactg cttgacacat tgcatttcct acaatcttta | 540 |
| gaggagacac a | 551 |

<210> SEQ ID NO 8
<211> LENGTH: 425
<212> TYPE: DNA
<213> ORGANISM: Unkown
<220> FEATURE:
<223> OTHER INFORMATION: rrnBT1T2 terminator

<400> SEQUENCE: 8

| | |
|---|---|
| ctgttttggc ggatgagaga agattttcag cctgatacag attaaatcag aacgcagaag | 60 |
| cggtctgata aaacagaatt tgcctggcgg cagtagcgcg gtggtcccac ctgaccccat | 120 |
| gccgaactca gaagtgaaac gccgtagcgc cgatggtagt gtggggtctc ccatgcgag | 180 |
| agtagggaac tgccaggcat caaataaaac gaaaggctca gtcgaaagac tgggcctttc | 240 |
| gttttatctg ttgtttgtcg gtgaacgctc tcctgagtag acaaatccg ccgggagcgg | 300 |
| atttgaacgt tgcgaagcaa cggcccggag ggtggcgggc aggacgcccg ccataaactg | 360 |
| ccaggcatca aattaagcag aaggccatcc tgacggatgg ccttttgcg tttctacaaa | 420 |
| ctctt | 425 |

<210> SEQ ID NO 9
<211> LENGTH: 31
<212> TYPE: DNA
<213> ORGANISM: Artificial sequence
<220> FEATURE:
<223> OTHER INFORMATION: PCR primer

<400> SEQUENCE: 9

| | |
|---|---|
| ctctgtcgac ccgaagatct gaagattcct g | 31 |

<210> SEQ ID NO 10
<211> LENGTH: 46
<212> TYPE: DNA
<213> ORGANISM: Artificial sequence
<220> FEATURE:
<223> OTHER INFORMATION: PCR primer

<400> SEQUENCE: 10

| | |
|---|---|
| ctctgtcgac ggatccccat ggtgtgtctc ctctaaagat tgtagg | 46 |

<210> SEQ ID NO 11
<211> LENGTH: 36
<212> TYPE: DNA
<213> ORGANISM: Artificial sequence
<220> FEATURE:
<223> OTHER INFORMATION: PCR primer

<400> SEQUENCE: 11

| | |
|---|---|
| ctctgcatgc ccatggctgt tttggcggat gagaga | 36 |

<210> SEQ ID NO 12
<211> LENGTH: 41
<212> TYPE: DNA
<213> ORGANISM: Artificial sequence
<220> FEATURE:
<223> OTHER INFORMATION: PCR primer

<400> SEQUENCE: 12

```
ctctgcatgc tcatgaaaga gtttgtagaa acgcaaaaag g                 41
```

<210> SEQ ID NO 13
<211> LENGTH: 5118
<212> TYPE: DNA
<213> ORGANISM: Corynebacterium glutamicum

<400> SEQUENCE: 13

```
agatctaggt tcccgactg  gaaagcgggc agtgagcgca acgcaattaa tgtgagttag    60
ctcactcatt aggcacccca ggctttacac tttatgcttc cggctcgtat gttgtgtgga   120
attgtgagcg gataacaatt tcacacagga acagctatg  accatgatta cgaattcgag   180
ctcggtaccc ggggatcctc tagagtcgac ccgaagatct gaagattcct gatacaaatt   240
ctgttgtgac ggaagatttg ttggaagaaa tctagtcgct cgtctcataa aaacgaccga   300
gcctattggg attaccattg aagccagtgt gagttgcatc cactggctt  caaatcgag    360
actttacttt gtggattcac ggggtgtag  tgcaattcat aattagcccc attcggggga   420
gcagatcgcg gcgcgaacga tttcaggttc gttccctgca aaaactattt agcgcaagtg   480
ttggaaatgc ccccgtctgg ggtcaatgtc tattttgaa  tgtgtttgta tgattttgaa   540
tccgctgcaa aatcttttgtt tccccgctaa agttggggac aggttgacac ggagttgact   600
cgacgaatta tccaatgtga gtaggtttgg tgcgtgagtt ggaaaatttc gccatactcg   660
cccttgggtt ctgtcagctc aagaattctt gagtgaccga tgctctgatt gacctaactg   720
cttgacacat tgcatttcct acaatcttta gaggagacac accatggctg ttttggcgga   780
tgagagaaga ttttcagcct gatacagatt aaatcagaac gcagaagcgg tctgataaaa   840
cagaatttgc ctggcggcag tagcgcggtg gtcccacctg accccatgcc gaactcagaa   900
gtgaaacgcc gtagcgccga tggtagtgtg gggtctcccc atgcgagagt agggaactgc   960
caggcatcaa ataaaacgaa aggctcagtc gaaagactgg gcctttcgtt ttatctgttg  1020
tttgtcggtg aacgctctcc tgagtaggac aaatccgccg ggagcggatt tgaacgttgc  1080
gaagcaacgg cccggagggt ggcgggcagg acgcccgcca taaactgcca ggcatcaaat  1140
taagcagaag gccatcctga cggatggcct ttttgcgttt ctacaaactc tttcatgggg  1200
atccgtcgac ctgcaggcat gcaagcttgg cactggccgt cgttttacaa cgtcgtgact  1260
gggaaaaccc tggcgttacc caacttaatc gccttgcagc acatccccct ttcgccagct  1320
ggcgtaatag cgaagaggcc cgcaccgatc gcccttccca acagttgcgc agcctgaatg  1380
gcgaatgcga tttattcaac aaagccgccg tcccgtcaag tcagcgtaat gctctgccag  1440
tgttacaacc aattaaccaa ttctgattag aaaaactcat cgagcatcaa atgaaactgc  1500
aatttattca tatcaggatt atcaatacca tatttttgaa aaagccgttt ctgtaatgaa  1560
ggagaaaact caccgaggca gttccatagg atggcaagat cctggtatcg gtctgcgatt  1620
ccgactcgtc caacatcaat acaacctatt aatttcccct cgtcaaaaat aaggttatca  1680
agtgagaaat caccatgagt gacgactgaa tccggtgaga atggcaaaag cttatgcatt  1740
```

```
tctttccaga cttgttcaac aggccagcca ttacgctcgt catcaaaatc actcgcatca    1800
accaaaccgt tattcattcg tgattgcgcc tgagcgagac gaaatacgcg atcgctgtta    1860
aaaggacaat tacaaacagg aatcgaatgc aaccggcgca ggaacactgc cagcgcatca    1920
acaatatttt cacctgaatc aggatattct tctaatacct ggaatgctgt tttcccgggg    1980
atcgcagtgg tgagtaacca tgcatcatca ggagtacgga taaaatgctt gatggtcgga    2040
agaggcataa attccgtcag ccagtttagt ctgaccatct catctgtaac atcattggca    2100
acgctacctt tgccatgttt cagaaacaac tctggcgcat cgggcttccc atacaatcga    2160
tagattgtcg cacctgattg cccgacatta tcgcgagccc atttataccc atataaatca    2220
gcatccatgt tggaatttaa tcgcggcttc gagcaagacg tttcccgttg aatatggctc    2280
ataacacccc ttgtattact gtttatgtaa gcagacagtt ttattgttca tgatgatata    2340
tttttatctt gtgcaatgta acatcagaga ttttgagaca caacgtggct ttgttgaata    2400
aatcgaactt tgctgagtt gaaggatcag atcacgcatc ttcccgacaa cgcagaccgt    2460
tccgtggcaa agcaaaagtt caaaatcacc aactggtcca cctacaacaa agctctcatc    2520
aaccgtggct ccctcacttt ctggctggat gatgggcga ttcaggcctg gtatgagtca    2580
gcaacacctt cttcacgagg cagacctctc gacggagttc cactgagcgt cagacccgt    2640 agaaaagatc aaaggatctt cttgagatcc ttttttctg cgcgtaatct gctgcttgca    2700
aacaaaaaaa ccaccgctac cagcggtggt ttgtttgccg gatcaagagc taccaactct    2760
ttttccgaag gtaactggct tcagcagagc gcagatacca aatactgttc ttctagtgta    2820
gccgtagtta ggccaccact tcaagaactc tgtagcaccg cctacatacc tcgctctgct    2880
aatcctgtta ccagtggctg ctgccagtgg cgataagtcg tgtcttaccg ggttggactc    2940
aagacgatag ttaccggata aggcgcagcg gtcgggctga acggggggtt cgtgcacaca    3000
gcccagcttg gagcgaacga cctacaccga actgagatac ctacagcgtg agctatgaga    3060
aagcgccacg cttcccgaag ggagaaaggc ggacaggtat ccggtaagcg cagggtcgg    3120 aacaggagag cgcacgaggg agcttccagg gggaaacgcc tggtatcttt atagtcctgt    3180
cgggtttcgc cacctctgac ttgagcgtcg attttgtga tgctcgtcag gggggcggag    3240
cctatggaaa aacgccagca acgcggcctt tttacggttc ctggccttt gctggccttt    3300 tgctcacatg ttcttcctg cgttatcccc tgattctgtg gataaccgta ttaccgcctt    3360
tgagtgagct gataccgctc gccgcagccg aacgaccgag cgcagcgagt cagtgagcga    3420
ggaagcggaa gaagctcgca cattcagcag cgttttcag cgcgttttcg atcaacgttt    3480
caatgttggt atcaacacca ggtttaactt tgaacttatc ggcactgacg gttactgatt    3540
ttgaactttt gctttgccac ggaacggtct gcgttgtcgg gaagatgcgt gatctgatcc    3600
ttcaactcag caaaagttcg ccaatacgca aaccgcctct ccccgcgcgt tggccgattc    3660
attaatgcag ctggcacgag atctgacttg gttacgatgg actttgaaca cgccgagggt    3720
gactaaaccg ctggatttac gcggttttct tctcttcaac ttctttgacg tagcggtgaa    3780
ccgtgcccac cgagcaacca atctctgccg cgatagcgcg catggacaga cctttggcgc    3840
gcagctcctg gacgcgagca cgcttctcgt tggcacgttt aatgaacact tcacgcggtt    3900
cggaagtcca tcgttgagct gttctcaccg acataccggc acgttctgcc agctcgcggg    3960
ctgtttttcc gttgcgtgga taacgtgcat aaaccttagc caatgttcct ccaaagagta    4020
tgtccagcct cacgacgcac ctcagcgctt cgttgccagc cttcttccc gcgtgcggat    4080 tgcattgcgg tgaatgtggc gtcgtagacg gcggcgccgt ctgtccacat gcgtgacttg    4140
```

-continued

```
gtgatgatcc atttatggat tgacctggca atacagtcaa cttcggccac aggtagtggt    4200
tcatcaaaca gctcttggtt aagtgcttgc gcggtggttt ggattgcgcg gcctaggccg    4260
tcagcgtctc caaaatgctt tctgacctcc cgatatgccc acgtacgtgc gctttcaaag    4320
agtgcgcaat tacgacctag accaactggc gagaaccgcc gcgttttcct ccaggacgca    4380
ggcggcataa agccggtttc ttcgagccaa aagcgcagct catcgagcgt atacagctta    4440
tcggtgatcc agtgactatc ccatgcagtg tgctcggggt ttttggtgat cagcccggag    4500
tatccgctat cgccatcgac agagcgccgt aggccttcgg tgacagccgc ggcataggcc    4560
aaaggcttgc gtttggcgta ttcggtgcgg gtaaatggct ccgcgagcgc ccagacagcg    4620
tgtgcgtgcc cgtttaaggg gttttcaacc accgcgttag gtctccagtc ctccctgtcc    4680
cacaaagagc gcaaaagcgc gtcctcctgg tcgatgtcaa cgaccaggag gttagagagc    4740
gcgtcgggat tggcttcgac gtagcgctta ccagcgcgt tcttccgtga ggtgcggtaa    4800
atgccctcac ggaggtcatc gcttgccaat ggccacagcg gcagccacag ctgctcaaag    4860
cgtccctcag ggcgggtagt tggtctcatg tagctgactt tctcacacga gcgtgcacgg    4920
tcggttttca ttcataatac gacatttaac caagtcagat gttttcccgg tttccggggg    4980
ttcccctgaa gaaccctttcc agtgcgagcg aagcgagctc ctttggccgg cgcccctcag    5040
gtagccctct aaggctccca gggctccgcc cctccctgag gttggctcaa gcctcctggt    5100
ggctcctacg gacgttct                                                 5118
```

<210> SEQ ID NO 14
<211> LENGTH: 29
<212> TYPE: DNA
<213> ORGANISM: Artificial sequence
<220> FEATURE:
<223> OTHER INFORMATION: PCR primer

<400> SEQUENCE: 14

```
ctctcatatg ctgttttggc ggatgagag                                       29
```

<210> SEQ ID NO 15
<211> LENGTH: 33
<212> TYPE: DNA
<213> ORGANISM: Artificial sequence
<220> FEATURE:
<223> OTHER INFORMATION: PCR primer

<400> SEQUENCE: 15

```
ctctcatatg gtgtctcctc taaagattgt agg                                  33
```

<210> SEQ ID NO 16
<211> LENGTH: 2285
<212> TYPE: DNA
<213> ORGANISM: Bacillus subtilis

<400> SEQUENCE: 16

```
atgaaagcag aattcaagcg taaggagggg ggcaaagtga aactcgttgt cggaatgaca    60
ggggcaacag gggccatttt cggggtcagg ctgctgcagt ggctgaaggc cgccggagtg    120
gaaacccatc tcgttgtgtc tccttgggca acgtcacga tcaaacacga aacaggctat    180
acgttacaag aagtagaaca actggccaca tacacttact cacataagga tcaggcggca    240
gccatttcaa gcgggtcgtt tgataccgat ggaatgattg ttgcgccgtg cagcatgaaa    300
tctctcgcaa gcattcgcac aggaatggcg gataatctgc tgacacgtgc ggcggatgtc    360
```

```
atgctcaagg agagaaaaaa actcgtcctc ttaacgagag agacgccttt gaaccaaatt      420
catctcgaaa atatgctagc gcttacgaaa atgggcacca tcattcttcc tccgatgccg      480
gcattttata atcggccgag aagcttagag gaaatggttg accatattgt ttttagaacg      540
ttggaccaat tcggcattcg gcttcctgaa gcgaagcgct ggaatgggat tgaaaaacaa      600
aaaggaggag cttgatcatg gcttatcaag atttcagaga atttctcgct gcccttgaaa      660
aagaaggaca gctgcttaca gtgaatgaag aggtaaagcc ggaaccggat ttaggggcct      720
ccgcacgggc agccagcaat cttggcgata aaagccctgc gctcttattt aacaacattt      780
acggctatca taacgcgcga attgcgatga atgtcatcgg ctcttggcca aaccatgcca      840
tgatgctggg catgccgaaa gacacaccgg taaagaaaca gtttttttgaa ttcgcaaagc      900
gttatgacca gtttccgatg ccggtcaaac gtgaggaaac agcgccattt catgaaaatg      960
aaatcacaga agatatcaat ttgttcgata tactgcctct tttcagaatt aaccagggtg     1020
atggaggcta ctatttagac aaagcatgtg tcatttcccg tgatcttgag gaccctgaca     1080
acttcggcaa acaaaatgtc ggcatttaca gaatgcaagt caaggaaaaa gaccgccttg     1140
gcattcagcc tgtcccgcag cacgatattg caatccatct gcgccaagct gaagaacgcg     1200
gcatcaacct tccggtcact attgcgctcg gctgtgagcc ggtcattaca acggcggcat     1260
cgactccgct tctctatgat caatcagaat acgaaatggc aggtgcgatt caaggcgaac     1320
catatcgcat cgtcaaatca aagctgtctg atcttgatgt tccgtggggc gctgaagtgg     1380
tgcttgaagg tgagattatt gccggagagc gcgaatatga agggccgttc ggtgaattca     1440
caggccatta ttccggcgga cgcagcatgc cgattatcaa aattaaacgc gtctatcaca     1500
gaaacaatcc gatctttgaa catttatact taggcatgcc ttggacagaa tgcgattaca     1560
tgatcggcat taacacatgc gtgccgcttt atcagcagtt aaaagaagcg tatccgaacg     1620
aaattgtggc agtgaacgcc atgtacacac acggtttaat cgcgattgtt ccacaaaaaa     1680
cccgctatgg cggatttgcg aaagcggtcg gcatgcgcgc actcacaacg ccgcacggac     1740
tcggctactg caaaatggtc atagtcgttg atgaggatgt cgatccattc aaccttccgc     1800
aggtcatgtg ggcgctttcg accaaaatgc atccgaaaca tgatgcggtc atcattccgg     1860
acttatctgt cctgccgctt gatccgggat ccaatccatc aggaatcact cacaaaatga     1920
ttctcgacgc cactacaccg gttgcgccgg aaacaagagg ccattattca cagccgcttg     1980
attctccgct aacaacgaaa gaatgggaac aaaaactaat ggacttaatg aataaataag     2040
gaaaggatgt tcgaaatgca tacatgtcct cgatgcgact caaaaaaggg agaagtcatg     2100
agcaaatcgc ctgtagaagg cgcatgggaa gtttatcagt gccaaacatg cttttttaca     2160
tggagatcct gtgaaccgga aagcattaca aatcccgaaa aatacaatcc agcgtttaaa     2220
attgatccaa aggaaacaga aacagcaatt gaagttccgg cggtgccgga acgaaaggct     2280
tgatc                                                                 2285
```

<210> SEQ ID NO 17
<211> LENGTH: 32
<212> TYPE: DNA
<213> ORGANISM: Artificial sequence
<220> FEATURE:
<223> OTHER INFORMATION: PCR primer

<400> SEQUENCE: 17
ctctcatatg aaagcagaat tcaagcgtaa ag                                      32

```
<210> SEQ ID NO 18
<211> LENGTH: 29
<212> TYPE: DNA
<213> ORGANISM: Artificial sequence
<220> FEATURE:
<223> OTHER INFORMATION: PCR primer

<400> SEQUENCE: 18
ctctcatatg gatcaagcct ttcgttccg                                     29

<210> SEQ ID NO 19
<211> LENGTH: 29
<212> TYPE: DNA
<213> ORGANISM: Artificial sequence
<220> FEATURE:
<223> OTHER INFORMATION: PCR primer

<400> SEQUENCE: 19
ctcttctaga tacgtcctaa acacccgac                                     29

<210> SEQ ID NO 20
<211> LENGTH: 40
<212> TYPE: DNA
<213> ORGANISM: Artificial sequence
<220> FEATURE:
<223> OTHER INFORMATION: PCR primer

<400> SEQUENCE: 20
gaccaaccat tgctgacttg cgtatccata gtcaggcttc                         40

<210> SEQ ID NO 21
<211> LENGTH: 20
<212> TYPE: DNA
<213> ORGANISM: Artificial sequence
<220> FEATURE:
<223> OTHER INFORMATION: PCR primer

<400> SEQUENCE: 21
caagtcagca atggttggtc                                               20

<210> SEQ ID NO 22
<211> LENGTH: 30
<212> TYPE: DNA
<213> ORGANISM: Artificial sequence
<220> FEATURE:
<223> OTHER INFORMATION: PCR primer

<400> SEQUENCE: 22
ctcttctaga tgatcagtac caagggtgag                                    30

<210> SEQ ID NO 23
<211> LENGTH: 2249
<212> TYPE: DNA
<213> ORGANISM: BAcillus atrophaeus

<400> SEQUENCE: 23
atgaaactcg ttgtcgggat gaccggagct acaggggcta ttttcggagt caggcttta    60 gaatggctga aggccgcagg agcggaaact caccttgtcg tttctccttg ggctcatgtc   120
acaatcaaac atgaaacagg ttatagctta aagaagttg aagagcttgc ctcatatacg    180
tactctcata aggatcaggc ggctgccatt tcaagcgggt cttttcaaac ggacggcatg   240
atcgtcgccc cgtgcagtat gaagtcgctc gcaagcattc gcacggggat ggcggacaat   300
ctgctgaccc gggctgcaga tgtcatgctg aaagagagaa aaaagcttgt cctgctgacg   360
```

```
agagaaacgc cgcttaacca gattcattta gagaatatgc tcgcattaac aaagatggga      420
accattattc ttccgccaat gccggctttt tataatcagc cggcaagtct ggatgaaatg      480
gtggaccata ttgtattcag aacgctggat caattcggca ttcgccttcc tgaggcaaaa      540
cgctggaatg gaattgaaaa agaaaaagga ggagcttgat catggcttat caagatttca      600
gagaatttct cgctgccctg aaaaagagg dacagctatt aaaagtggat gaagaggtga      660
```

```
agccggagcc ggatttagga gccgcagccc gcgcagccaa caacctcggt gataaaagcc      720
cggctctttt atttaacaat atttacggct acaacaatgc acaaatcgcg atgaatgtca      780
tcggttcttg gccgaaccac gcgatgatgc ttggcttgcc gaaagataca ccggttaaag      840
agcagttttt tgaatttgcg aagcgatatg aacagtttcc gatgccggtc aaacgcgaag      900
aaactgcgcc atttcatgaa aatgaaatca cagaggacat caacctattc gatatattgc      960
ctcttttcag aattaaccag ggtgacggcg gctattattt agataaagcg tgtgtcattt     1020
cccgtgatct ggatgaccct gacaacttcg gcaagcagaa cgtcggaatt taccgcatgc     1080
aggtaaaagg gaaagaccgc ctcggcattc agccagttcc gcagcatgac atcgcgattc     1140
atcttcgcca agcagaagaa cgcggcatca atcttccggt caccatcgcg cttggctgtg     1200
agcctgtcat tacgaccgcg gcgtcaactc cgctcctata tgaccaatcg gaatatgaaa     1260
tggcgggagc gatccagggc gaaccgtata aatcgtcaa atcaaagctg tctgaccttg     1320
atattccttg gggcgcagaa gtcgtgcttg aaggagaaat cattgccgga gaacgggaat     1380
atgaaggacc gttcggcgaa tttaccggcc attattcagg cggacgcagc atgccgatta     1440
tcaaaatcaa acgcgtatct catagaaatc atccggtatt tgaacattta tatctcggca     1500
tgccttggac agagtgcgat tacatgatcg gcattaatac atgcgtgccg ctttatcagc     1560
agctgaaaga agcatatccg agtgaaattg tcgctgtgaa cgcaatgtac acacatggct     1620
taatcgccat tgtatctaca aaaacccgtt acggaggatt tgcaaaagct gtcggaatga     1680
gagccctgac tacaccgcac ggactcggct actgtaagat ggtgatcgtc gtggatgaag     1740
atgttgatcc gttcaaccct ccgcaagtca tgtgggcgct ttcaacaaag atgcatccga     1800
agcatgatgt cgtaactatt cctgatttat ccgtgctgcc gcttgatccg ggatcagacc     1860
catccggcat tactcataaa atgattctcg atgccacaac gcctgttgcg ccggaaacaa     1920
gaggccatta ttcacagccg cttgactctc ctttaacaac aaaagaatgg gaacaaaaac     1980
taatggactt gatgaataaa taagagaaag gatgatccga catgcatacac tgtcctcgat     2040 gtgattcaaa aaagggagaa atcatgagca aatcgcctgt agaaggcgct tgggaagtct     2100
accaatgcca aacatgtttc ttcacatgga gatcatgtga accggaaagc attacaaacc     2160
cgaaacaata caatccatca tttaagatcg atccgaagga aacagaaaca gctgttgaag     2220
tgccggctgt tccggaaaga aaggcctga                                         2249
```

<210> SEQ ID NO 24
<211> LENGTH: 28
<212> TYPE: DNA
<213> ORGANISM: Artificial sequence
<220> FEATURE:
<223> OTHER INFORMATION: PCR primer

<400> SEQUENCE: 24
ctctcatatg aaactcgttg tcgggatg                                          28

<210> SEQ ID NO 25
<211> LENGTH: 26

```
<212> TYPE: DNA
<213> ORGANISM: Artificial sequence
<220> FEATURE:
<223> OTHER INFORMATION: PCR primer

<400> SEQUENCE: 25
ctctcatatg tcaggccttt ctttcc                                              26

<210> SEQ ID NO 26
<211> LENGTH: 2283
<212> TYPE: DNA
<213> ORGANISM: Bacillus subtilis subsp.spizienii

<400> SEQUENCE: 26
atgaaagcag aattcaagcg taaaggaggg ggcaaagtga aactcgttgt cggaatgaca    60
ggggcaacag gggctatttt cggggtcagg ctgctggagt ggctgaaggc ggccgaagta   120
gaaacccatc tcgtcgtgtc tccttgggct aacgtcacga tcaaacacga aacaggctat   180
accttaaaag aagtagaaca acttgccaca tacacgtatt cgcataagga ccaggcggca   240
gccatttcaa gcgggtcgtt tgataccgat ggcatgattg ttgcgccatg cagcatgaaa   300
tctctcgcaa gcattcgcac cgggatggcg ataatctgc tgacgcgtgc ggcggatgtc    360
atgctcaagg agagaaaaaa actcgtcctc ttaacgagag agacgccttt gaaccagatt   420
catctcgaaa atatgctagc gcttacgaaa atgggtacca tcattcttcc tccgatgccg   480
gcattttata atcagccgag cagcttagag gaaatggttg accatattgt attcagaacg   540
ttggaccaat tcggcattcg ccttcctgaa gcgaaacgct ggaatgggat tgaaaaacaa   600
aaggaggag cttgatcatg gcttatcaag atttcagaga atttctcgct gcccttgaaa    660
aagaaggaca gctgctaaca gtgaatgaag aggtaaagcc ggagccggat ataggggctg   720
cagcacgcgc agccagcaat cttggcgata aagccccgc gctcttattt aataacattt     780
atggctatca caacgcgcaa attgcgatga atgtgatcgg ctcctggccg aaccatgcaa   840
tgatgctggg catgccgaaa gacacgccgg tgaaagaaca gttttttgaa tttgcgaaac   900
gttatgacca gtttccgatg ccagtcaaac gtgaggaatc agcgccgttt catgaaaatg   960
aaatcacaga agatatcaat ttgttcgata tactgcctct tttcagaatt aaccaaggag  1020
acggcggtta ctatctagac aaagcatgtg tcatttcccg cgatcttgaa gatcctgaga  1080
atttcggcaa acaaaacgtc gggatttaca gaatgcaggt caaaggaaaa gaccgccttg  1140
gcattcagcc tgtgccgcag cacgatattg cgatccatct gcgtcaagct gaagaacgcg  1200
gcatcaatct tccggtcacc attgcgctcg gctgtgagcc ggtcataaca acggcggcat  1260
cgactccgct tctttatgat caatcagaat acgaaatggc aggcgcaatt caaggtgaac  1320
catatcgcat cgtgaaatct aagctgtctg atcttgatgt tccatggggc gctgaagtag  1380
tgcttgaagg tgaaatcatt gccggagagc gtgaatatga aggcccgttc ggtgagttca  1440
caggccatta ttccggcgga cgcagcatgc cgattattaa aattaaacga gtgtatcata  1500
gaaacaatcc gatttttgaa catttatact taggcatgcc ttggacagaa tgcgattaca  1560
tgattggcat taacacttgt gtgccgcttt atcagcagtt aaaagaagcg tatccgaatg  1620
aaattgtggc tgtgaacgcc atgtacacac acggtttgat cgcgattgtt ccacaaaaaa  1680
cacgctatgg cggatttgcg aaaagcagtcg gcatgcgcgc gctcacaaca ccgcacggac  1740
tcggctactg caaaatggtc attgtcgttg acgaggatgt cgatccattc aatctgccgc  1800
aggtcatgtg ggcgctttcg accaaaatgc atccgaagca cgatgcggtc atcattccag  1860
```

```
acttatctgt cctgccgctt gacccgggat ctaatccatc aggaatcact cacaaaatga    1920
ttcttgacgc cactacaccg gttgcgccgg aaacaagagg ccattattca cagccgcttg    1980
attcaccatt aacaacgaaa gaatgggaac aaaaactaat ggacttaatg aataaataag    2040
aaaaggatga tcgaaatgca tatatgtcct cgttgcgatt cgaaaaaggg agaagtcatg    2100
agcaaatcgc ctgtagaagg cgcatgggaa gtttatcagt gtcaaacatg ttttttcaca    2160
tggagatcct gtgagccgga aagtattaca aatccggcga aatacaatcc agcgtttaaa    2220
attgatccga aggaaacaga aacagcaatt gaagttccgg ctgtgccgga acgaaaggct    2280
tga                                                                 2283

<210> SEQ ID NO 27
<211> LENGTH: 32
<212> TYPE: DNA
<213> ORGANISM: Artificial sequence
<220> FEATURE:
<223> OTHER INFORMATION: PCR primer

<400> SEQUENCE: 27
ctctcatatg aaagcagaat tcaagcgtaa ag                                  32

<210> SEQ ID NO 28
<211> LENGTH: 28
<212> TYPE: DNA
<213> ORGANISM: Artificial sequence
<220> FEATURE:
<223> OTHER INFORMATION: PCR primer

<400> SEQUENCE: 28
ctctcatatg tcaagccttt cgttccgg                                       28

<210> SEQ ID NO 29
<211> LENGTH: 2268
<212> TYPE: DNA
<213> ORGANISM: Citrobacter koseri

<400> SEQUENCE: 29
atgagactga ttgtggggat gaccggcgca acggggcgc cgctaggcat tgcgctgcta      60
caggcgctgc ggcaaatgcc gacagtagaa acacacctgg taatgtctaa gtgggccaaa    120
acgaccattg agctggaaac gccttacagt gcgcgagatg ttgccggact ggctgattac    180
tgccataacc cggcggatca ggcggcgacg atctcttccg gctcatttcg caccgacggc    240
atgatcatta tgccttgcag tatgaaaacg ctggcgggga ttcgcgcagg atatgccgag    300
gggttagttg ccgtgccgc cgatgtggtg ctgaaagaag ggcgcaaact ggtgctggtg    360
ccgcgtgaaa tgccgctcag cacgatccat ctggaaaaca tgctcgccct ttcccgcatg    420
ggggtcgcga tggtgccgcc catgcctgct ttctacaacc atccgcaaac tattgatgat    480
attacgcagc atattgtggc gcgtgtgctg atcagtttg gtctgagca tccgcgtgcc    540 cggcgctggc aggggttgca gcaggcgcag aattttcac aggagaatga ataatggcat    600
ttgatgactt acgcagcttt ttgcaggcgc tcgacgagca ggggcaactg ctgaaaatca    660
gtgaagaagt gaatgcagag ccggatctgg ctgctgcggc taacgcaacc gggcgcattg    720
gcgacggcgc gcctgcgctg tggttcgata atatccgtgg cttcacggat gcgcgcgtgg    780
cgatgaacac cattggttcc tggcagaacc atgccatctc tttaggcttg ccgcctaatg    840
cgccagtaaa aaagcaaatt gatgaattta tccgccgctg gacacgttc cccgtcgccc    900 ccgagcgccg agccaacccg gcgtgggcgg aaaacaccgt tgatggcgag gcgatcaacc    960
```

```
tgtttgatat tctgccgctg tttcgcctca acgatggcga tggcggcttc tatctggata    1020
aagcctgtgt cgtctcccgc gatccgctcg acccggatca cttcggcaag cagaatgtgg    1080
gtatctaccg gatggaagtg aaaggcaagc gcaagctggg cctgcaaccg gtgccaatgc    1140
acgatatcgc gctgcatctg cataaggcgg aagagcgtgg cgaagatctg ccgattgcta    1200
ttacgctcgg taacgatccg atcatcactc tgatgggcgc cacgccgctg aaatacgatc    1260
agtctgagta tgaaatggcg ggcgcgctgc gcgaaagccc atacccgatc gccaccgcgc    1320
cgctgaccgg ctttgatgtg ccgtggggtt cagaagtgat ccttgaaggg gtgatcgaaa    1380
gccgtaagcg tgaaattgaa gggccgtttg gcgagtttac cggccactat tctggtgggc    1440
gcaatatgac ggtggtgcgc atcgacaaag tgtcttatcg cactaaaccg attttttgaat    1500 cactctatct ggggatgccg tggactgaaa tcgactacct gatggggcca gcgacctgtg    1560
tgccgctgta tcagcagttg aaagcggaat cccggaagt gcaggcggtt aacgccatgt    1620
atacccacgg tctgctggcg attatctcga ccaaaaaacg ctacggcgga tttgcccgcg    1680
cgatcggcct gcgggcaatg accacgccgc acggtctggg ctatgtgaag atggtgatta    1740
tggttgatga ggatgtcgat ccgttcaacc tgccgcaggt gatgtgggcg ctgtcgtcga    1800
aggtcaaccc ggcaggcgat ctggtgcagc tgccgaacat gtcggtgctg aactggacc    1860 caggctcaag cccggcgggg atcactgaca aactgatcat cgacgccaca acgccggttg    1920
cgccggataa tcgcggccac tacagccagc cggtatgtga tttaccggaa accaaagcct    1980
gggctgaaaa gctgactgcc atgctggcca accgtaaata aggagtagca gatgatttgt    2040
ccacgttgtg ctgatgaaca tattgaattg atggcgacct ctccggtcaa agggatctgg    2100
acggtgtatc agtgccagca ttgtctgtac acctggcgtg ataccgagcc gctacgccgt    2160
accagccgtg aacattatcc gcaagcgttt cgcatgacgc agaaagatat tgatcaagcg    2220
ccgatggtgc cgggcattcc accgctgctg gcggaagata agcgttaa            2268
```

<210> SEQ ID NO 30
<211> LENGTH: 28
<212> TYPE: DNA
<213> ORGANISM: PCR primer

<400> SEQUENCE: 30

```
ctctcatatg agactgattg tggggatg                                        28
```

<210> SEQ ID NO 31
<211> LENGTH: 31
<212> TYPE: DNA
<213> ORGANISM: Artificial sequence
<220> FEATURE:
<223> OTHER INFORMATION: PCR primer

<400> SEQUENCE: 31

```
ctctcatatg ttaacgctta tcttccgcca g                                   31
```

<210> SEQ ID NO 32
<211> LENGTH: 2268
<212> TYPE: DNA
<213> ORGANISM: Enterobacter aerogenes

<400> SEQUENCE: 32

```
atgaaactga ttattgggat gaccggggcg accggcgcgc cgttaggcgt cgcgctgtta    60
caggcgctga atgaaatgcc ggatgtggaa acgcatctgg tcatgtcgaa atgggcaaaa    120
```

```
accaccattg agctggaaac gccctatagc gctcgtgatg tcgccgcgct ggcggacttc    180
tgccatagcc ctgcggatca ggccgcgacc atctcatcag gatcgtttcg taccgacggc    240
atgattgtta tccectgcag catgaaaacg ctggcgggta ttcgcgctgg ctatgcggaa    300
gggttagtcg gccgcgcggc ggacgtggtg ctgaaagagg ggcgcaagct ggttctggtg    360
ccgcgtgaaa tgccgctgag caccattcat ctggagaaca tgctggcgct gtcgcgcatg    420
ggcgtggcga tggtgccgcc catgcctgcc tattacaacc acccggaaac ggtagaggat    480
atcaccaacc atatcgtgac ccgggtgctg gatcagtttg gtctcgaata tcacaaagcg    540
cgccgctgga acggcctgcg cgcggtcgag aatttatcac aggagaatta atcatggctt    600
ttgatgattt acgcagcttt ttgcaggcgc ttgatgagca ggggcaactg ctaaaaatta    660
gcgaagaggt gaatgccgag ccggatctcg ccgctgccgc taacgccaca gggcgcatcg    720
gtgacggcgc gccagcgttg tggtttgata acattcgcgg ctttaccgac gcccgtgtcg    780
ccatgaacac catcggttcc tggcaaaaac acgcgatttc gctggggctg ccgccaaaca    840
cgccggtgaa aaagcagatt gatgaattta ttcgccgctg ggataaattc ccggtaacgc    900
cggagcgtcg cgctaatcca gcgtgggcgg aaaacaccgt tgatggcgac gatatcaacc    960
tgttcgatat tctgccgctg ttccgcctga cgatggcgca cggtggtttc tatctcgaca   1020
aagcctgtgt ggtttcgcgc gatccgcttg acccggacca ctttggcaaa cagaacgtcg   1080
gtatttaccg gatggaagtg aaaggcaagc gcaagctggg cctgcagccg gtaccgatgc   1140
acgatatcgc gctgcatctg cataaagcgg aagagcgcgg tgaggatctg cccattgcca   1200
tcaccctggg taacgacccg attattaccc tgatgggcgc gacgccgctg aaatatgacc   1260
agtcagaata tgagatggcg ggcgcgctgc gcgaaagccc gtatcccatc gccaccgcgc   1320
cgctgaccgg ctttgacgtt ccctgggget cagaggtgat ccttgaaggg gtgattgaag   1380
ggcgcaagcg tgaaatcgaa gggccgttcg gcgagttcac cggccactac tcaggcggcc   1440
gcaatatgac ggtggtgcgt atcgataaag tctcttatcg cacaaaaccg atttttgaat   1500
cgttgtatct cggaatgccg tggaccgaaa tcgactatct gatgggcccg gcgacctgcg   1560
tgccgctgta ccagcagctg aaggcggagt tcccggaggt gcaggcggtc aatgccatgt   1620
acacccatgg tctgctggcg attatctcca ccaaaaaacg ctacggcggt tttgcccgcg   1680
cggtgggatt acgggcaatg actaccccgc acggcctcgg ttacgtgaaa atggtgatca   1740
tggtcgatga agatgtcgat ccgttcaacc tgccgcaggt gatgtgggcg ctctcctcga   1800
aggtcaaccc ggcgggcgac ctggtacagt tgccgaacat gtcggtgctg gagcttgacc   1860
ctggttccag tccggcgggg atcaccgaca aactgattat cgacgccacc accccggttg   1920
cgcctgacct tcgcggtcac tacagccagc cggttcagga tttaccggaa accaaagcct   1980
gggctgaaaa actgaccgcc atgttggcca accgtaaata aggagaagaa gatgatttgt   2040
ccacgttgcg ctgatgagca gattgaagtg atggcgacgt cgccggtaaa aggggtgtgg   2100
atcgtttacc agtgccagca ctgcctctat acctggcgta taccgaacc gctgcgtcgt   2160 accagccgcg aacattatcc ggaagcgttc cgcatgacgc agaaagatat tgatgaggcg   2220
ccgcaggtgc cgcatattcc accgctgttg gcggcagata agcgttaa                2268
```

<210> SEQ ID NO 33
<211> LENGTH: 32
<212> TYPE: DNA
<213> ORGANISM: Artificial sequence
<220> FEATURE:
<223> OTHER INFORMATION: PCR primer

```
<400> SEQUENCE: 33
ctctcatatg aaactgatta ttgggatgac cg                                  32

<210> SEQ ID NO 34
<211> LENGTH: 29
<212> TYPE: DNA
<213> ORGANISM: Artificial sequence
<220> FEATURE:
<223> OTHER INFORMATION: PCR primer

<400> SEQUENCE: 34
ctctcatatg ttaacgctta tctgccgcc                                     29

<210> SEQ ID NO 35
<211> LENGTH: 2252
<212> TYPE: DNA
<213> ORGANISM: Enterobacter cloacae

<400> SEQUENCE: 35
atgagattga tcgtgggaat gacgggagca acaggtgctc cgctgggtgt ggctttactg     60
caggcgttac gtgacatgcc agaggttgaa acccatctgg tgatgtcgaa atgggcgaaa    120
accaccattg agctggaaac gccttatacc gcgcaggatg tcgccgccct ggcagatgtc    180
gttcacagtc ctgccgatca ggctgccacc atctcctccg ctcgtttcg taccgacggc     240 atgatcgtca ttccctgcag catgaaaacg ctggcgggta tccgcgcggg ctatgccgaa    300
gggctggtgg ccgtgcggc agacgtggtg ctgaaagagg ggcgcaagct ggtgctggtc     360
ccgcgtgaaa cgccgctcag caccattcat ctggagaaca tgctcgcgct ttcccgcatg    420
ggggtggcga tggtgccgcc catgcctgcg tattacaacc cccgcaaac cgccgatgat     480 atcacccagc atatcgtgac ccgcgtactc gaccagtttg gtctggagca aaaaaggcg     540 cgtcgctgga acggcctgca ggcggcgaaa catttttcac aggagaataa cgatggcatt    600 tgatgattg agaagcttcc tgcaggcgct agatgagcaa gggcaactgc tgaaaattga     660
agaagaggtc aatgcggagc cggatctggc ggcggccgct aacgcgacgg gacgtatcgg    720
tgatggtgcg cctgcgctgt ggttcgataa cattcgcggg tttaccgatg ccagggtggt    780
gatgaacacc atcggctcct ggcagaacca cgccatttcg atgggctgc ggcgaatac      840 cccggtcaaa aagcagatcg atgagttat tcgccgctgg ataaattcc cggtcgcacc      900 ggagcgccgg gccaaccccg catgggcgca gaatacggtg acggtgagg agattaacct     960 gttcgacatc ctgccgctgt ttcgcctgaa cgacggggac ggcggttttt atctcgacaa   1020
agcgtgcgtt gtctcgcgcg atccgctcga cccggaccat ttcggcaagc agaacgtcgg   1080
tatttaccgc atggaagtga agggcaaacg taagctcggc ctgcagccgg tgccgatgca   1140
tgatatcgcc ctgcatctgc ataaagccga agagcgtggt gaagacctgc cgattgcgat   1200
tacgttgggc aacgatccga tcatcaccct gatgggcgca acgccgctga atacgatca    1260 gtccgagtat gaaatggccg gggcgctgcg tgaaagcccg tacccgattg cgaccgcgcc   1320
gttgaccggc ttcgatgtgc cgtgggggtc tgaagtgatc ctggaagggg tgattgaagg   1380
ccgtaaacgt gaaattgaag gccgttcgg tgagtttacc gggcactatt cgggcggacg    1440
caatatgacg gtggtccgta ttgataaagt ctcgtaccgc accaaaccga ttttcgaatc   1500
cctctatctc gggatgccct ggaccagat cgactacctg atgggccag ccacctgtgt     1560 gccgctttac cagcaactga agcggagtt ccctgaagtg caggcggtga acgcgatgta    1620
```

```
tacccacggt ctgctggcga tcatctccac caaaaaacgc tacggtggtt ttgcccgcgc      1680
ggtcggttta cgcgccatga ccacgccgca tggcctgggc tatgtgaaga tggtgattat      1740
ggtggatgaa gatgtcgatc cgttcaacct gccgcaggtg atgtgggcgc tgtcatcaaa      1800
agtgaacccg gcaggggatc tggtgcagct gccgaacatg tcggttcttg agcttgatcc      1860
tgggtccagc ccggcaggca tcaccgacaa gctgattatt gatgccacca cgcctgttgc      1920
gccggataac cgcggtcact acagccagcc ggtgcaggat ttacctgaaa ccaaagcctg      1980
ggctgaaaag ctgactgcga tgctggcagc acgccaataa ggaggaaaag atgatttgtc      2040
cacgttgtgc cgatgagcaa attgaggtga tggccacatc accggtgaaa gggatctgga      2100
cggtttatca gtgccagcat tgcctgtata cctggcgcga tactgagccg ctgcgtcgta      2160
ccagccgcga acattaccct gaagcgttcc gcatgacgca aaggatatt gatgaggcgc       2220 cgcaggtacc gaccattccg ccattgctgt aa                                   2252

<210> SEQ ID NO 36
<211> LENGTH: 30
<212> TYPE: DNA
<213> ORGANISM: Artificial sequence
<220> FEATURE:
<223> OTHER INFORMATION: PCR primer

<400> SEQUENCE: 36
ctctcatatg agattgatcg tgggaatgac                                        30

<210> SEQ ID NO 37
<211> LENGTH: 30
<212> TYPE: DNA
<213> ORGANISM: Artificial sequence
<220> FEATURE:
<223> OTHER INFORMATION: PCR primer

<400> SEQUENCE: 37
ctctcatatg ttacagcaat ggcggaatgg                                        30

<210> SEQ ID NO 38
<211> LENGTH: 2358
<212> TYPE: DNA
<213> ORGANISM: Enterobacter hormaechei

<400> SEQUENCE: 38
atgagattga ttgtgggaat gacgggcgcg acgggtgcgc attaggcgt ggcgttgttg        60 caggcgctgc gggaaatgcc ggaggtggaa acgcacctgg tgatgacgaa gtgggcaaaa      120
accacgattg agctggaaac gcccttcact gcgcatgacg ttgctgcact ggcggatgtc      180
gtccacagtc cggccgatca ggctgccacc atctcctccg gctcgtttcg caccgacggc      240
atgatcgtca tcccgtgcag catgaaaacg ctggcgggga tccgcgcggg ctacgccgaa      300
gggctggtag gcgtgcggc agacgtggtg ctgaaagagg acgcaagct ggtgctggtt        360 ccccgcgaga cgccgctcag caccattcat cttgagaaca tgcttgccct ttcccgcatg      420
ggcgtggcga tggtgccgcc tatgcctgcg tactacaacc acccgcaaac cgccgatgac      480
attacccagc atatcgtgac ccgcgttctc gaccagtttg gtctggagca taaaaaagcc      540
cgacgctggg aaggtttgca ggcagcgaaa cattttttcac aggagaataa agatggcatt      600
tgatgatttg agaagcttct tgcaggcgct cgatgagcaa gggcagctgc tgaaaattga      660
ggaagaggta aacgcggagc cggatttagc ggcggccgcc aacgctaccg ggcgcattgg      720
cgatggcgcg cctgcgctgt ggttcgataa tattcgcggc ttcaccgatg cccgagtggt       780
```

-continued

```
gatgaacacc atcggctcgt ggcaaaacca cgccatttcg atggggctgc cagcgaatac      840
ttcggtgaaa aaacagatcg acgagtttat tcgtcgctgg acaaattcc ccgtcacgcc       900 agagcgtcgt gccaatcctg cctgggcgca gaacacggtg gacggagaag atatcaacct     960
gttcgacatt ttgccgctgt tccgcctgaa cgacggtgac gggggctttt atctcgataa    1020
agcgtgcgtt gtctcccgcg atccgctcga ccccgaccac ttcggcaagc agaacgtcgg    1080
catttaccgt atggaagtga agggcaagcg taagctcggc ctgcaaccgg tgccgatgca    1140
tgatattgcg ctgcatctgc ataaggcaga agagcgtggc gaagacctgc ccattgccat    1200
tacgctgggt aacgatccga tcatcaccct gatgggcgcc acgccgctga aatacgatca    1260
atccgagtat gagatggctg gcgcgctacg cgaaagcccg tatccgattg cgacggctcc    1320
gctgaccggt tttgatgtgc cgtggggtc ggaagtgatc ctggaagggg tgattgaagg    1380
ccggaaacgt gaaattgaag gaccattcgg tgagtttacc ggacactact ctggcgggcg    1440
caacatgacc gttgtgcgca ttgataaagt ctcttaccgc accaaaccca ttttcgaatc    1500
tctctacctg gggatgcctt ggaccgagat tgattatctg atgggacccg ccacctgcgt    1560
gccgctctat cagcaactga aggcggaatt cccggaagtg caggcggtaa acgccatgta    1620
cacccacggt ctgctggcaa ttatctccac taaaaagcgt tacggcggtt ttgcccgtgc    1680
ggtcgggcta cgcgccatga ccacaccgca cggtctgggt tacgtgaaga tggtgattat    1740
ggtggatgaa gatgtcgatc cgtttaacct gccgcaggtc atgtgggcgc tttcatcgaa    1800
ggttaatccg gcgggcgatc tggtgcagct tccgaatatg tctgtgctgg aacttgaccc    1860
tggctccagc ccggcgggga tcaccgacaa gctgatcatt gatgccacca cccctgttgc    1920
cccggacaac cgtggtcact acagccagcc ggtacaggac ctccctgaaa ccaaagcctg    1980
ggccgaaaaa ctgaccgcga tgctggcagc acgtcaataa ggaggaaaaa atgatttgtc    2040
cacgttgtgc cgatgaacat attgaagtaa tggcaacatc accggtgaaa ggtgtctgga    2100
cggtatatca gtgccagcac tgtctgtata cctggcgcga taccgaaccg ctacgccgta    2160
ccagccgcga gcattacccg gaagccttcc gcatgacgca gaaggatatt gatgaggcgc    2220
cgcaggtgcc aacaatcccg ccgctgctgt aaaaaaagcc cggtgcggc tgcgcttacc    2280 gggcctacgg gttttgtagg ccgggtaagg cgaagccgcc acccggcaaa aagaccgca    2340 gagaactaaa ccagactc                                                   2358
```

<210> SEQ ID NO 39
<211> LENGTH: 30
<212> TYPE: DNA
<213> ORGANISM: Artificial sequence
<220> FEATURE:
<223> OTHER INFORMATION: PCR primer

<400> SEQUENCE: 39
ctctcatatg agattgattg tgggaatgac         30

<210> SEQ ID NO 40
<211> LENGTH: 31
<212> TYPE: DNA
<213> ORGANISM: Artificial sequence
<220> FEATURE:
<223> OTHER INFORMATION: PCR primer

<400> SEQUENCE: 40
ctctcatatg gagtctggtt tagttctctg c         31

<210> SEQ ID NO 41
<211> LENGTH: 2284
<212> TYPE: DNA
<213> ORGANISM: Enterobacter sakazakii

<400> SEQUENCE: 41

| | | | | | |
|---|---|---|---|---|---|
| atgaggctaa | ttgtcggaat | gacgggcgca | accggcgcgc | cgcttggggt | cgcgctgttg | 60 |
| caggcgctga | aagcgatgcc | tgaggtggaa | acccatctgg | tgatgtcaaa | gtgggcgaaa | 120 |
| accacgatcg | aactggaaac | gccgttctcc | tggcaggatg | tcgcggggct | ggcagatgtg | 180 |
| gtgcacagcc | cggcggatca | ggccgcgacg | atctcctcag | gatcgtttcg | caccgacggc | 240 |
| atggtgatca | ttccgtgcag | catgaaaacc | ctggcgggca | tccgcgcggg | ctacgccgac | 300 |
| gggctggtgg | gccgcgccgc | tgatgtggtg | ctgaaagaga | accgtaaact | ggtgctggtg | 360 |
| ccgcgcgaaa | caccgcttag | caccattcat | ctggaaaacc | tgctggcgct | ctcgaagatg | 420 |
| ggcgtggcca | tcgtgccgcc | catgcccgcc | tggtacaacc | atcccgcgac | gatcgacgac | 480 |
| atcatcaacc | atatcgtcgc | gcgcgtgctc | gatcagttcg | ggctcgatgc | ccgcaacgcc | 540 |
| cgccgctggc | aggggctaaa | tcctgcgaaa | acagccgaca | cccattcatc | acgaggagga | 600 |
| aacacgcatg | gcgtttgacg | atctgcgcag | cttttttgcag | gcgcttgaag | agcagggca | 660 |
| actgctgagg | atcagcgaag | aggtgcaggc | ggagccggat | atcgcggcgg | ccgccaacgc | 720 |
| gaccggacgc | atcggcgaag | gcgcgcccgc | gctctggttt | gacaatatcc | gcggctttac | 780 |
| tgacgcgcgg | gtggcgatga | acaccattgg | ttcatggccg | aaccacgcga | tctcgctcgg | 840 |
| tctgccgcct | gccacaccgg | taaagcagca | gatagaagaa | tttattcgcc | gctgggatac | 900 |
| cttcccggtc | gcgccggaac | gccgcgataa | tccgccatgg | gcggaaaaca | gcgtcgacgg | 960 |
| cgacgacatt | aacctgttcg | acattctgcc | gctgtttcgc | ttaaacgacg | gcgacggcg | 1020 |
| gttctacctt | gataaagcgt | gtgtggtctc | gcgcgatccg | ctcgatcccg | aacacttcgg | 1080 |
| caagcagaat | gtcggcatct | accggatgga | agtgaaaggc | aagcgcaagc | tcgggctgca | 1140 |
| accggtgccg | atgcatgaca | tcgcgctgca | tctgcataag | gccgaagagc | gtggcgagga | 1200 |
| tttgccggtt | gcgattacgc | ttggcaacga | tccgatcatc | acgctgatgg | cgccacgcc | 1260 |
| gctgaaatac | gatcagtcgg | aatatgaaat | ggcgggcgcg | ctgcgcgaaa | gcccgtaccc | 1320 |
| gatagccacc | gcgccgctga | ccggtttcga | cgtgccgtgg | gggtcggaag | tgatccttga | 1380 |
| aggggtgatt | gaaggacgca | agcgcgagat | agaagggccg | ttcggcgagt | ttaccgggca | 1440 |
| ctactccggc | gggcgtaaca | tgaccgtggt | gcgtatcgat | aaagtctctt | atcgcaccaa | 1500 |
| accgattttc | gaatcgctct | atctcggcat | gccgtggacc | gaaatcgact | acctgattgg | 1560 |
| cccggcgacc | tgcgtgccgc | tttaccagca | gcttaaagcg | gagttcccgg | aagtgcaggc | 1620 |
| ggtgaacgcg | atgtataccc | acgggctgct | cgcgattatc | tccaccaaga | aacgctacgg | 1680 |
| cggtttcgcc | cgcgcggtgg | gcctgcgtgc | gatgaccacg | ccgcacgggc | ttggctacgt | 1740 |
| gaagatggtg | attatggtgg | atgaggatgt | cgatccgttc | gatctgccgc | aggtgatgtg | 1800 |
| ggcgctgtcg | tcaaaagtga | acccggcggg | cgatctggtg | cagttgccga | atatgtcggt | 1860 |
| gctggagctt | gatcctggct | caagcccggc | ggggattacc | gacaagctga | ttatcgacgc | 1920 |
| cactacgccg | gttgcgccgg | ataaccgcgg | gcattacagc | cagccggtga | agacctgcc | 1980 |
| ggaaaccccg | cagtgggtag | agaagctgac | cgccatgctg | gctaaccgta | aaaaataagg | 2040 |
| agacgagatg | atttgtccac | gttgtgccga | tgaaaccatc | gaaatcatgg | cgacgtcgcc | 2100 |
| ggtgaaaggc | gtcctggacgg | tgtatcagtg | ccagcattgt | ttgtacacct | ggcgcgacac | 2160 |

```
cgagccgctg cgccgtacca gccgcgagca ttaccccgag gcgttccgga tgacgcaggc    2220
cgatatcgat aacgcgccgg aagtgccaac ggtgccgccg ctgctggcgg atggtaagcg    2280
ttaa                                                                 2284

<210> SEQ ID NO 42
<211> LENGTH: 30
<212> TYPE: DNA
<213> ORGANISM: Artificial sequence
<220> FEATURE:
<223> OTHER INFORMATION: PCR primer

<400> SEQUENCE: 42
ctctcatatg aggctaattg tcggaatgac                                       30

<210> SEQ ID NO 43
<211> LENGTH: 29
<212> TYPE: DNA
<213> ORGANISM: Artificial sequence
<220> FEATURE:
<223> OTHER INFORMATION: PCR primer

<400> SEQUENCE: 43
ctctcatatg ttaacgctta ccatccgcc                                        29

<210> SEQ ID NO 44
<211> LENGTH: 2268
<212> TYPE: DNA
<213> ORGANISM: Escherichia coli

<400> SEQUENCE: 44
atgaaactga tcgtcgggat gacaggggct accggtgcgc tcttggtgt ggcattactg      60 caagcgctgc gggagatgcc gaatgtcgag actcatctgg tgatgtcgaa gtgggcgaaa    120
accaccattg aactggaaac gccttacagc gctcgcgatg ttgctgccct cgcagacttc    180
agccataacc cggcggatca gcggcgatc atctcatccg gttcttttcg taccgacggc    240
atgatcgtta ttccgtgcag tatgaaaacg ctcgccggta tccgcgctgg ttacgccgat    300
ggcctggtag ggcgcgcggc ggacgtcgtg ctcaaagaag gccgcaaact ggtgctggtg    360
ccgcgtgaaa tgccgcttag caccatccat ctcgaaaata tgctcgcact ttcacgcatg    420
ggcgtggcga tggtgccgcc gatgcctgcc ttttataacc atcccgaaac ggtagatgac    480
attgtccacc atgtggtagc ccgcgtgctg gatcaatttg gcctcgaaca tccccacgcc    540
aggcgctggc aagattgcc gcaggcccgg aatttttctc aggagaatga ataatggcat    600
ttgatgattt acgcagcttt ttacaggcgc ttgatgacca cggccagtta ctgaaaatca    660
gcgaagaagt gaacgccgag ccggatctgg cagcagcagc taacgccacc gggcgtatcg    720
gcgacggcgc gcccgcgctg tggtttgata atattcgcgg ctttaccgat gcccgcgtgg    780
cgatgaacac catcggttcc tggcagaacc acgcgatttc cctcggcctg ccgccaaatg    840
ccccggttaa aaagcagatt gatgagttta tccgccgctg ggataacttc ccgattgccc    900
cggagcgccg cgccaatcca gcctgggcgc agaacaccgt tgatggcgac gagatcaacc    960
tgttcgatat cctgccgctg tttcgtttaa acgatggcga tggcggtttc tatctcgaca   1020
aagcgtgcgt ggtttcccgc gatccgctcg accggataa cttcggcaag cagaacgtcg   1080
gcatctaccg catggaagtg aagggcaagc gtaagctcgg cctgcaaccg gtgccgatgc   1140
acgatatcgc cctgcatctg cataaagcag aagagcgcgg tgaagatctg ccgattgcga   1200
```

```
tcacgctcgg taacgatccg atcatcacgc tgatggggc cacgccgctg aaatatgatc      1260
agtccgagta cgaaatggca ggcgcgctgc gtgaaagccc gtacccgatc gccaccgccc      1320
cgttgaccgg ttttgatgtg ccgtggggtt cagaagtgat cctcgaaggg gtcatcgaaa      1380
gccgtaaacg cgaaatcgaa gggccgttcg gtgagtttac cggcactac tccggcgggc      1440 gtaacatgac cgtggtgcgc atcgataaag tctcttaccg caccaggccg attttcgaat      1500
cgctgtacct cggtatgccg tggaccgaaa tcgactacct gatggggcca gccacctgcg      1560
tgccgctgta tcagcagctg aaagccgagt ccctgaagt gcaggcggta acgccatgt       1620 acacccatgg cctgctggcg attatctcca ccaaaaaacg ctacggcggc tttgcccgcg      1680
cggtgggcct gcgcgcaatg accacgccgc atggtctggg ctacgtgaag atggtgatta     1740
tggtcgatga agacgttgac ccgttcaacc tgccgcaggt gatgtgggcg ctctcctcga     1800
aagtgaaccc ggcaggggat ttggtgcagt tgccgaatat gtccgtgctg gaactcgatc     1860
caggctcaag ccctgcgggg atcaccgaca agctgattat cgacgccact acgcctgtcg     1920
ccccggacaa ccgtggtcac tacagccaac cggtggtgga tttaccggaa accaaagcct     1980
gggctgaaaa actgaccgct atgctggctg cacgtaaata aggagaagaa gatgatttgt     2040
ccacgttgtg ccgatgaaca gattgaagtg atggcgaaat cgccggtgaa agatgtctgg    2100
acggtatatc agtgccagca ttgcctttat acctggcgcg ataccgaacc gctgcgccgt    2160
accagccgcg aacattatcc cgaagcgttc cgcatgacgc agaaagatat tgatgacgcg    2220
ccaatggtgc cgagcatccc gccgctgctg gtggaaggta agcgctaa                 2268

<210> SEQ ID NO 45
<211> LENGTH: 28
<212> TYPE: DNA
<213> ORGANISM: Artificial sequence
<220> FEATURE:
<223> OTHER INFORMATION: PCR primer

<400> SEQUENCE: 45
ctctcatatg aaactgatcg tcgggatg                                         28

<210> SEQ ID NO 46
<211> LENGTH: 28
<212> TYPE: DNA
<213> ORGANISM: Artificial sequence
<220> FEATURE:
<223> OTHER INFORMATION: PCR primer

<400> SEQUENCE: 46
ctctcatatg ttagcgctta ccttccgc                                         28

<210> SEQ ID NO 47
<211> LENGTH: 2268
<212> TYPE: DNA
<213> ORGANISM: Escherichia fergusonii

<400> SEQUENCE: 47
atgagactga tcgtcgggat gacagggcc accggagcgc tcttggtgt ggcattactg        60 caagcgctgc gggagatgcc gaatgtcgag actcatctgg tgatgtcgaa gtgggcgaaa    120
accaccattg aactggaaac gccttacaac gcccgcgatg ttgctgccct cgcagacttc    180
tgccataacc cggcggatca ggccgcaacc atctcctcag gttcctttcg taccgacggt    240
atgatcgtta ttccgtgcag tatgaaaacg ctcgccggta tccgcgctgg ttacgccgat    300
ggcctggtag ggcgcgcggc ggacgtcgtg ctcaaagaag gccgcaaact ggtgctggtg    360
```

```
ccgcgtgaaa tgccgcttag caccatccat ctcgaaaata tgctcgcact ttcgcgcatg    420
ggcgtggcga tggtgccgcc gatgcctgcc ttttataacc atcccgaaac ggtagatgac    480
attgtccacc acgtggtagc ccgcgtgctg gatcaatttg gcctcgaaca tcctcacgcc    540
aggcgctggc aaggattgcc gcaggcccgg aattttccc aggagaatga ataatggcat    600
ttgatgattt acgcagcttt ttacaggcgc ttgatgacta cggtcagtta ctgaaaatca    660
gtgaagaagt gaacgccgag ccggatctgg cagccgctgc caacgccacc gggcgtatcg    720
gcgacggtgc accggcgctg tggtttgaca atattcgcgg ctttaccgat gcccgcgtgg    780
caatgaacac catcggctcc tggcagaacc acgcgatttc cctcggcctg ccgccaaaca    840
ccccggttaa aaacagatt gatgagttta ccgccgctg gataacttt cccattgccc        900 cggagcgccg tgcgaatccg gtctgggcg agaacaccgt cgatggcgac gagattaatt    960
tgttcgatat tctgccgctg tttcgtttaa cgatggcga tggcggtttc tatctcgaca    1020
aagcgtgcgt ggtttcccgc gatccgctcg accggataa tttcggcaag cagaatgtcg    1080
gcatctaccg catggaagtg aagggcaagc gtaagctcgg cctgcaaccg gtgccgatgc    1140
acgatatcgc cctgcatctg cataaagcag aagagcgcgg tgaagatctg ccgattgcga    1200
tcacgctcgg taacgatccg atcatcaccc tgatggggc caccccgctg aaatacgatc    1260
aatcagagta cgaaatggct ggcgcactac gcgaaagccc gtaccgatc gccaccgccc      1320 cgctgaccgg ttttgatgtg ccgtggggct cagaagtgat cctcgaaggc gttatcgaaa    1380
gccgtaaacg cgagattgaa gggccgttcg gtgaatttac cggccactac tccggcgggc    1440
gcaacatgac cgtagtgcgc atcgataaag tctcttaccg caccaaaccg attttgaat    1500 cgctctatct cggtatgccg tggaccgaaa tcgactacct gatggggcca gccacctgtg    1560
tgccgctgta tcagcaactg aaagccgagt tcccggaagt gcaggcggtg aacgccatgt    1620
acacccacgg cctgctggcg attatctcca ccaaaaaacg ctacggcggc tttgcccgcg    1680
cggtgggcct gcgtgcgatg accacgccgc acggtctggg ctacgtgaag atggtgatta    1740
tggtcgatga agacgttgat ccgttcaacc tgccgcaggt gatgtgggcg ctttcgtcga    1800
aagtgaaccc ggcaggggat ctggtgcagt tgccgaatat gtcagtactg gaactcgacc    1860
ctggctcaag cccggcgggg atcaccgata agctgattat cgacgccact acgcctgtcg    1920
ccccggacaa ccgtggtcac tacagccagc cggtggtgga cttaccggaa accaaagcct    1980
gggctgaaaa actgaccgct atgctggccg cacgtaaata aggagaacaa gatgatttgt    2040
ccacgttgtg ccgatgaaca gattgaagtg atggcgaaat cgccggtgaa agatgtctgg    2100
acggtctacc agtgccagca ttgccttat acctggcgcg atactgaacc gctacgccgc    2160
accagccgcg aacattaccc gcaagcgttc cgtatgactc aaaaagatat tgatgacgcg    2220
ccaatggtgc cgagcattcc gccgctgctg gcggcagata agcgctaa                 2268
```

<210> SEQ ID NO 48
<211> LENGTH: 27
<212> TYPE: DNA
<213> ORGANISM: Artificial sequence
<220> FEATURE:
<223> OTHER INFORMATION: PCR primer

<400> SEQUENCE: 48
ctctcatatg agactgatcg tcgggat                                         27

<210> SEQ ID NO 49

```
<211> LENGTH: 28
<212> TYPE: DNA
<213> ORGANISM: Artificial sequence
<220> FEATURE:
<223> OTHER INFORMATION: PCR primer

<400> SEQUENCE: 49
ctctcatatg ttagcgctta tctgccgc                                              28

<210> SEQ ID NO 50
<211> LENGTH: 2304
<212> TYPE: DNA
<213> ORGANISM: Paenibacillus polymyxa

<400> SEQUENCE: 50
atgaagaaaa tcattgtagg aatatcggga gcgacagggt caatctttgg tatccgtata           60
ttgcaaaaat tacgggaggc tggagtccaa agccatctgg tgctatcccc gtgggctatt          120
gccaacattc cctatgagac aggctacacg gtgaaggatg tgaaggcaat ggcggatgca          180
gtctactcgt ataaggatca ggccgcacgt atttctagcg gctccttccg ggtagatggt          240
atggtcgtcg ctccttgcag tatgaagact cttgcctcta ttcgtatcgg tatggcggac          300
aacctgctta cccgatcagc ggatgtgata ctgaaggagc gaaagaagct gctgctcatg          360
accagagaaa caccattaag cagtatccat ctggaaaata tgctggagct gtcacgtatg          420
ggcgtgatga tcctgccgcc gatgcctgcc ttttataatc atcctgcaag tatcgaggaa          480
ttagtggatc atattgtttt tcgcgcattg gatcagttcg gtattgtcac aaccgcagcc          540
aaacgctggg atgggatgaa gcagaatgac tccaggctgc accagaattg agaaatcgaa          600
agacgaagga gaatgaatga tggcttataa agactttcgc gattttctac acaccttgga          660
aaaggaggga caattactca cgatcagcga tgaggtaaag ccggagccgg acctcgcagc          720
agctaacaga gcattaaaca atcttggaga taagacgcct gctctctttt tcaacaacat          780
ctatggatat acgatgctc gtattgcaat gaatgtgatg ggctcctggc ccaatcatgc          840
cctcatgatg ggaatgccca aaaatacgcc gctcaaggag cagttttttg aatttgccag          900
acgctatgaa caatttccgg tgcccgtgaa gcgggaagaa gccgctccct ttcatgaagt          960
cgaaattacg gagaatatta atttgttttga tattttgccg ttgtttcgtt tgaatcaggg         1020
ggacggaggg ttttatttgg ataaaagcaat tctaatttca cgcgatctgg atgacccgga         1080
cacctacggt aagcaaaatg tcggcttata ccggatgcag gtgaaaggca agaaccgttt         1140
gggcatccag cctgtaccac agcatgatat tgcgatccat atccgtcagg ctgaggagcg         1200
tggcgaaaat ctgaaggtgg ctattgccct cggatgtgag cctgtgatta caacggctgc         1260
ttctacgcca ctgctgtacg atcaatccga atatgagatg gcgggcgcca ttcagggcga         1320
gccttatcgt gtggtcaaag cgaaggatgc agatctggat ctgccttggg gagccgaggt         1380
cattttggaa ggcgaagtgt tagcaggtga acgtgagtat gaaggtccat tcggtgaatt         1440
cacaggtcac tattccggcg gtcgcgcgat gccagtcatt cagattaatc gtgtatatca         1500
ccgcaaacag cctatctttg agcatctgta catcggatg ccttggacgg aaacggatta         1560
tatgatcggt gtgaatacaa gtgtaccgtt gtttcagcag cttaaggatg cttttcctaa         1620
tgaaatcgta gctgttaatg ccatgtatac gcatgggctg gtcgctatta tttccacgaa         1680
aacccggtat ggcggctttg cgaaggctgt gggaatgcgt gcgttaacga ctccgcatgg         1740 attgggggtat tgcaagctgg tgattgtggt ggacgaggag gtcgatccgt tcaatctgcc         1800
gcaagtcatg tgggctttat ccaccaagct tcatccaaag catgatgctg tcattgttcc         1860
```

```
tggcttgtct attttaccgc ttgaccccgg ctctgatccg gcaggtatga cgcacaaaat    1920
gatactggat gcgacgacac ctgtagcacc ggatattaga ggccattact cgcagccgct    1980
cgattccccg ctgggtgtag cggaatggga gaaaaagttg agccaaatgc ttcgctaaat    2040
atttttaaaa acaaagaaaa tttaaaggag tgctgacaga tgcatatttg tccccgttgt    2100
gagtccaatc gttcagaagt cgtttcccat tcgccggtta aggtgcctg ggaggttttg     2160 ttgtgccctg tatgcctgtt cacatggcga acctcagaac cggatagcat tactgatcca    2220
gcaaagtata aatcggcgtt caaggtaaac ccccaagata ttccggatgc tgctcatgtt    2280
cctcctattc cagagcggat atag                                           2304
```

<210> SEQ ID NO 51
<211> LENGTH: 35
<212> TYPE: DNA
<213> ORGANISM: Artificial sequence
<220> FEATURE:
<223> OTHER INFORMATION: PCR primer

<400> SEQUENCE: 51

```
ctctcatatg aagaaaatca ttgtaggaat atcgg                                35
```

<210> SEQ ID NO 52
<211> LENGTH: 31
<212> TYPE: DNA
<213> ORGANISM: Artificial sequence
<220> FEATURE:
<223> OTHER INFORMATION: PCR primer

<400> SEQUENCE: 52

```
ctctcatatg ctatatccgc tctggaatag g                                    31
```

<210> SEQ ID NO 53
<211> LENGTH: 2318
<212> TYPE: DNA
<213> ORGANISM: Pantoea ananatis

<400> SEQUENCE: 53

```
atgagtagat tactgttaat ttcattcgta cacgaacgtt atttgcaagg aagtcagatg      60
agaattgtaa tcggtatgac gggagcaaca ggtgcccctt taggggtggc tctgctcagc     120
attttgcagg aaatcaaaga ggttgaaact catctgattt tgagcaagtg gctaaaacc      180 acaattgaac tcgaaacgcc ttttcatcg cgtgaggtga tgagcatggc tgatgttgtg      240 tatgcccgt ccgaccaggc cgctactctc tcgtcaggtt cttttcacac cgatgggatg      300
gtcattattc cttgcagtat gaaaaccta gcgggaattc gcatgggata cgcggaaggc      360
cttattggac gggctgctga tgtcgtcatt aaagaaggca gaaaacttgt gctggtcccc     420
agagagacgc ctctcagcac cattcacctg gaaaatatgc tagccctttc ccgtcttggc     480
gtatccatgg ttccgcccat gcccgctttt tataaccacc ccgcagtaat tgatgatgtg     540
atcgatcatg tcgttttctcg tgttctcgac cagtttggga ttgcctcgcc aaaggcaaat     600
cgctggaaag gcctgaacaa ttctaagaaa tccctgagta tggagagtaa ataatggctt     660
ttgatgacct acgtagcttc cttaaggctc tggacgagca gggggcagctt cttgagattg    720 atgaagaggt tttaccccgaa cctgatattg ccgcggccgc taatgctaca ggccgaattg    780
gtgaaggtgc accggcaatc tcattcaaaa aaataaaggg gttcaatcat gctcatgttg    840
tgatgaacac tattggttcc tggcaaaaacc atgcaattc actgggcctc ccaatgaata    900
```

| | |
|---|---|
| ccccagtgaa acagcagata gatgaattca ttcgtcgctg ggacactttt cctgtggcac | 960 |
| cagagcggcg cgacaatgcg ccctggtcag aaaataccgt tgattgtgaa gagatcaatc | 1020 |
| tcttcgacat ccttcccctg ttccgcctga acgacggcga cggcggtttc tatcttgata | 1080 |
| aggcctgcgt agtatcacgt gacccgcttg atccagaaca tttcggtaag caaaacgtcg | 1140 |
| gcatttaccg gatggaggtg aaaggtaaac gtaaactcgg gctccagccc gtgccgatgc | 1200 |
| atgacattgc acttcatctc cataaggccg aagaacgcgg cgacgatctg ccagtggcta | 1260 |
| ttacgctggg caatgacccc attattacat tgatgggcgc cacgccgctg aaatacgacc | 1320 |
| agtcagaata tgagatggca ggtgcgctgc gtgaaagccc gtaccccatc gcctccgcgc | 1380 |
| ctctgaccgg ctttgatgtg ccgtggggat cggaagtcat tcttgaaggc gtgatagaag | 1440 |
| ggcgcaaacg tgagattgaa ggaccgtttg gcgaattcac cggccattat tccggcggtc | 1500 |
| gcaatatgac cgttgtgcgg attgataagg tctcctaccg cactaagcca atattcgagt | 1560 |
| cattgtatct gggaatgccc tggaccgaaa ttgattatct gatgggcccg gcaacctgtg | 1620 |
| tcccttttgta tcaacagctg aaagcggatt ccctgaggt gcaggctgta aatgcaatgt | 1680 |
| atacacacgg attactggcc attatttcta caaagaaacg ttatggtgga tttgcccgtg | 1740 |
| ctgtaggcgt acgggcgatg acaaccccgc atggtctggg ctacgtcaag atggtgatca | 1800 |
| tggtcgatga ggatgtcgat ccctttaacc tgcctcaggt gatgtgggcg ctgtcttcaa | 1860 |
| aggtcaatcc gcaaggcgat ctcgttcaac tgccaaacat gtccgtactg gaactggacc | 1920 |
| cgggttccag ccctgcggga atcacggata aacttgtgat cgatgcgacg actcccgtgg | 1980 |
| caccggatac ccgcggccac tacagtcagc cggtaaaaga cctgccagaa acttcaatct | 2040 |
| gggttgagaa gttaacgtcc ctgttatcaa atcgcggtta aggagaaagt atgatttgtc | 2100 |
| cacgttgtgc tgatgaacac attgaaatca tggcaacatc cccagttgag gggatatgga | 2160 |
| cggtgcatca gtgtcagcat tgcctgtaca catggcgcaa tacagagcca gcccgaagaa | 2220 |
| cggagcggga acattatcct gaagccttcc ggatgactca acgtgatatt gataatgcgc | 2280 |
| cggaagtccc gtctgtccct cctctgttag ctaagtaa | 2318 |

<210> SEQ ID NO 54
<211> LENGTH: 38
<212> TYPE: DNA
<213> ORGANISM: Artificial sequence
<220> FEATURE:
<223> OTHER INFORMATION: PCR primer

<400> SEQUENCE: 54
ctctcatatg agtagattac tgttaatttc attcgtac                          38

<210> SEQ ID NO 55
<211> LENGTH: 32
<212> TYPE: DNA
<213> ORGANISM: Artificial sequence
<220> FEATURE:
<223> OTHER INFORMATION: PCR primer

<400> SEQUENCE: 55
ctctcatatg ttacttagct aacagaggag gg                                32

<210> SEQ ID NO 56
<211> LENGTH: 30
<212> TYPE: DNA
<213> ORGANISM: Artificial sequence
<220> FEATURE:
<223> OTHER INFORMATION: PCR primer -continued

```
<400> SEQUENCE: 56
ctcttctaga gaaacgatca agtgcaccag                                          30

<210> SEQ ID NO 57
<211> LENGTH: 40
<212> TYPE: DNA
<213> ORGANISM: Artificial sequence
<220> FEATURE:
<223> OTHER INFORMATION: PCR primer

<400> SEQUENCE: 57
gacacgagcg tttatacctc taattgccac tggtacgtgg                               40

<210> SEQ ID NO 58
<211> LENGTH: 20
<212> TYPE: DNA
<213> ORGANISM: Artificial sequence
<220> FEATURE:
<223> OTHER INFORMATION: PCR primer

<400> SEQUENCE: 58
gaggtataaa cgctcgtgtc                                                     20

<210> SEQ ID NO 59
<211> LENGTH: 30
<212> TYPE: DNA
<213> ORGANISM: Artificial sequence
<220> FEATURE:
<223> OTHER INFORMATION: PCR primer

<400> SEQUENCE: 59
ctctgagctc gagaacacga accatacgag                                          30
```

US 9,090,900 B2

CORYNEFORM BACTERIUM TRANSFORMANT AND PROCESS FOR PRODUCING PHENOL USING THE SAME

TECHNICAL FIELD

The present invention relates to a technique for producing phenol. In more detail, the present invention relates to a *Corynebacterium glutamicum* transformant constructed by specific gene recombination and thereby provided with a phenol producing function, and relates to an efficient phenol producing process using the transformant.

BACKGROUND ART

Against the backdrop of global warming and exhaustion of fossil resources, production of chemical products using renewable resources, along with production of biofuels, is recognized as an emerging industry, biorefinery, which is an important means for realizing a low-carbon society, and has attracted keen attention.

However, production of biophenol using renewable resources is less productive as compared to production of lactic acid or ethanol because the metabolic reaction from a raw material saccharide consists of a great many steps. In addition, for the reasons that produced phenol inhibits bacterial proliferation and that phenol is cytotoxic, industrial production of phenol has been considered to be impossible.

Important use of phenol is phenol resins. A phenol resin, which is produced by addition condensation of phenol and aldehyde, is one of the oldest plastics, and with its properties including excellent heat resistance and durability, is used for various purposes, such as an alternative automotive material to metal, a semiconductor seal material, and a circuit board even today. Due to extremely high reactivity of phenol and aldehyde as raw materials and to the complicated three-dimensional network structure of resulting phenol resin polymers, precise structural designing and development into nanomaterials thereof had been considered difficult and so had been application to high-value-added use. However, in recent years, the theory of physical-properties of polymers and the simulation thereof have rapidly developed, and therefore it has gradually become possible to create highly functional materials from phenol resins by refining the network structure. Under the circumstances, the phenol resin production in Japan is also increasing year by year.

The currently employed industrial production process of phenol (cumene process) is a typical energy-consumptive process in the chemical industry using petroleum-derived benzene and propylene as raw materials, and requiring great amounts of solvent and thermal energy. Therefore, in the light of global environment conservation and greenhouse gas reduction, there is an urgent need to develop an environment-conscious, energy saving process that allows production of phenol from renewable resources and can reduce carbon dioxide emissions and waste products, that is, to establish biophenol production technologies.

No phenol-producing bacteria in nature have been reported so far.

Regarding known phenol producing technologies using recombinant bacteria, Non Patent Literature 1 discloses a technology in which 2 mM 4-hydroxybenzoate is completely converted to phenol within 50 hours with the use of a cell suspension or a cell extract of *Clostridium hydroxybenzoicum*.

In addition, Patent literature 1 discloses a technology in which phenol is produced from 4-hydroxybenzoate with the use of a transformant constructed with a 4-hydroxybenzoate decarboxylase gene derived from *Enterobacter cloacae*.

However, practically efficient phenol production cannot be achieved by the process of Non Patent Literature 1 or Patent Literature 1.

CITATION LIST

Patent Literature

[PTL 1] JP 2006-050914 A

Non Patent Literature

[NPL 1] International Journal of Systematic and Evolutionary Microbiology, Vol. 52, 2002, 801-807

SUMMARY OF INVENTION

Technical Problem

An object of the present invention is to provide a microorganism capable of efficiently producing phenol from 4-hydroxybenzoate, and a process for efficiently producing phenol from 4-hydroxybenzoate.

Solution to Problem

The present inventors have wholeheartedly carried out investigations in order to achieve the object described above and obtained the following findings.

(i) A transformant constructed by transferring a 4-hydroxybenzoate decarboxylase gene into a *Corynebacterium glutamicum* can efficiently produce phenol from 4-hydroxybenzoate.

(ii) The transformant can further efficiently produce phenol in the case where the phenol 2-monooxygenase gene on the chromosome of the *Corynebacterium glutamicum* as the host has a disruption or deletion.

(iii) The transformant has a particularly higher phenol productivity when proliferation is substantially inhibited in a reaction mixture under reducing conditions.

The present invention, which has been completed based on the above-mentioned findings, provides the following transformant and process for producing phenol.

[1] A phenol-producing transformant constructed by transferring a gene which encodes an enzyme having 4-hydroxybenzoate decarboxylase activity into *Corynebacterium glutamicum* as a host.

[2] The transformant of the above [1], wherein the gene which encodes an enzyme having 4-hydroxybenzoate decarboxylase activity is a gene derived from *Bacillus subtilis, Bacillus atrophaeus, Bacillus subtilis* subsp. spizizenii, *Citrobacter koseri, Enterobacter aerogenes, Enterobacter cloacae, Enterobacter hormaechei, Enterobacter sakazakii, Escherichia coli, Escherichia fergusonii, Paenibacillus polymyxa*, or *Pantoea ananatis*.

[3] The transformant of the above [1], wherein the gene which encodes an enzyme having 4-hydroxybenzoate decarboxylase activity is the DNA of the following (a) or (b).

(a) a DNA consisting of the base sequence of SEQ ID NO: 16, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, NO: 47, SEQ ID NO: 50, or SEQ ID NO: 53

(b) a DNA which hybridizes to a DNA consisting of a complementary base sequence of any of the DNAs of (a) under stringent conditions and which encodes a polypeptide having 4-hydroxybenzoate decarboxylase activity

[4] The transformant of any one of the above [1] to [3], wherein the *Corynebacterium glutamicum* as the host is a strain of *Corynebacterium glutamicum* in which a gene which encodes an enzyme having phenol 2-monooxygenase activity on the chromosome is disrupted or deleted.

[5] The transformant of any one of the above [1] to [4], wherein the *Corynebacterium glutamicum* as the host is a strain of *Corynebacterium glutamicum* in which a gene which encodes an enzyme having 4-hydroxybenzoate hydroxylase activity on the chromosome is disrupted or deleted.

[6] The transformant of any one of the above [1] to [3], wherein the *Corynebacterium glutamicum* as the host is *Corynebacterium glutamicum* R (FERM BP-18976), ATCC13032, or ATCC13869.

[7] The transformant of any one of the above [1] to [3], wherein the *Corynebacterium glutamicum* as the host is a strain of *Corynebacterium glutamicum* R (FERM BP-18976), ATCC13032, or ATCC13869 in which a gene which encodes an enzyme having phenol 2-monooxygenase activity on the chromosome is disrupted or deleted.

[8] The transformant of any one of the above [1] to [3], wherein the *Corynebacterium glutamicum* as the host is a strain of *Corynebacterium glutamicum* R (FERM BP-18976), ATCC13032, or ATCC13869 in which a gene which encodes an enzyme having 4-hydroxybenzoate hydroxylase activity on the chromosome is disrupted or deleted.

[9] *Corynebacterium glutamicum* transformant PHE21 (Accession Number: NITE BP-996), PHE21-2, PHE21-3, PHE21-4, PHE21-5, PHE21-6, PHE21-7, PHE21-8, PHE21-9, PHE21-10, PHE21-11, PHE21-12, PHE22-1, PHE22-2, PHE22-3, PHE22-4, PHE22-5, PHE22-6, PHE22-7, PHE22-8, PHE22-9, PHE22-10, PHE22-11, PHE22-12, PHE23-1, PHE23-2, PHE23-3, PHE23-4, PHE23-5, PHE23-6, PHE23-7, PHE23-8, PHE23-9, PHE23-10, PHE23-11, or PHE23-12.

[10] A process for producing phenol, which comprises a step of allowing the transformant of any one of the above [1] to [9] to react in a reaction mixture containing 4-hydroxybenzoate or a salt thereof under reducing conditions, and a step of collecting phenol from the reaction mixture.

[11] The process of the above [10], wherein the transformant does not substantially proliferate in the reaction step.

[12] The process of the above [10] or [11], wherein the oxidation-reduction potential of the reaction mixture under reducing conditions is −200 mV to −500 mV.

Advantageous Effects of Invention

With the use of the transformant of the present invention, phenol can be efficiently produced from 4-hydroxybenzoate.

Generally, growth of microorganisms is inhibited by a solvent, such as a phenol, because of its cytotoxicity, and therefore phenol production with the use of microorganisms was difficult. According to the process of the present invention, however, phenol production with the use of microorganisms can be achieved with a practically sufficient efficiency.

DESCRIPTION OF EMBODIMENTS

Figure 1:
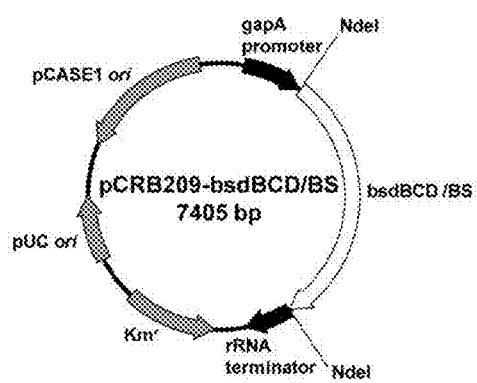
FIG. 1 shows the construct of a plasmid used in Examples.

Hereinafter, the present invention will be described in detail.

(I) Phenol-producing Transformant

The transformant of the present invention capable of producing phenol is a transformant constructed by transferring a gene which encodes an enzyme having 4-hydroxybenzoate decarboxylase activity into *Corynebacterium glutamicum* as a host.

Host

The *Corynebacterium glutamicum* used as a host is a group of microorganisms defined in Bergey's Manual of Determinative Bacteriology, Vol. 8, 599 (1974).

Specific examples of the strains thereof include *Corynebacterium glutamicum* R (FERM P-18976), ATCC13032, ATCC13869, ATCC13058, ATCC13059, ATCC13060, ATCC13232, ATCC13286, ATCC13287, ATCC13655, ATCC13745, ATCC13746, ATCC13761, ATCC14020, ATCC31831, MJ-233 (FERM BP-1497), and MJ-233AB-41 (FERM BP-1498). Inter alia, preferred strains are R (FERM P-18976), ATCC13032, and ATCC13869, and more preferred is R (FERM P-18976).

According to molecular biological classification, names of some species of coryneform bacteria, such as *Brevibacterium flavum*, *Brevibacterium lactofermentum*, *Brevibacterium divaricatum*, and *Corynebacterium lilium* are standardized to *Corynebacterium glutamicum* (Liebl, W. et al., Transfer of *Brevibacterium divaricatum* DSM 20297T, "*Brevibacterium flavum*" DSM 20411, "*Brevibacterium lactofermentum*" DSM 20412 and DSM 1412, and *Corynebacterium glutamicum* and their distinction by rRNA gene restriction patterns. Int. J. Syst. Bacteriol. 41: 255-260. (1991); and Kazuo Komagata et al., "Classification of the coryneform group of bacteria", Fermentation and industry, 45: 944-963 (1987)), and therefore, these are all included in the present invention.

The *Corynebacterium glutamicum* may be, let alone a wild strain, a mutant thereof or an artificial recombinant thereof. Examples thereof include disruptants in which a gene of lactate dehydrogenase, phosphoenolpyruvate carboxylase, or malate dehydrogenase is disrupted. Using such a disruptant as a host can improve phenol productivity and reduce production of by-products.

Inter alia, preferred is a disruptant in which a lactate dehydrogenase gene is disrupted. In the disruptant, the lactate dehydrogenase gene is disrupted and the metabolic pathway from pyruvic acid to lactic acid is blocked. Inter alia, especially preferred is a disruptant of *Corynebacterium glutamicum* R (FERM P-18976) strain in which the lactate dehydrogenase gene is disrupted.

Such a disruptant can be prepared based on a conventional gene engineering process. Such a lactate dehydrogenase disruptant and the preparation process thereof are described in WO 2005/010182 A1.

4-Hydroxybenzoate decarboxylase Gene (bsdBCD or dca)

4-Hydroxybenzoate decarboxylase is an enzyme that catalyzes a phenol-producing reaction in which 4-hydroxybenzoate is decarboxylated.

The gene which encodes an enzyme having 4-hydroxybenzoate decarboxylase activity may be of any origin without particular limitation, and examples thereof include genes derived from members of the genus *Bacillus*, such as *Bacillus subtilis*, *Bacillus megaterium*, *Bacillus licheniformis*, *Bacillus atrophaeus*, and *Bacillus subtilis* subsp. spizizenii; members of the genus *Citrobacter*, such as *Citrobacter koseri*; members of the genus *Enterobacter*, such as *Enterobacter* aerogenes, Enterobacter cloacae, Enterobacter hormaechei, and Enterobacter sakazakii; members of the genus Escherichia, such as Escherichia coli and Escherichia fergusonii; members of the genus Paenibacillus, such as Paenibacillus polymyxa; and members of the genus Pantoea, such as Pantoea ananatis. Inter alia, preferred is a gene derived from Bacillus, in particular Bacillus subtilis; Enterobacter, in particular Enterobacter cloacae; or Escherichia, in particular Escherichia coli.

A gene which encodes an enzyme having 4-hydroxybenzoate decarboxylase activity is called by an abbreviated name that varies according to the origin. For example, a 4-hydroxybenzoate decarboxylase gene derived from Bacillus subtilis is called by an abbreviation bsdBCD. Herein, a 4-hydroxybenzoate decarboxylase gene may be called by an abbreviation "dca" regardless of the origin.

Examples of the 4-hydroxybenzoate decarboxylase gene derived from Bacillus subtilis include the DNA consisting of the base sequence of SEQ ID NO: 16, examples of the 4-hydroxybenzoate decarboxylase gene derived from Bacillus atrophaeus include the DNA consisting of the base sequence of SEQ ID NO: 23, examples of the 4-hydroxybenzoate decarboxylase gene derived from Bacillus subtilis subsp. spizizenii include the DNA consisting of the base sequence of SEQ ID NO: 26, examples of the 4-hydroxybenzoate decarboxylase gene derived from Citrobacter koseri include the DNA consisting of the base sequence of SEQ ID NO: 29, examples of the 4-hydroxybenzoate decarboxylase gene derived from Enterobacter aerogenes include the DNA consisting of the base sequence of SEQ ID NO: 32, examples of the 4-hydroxybenzoate decarboxylase gene derived from Enterobacter cloacae include the DNA consisting of the base sequence of SEQ ID NO: 35, examples of the 4-hydroxybenzoate decarboxylase gene derived from Enterobacter hormaechei include the DNA consisting of the base sequence of SEQ ID NO: 38, examples of the 4-hydroxybenzoate decarboxylase gene derived from Enterobacter sakazakii include the DNA consisting of the base sequence of SEQ ID NO: 41, examples of the 4-hydroxybenzoate decarboxylase gene derived from Escherichia coli include the DNA consisting of the base sequence of SEQ ID NO: 44, examples of the 4-hydroxybenzoate decarboxylase gene derived from Escherichia fergusonii include the DNA consisting of the base sequence of SEQ ID NO: 47, examples of the 4-hydroxybenzoate decarboxylase gene derived from Paenibacillus polymyxa include the DNA consisting of the base sequence of SEQ ID NO: 50, and examples of the 4-hydroxybenzoate decarboxylase gene derived from Pantoea ananatis include the DNA consisting of the base sequence of SEQ ID NO: 53.

In the present invention, a DNA which hybridizes to a DNA consisting of a complementary base sequence of the base sequence of SEQ ID NO: 16, 23, 26, 29, 32, 35, 38, 41, 44, 47, 50, or 53 under stringent conditions and which encodes a polypeptide having 4-hydroxybenzoate decarboxylase activity can also be used.

The "stringent conditions" as used herein means general conditions, for example, the conditions described in Molecular Cloning, A Laboratory Manual, Second edition, 1989, Vol. 2, p. 11. 45. It means, in particular, conditions where hybridization occurs at a temperature 5 to 10° C. below the melting temperature (Tm) of a perfect hybrid.

The 4-hydroxybenzoate decarboxylase activity can be measured by the method described in Genomics, 86, 342-351 (2005) "Materials and Methods". Briefly, by adding a test enzyme to a liquid for testing, a reaction mixture containing 100 mM MES (pH 6.0), 1 mM DTT, 5 mM 4-hydroxybenzoate, and the enzyme is prepared, and then the slope of the absorbance at 270 nm (initial rate) is determined. The same measurement is performed using a system without the addition of 4-hydroxybenzoate to obtain a background value. The difference between the two measured values will be regarded as the 4-hydroxybenzoate decarboxylase activity.

In the present invention, a DNA consisting of a base sequence which has 90% or more, preferably 95% or more, more preferably 98% or more homology with the base sequence of SEQ ID NO: 16, 23, 26, 29, 32, 35, 38, 41, 44, 47, 50, or 53 and which encodes a polypeptide having 4-hydroxybenzoate decarboxylase activity can also be used.

The base sequence homology was calculated using GENETYX Ver. 8 (made by Genetyx).

The homologue of the DNA consisting of the base sequence of SEQ ID NO: 16, 23, 26, 29, 32, 35, 38, 41, 44, 47, 50, or 53 can be selected from a DNA library of a different species by, for example, PCR or hybridization using a primer or a probe designed based on these base sequences, according to a conventional method, and as a result, a DNA which encodes a polypeptide having 4-hydroxybenzoate decarboxylase activity can be obtained with a high probability.

Construction of Vector for Transformation

The DNA which encodes 4-hydroxybenzoate decarboxylase is amplified by PCR and then cloned into a suitable vector which is replicable in a host.

The plasmid vector may be any plasmid vector as long as it comprises a gene responsible for autonomously replicating function in Corynebacterium glutamicum. Specific examples of the plasmid vector include pAM330 derived from Brevibacterium lactofermentum 2256 (JP 58-67699 A; Miwa, K. et al., Cryptic plasmids in glutamic acid-producing bacteria. Agric. Biol. Chem. 48:2901-2903 (1984); and Yamaguchi, R. et al., Determination of the complete nucleotide sequence of the Brevibacterium lactofermentum plasmid pAM330 and the analysis of its genetic information. Nucleic Acids Symp. Ser. 16:265-267 (1985)); pHM1519 derived from Corynebacterium glutamicum ATCC13058 (Miwa, K. et al., Cryptic plasmids in glutamic acid-producing bacteria. Agric. Biol. Chem. 48:2901-2903 (1984)) and pCRY30 derived from the same (Kurusu, Y. et al., Identification of plasmid partition function in coryneform bacteria. Appl. Environ. Microbiol. 57:759-764 (1991)); pCG4 derived from Corynebacterium glutamicum T250 (JP 57-183799 A; and Katsumata, R. et al., Protoplast transformation of glutamate-producing bacteria with plasmid DNA. J. Bacteriol., 159:306-311 (1984)), pAG1, pAG3, pAG14 and pAG50 derived from the same (JP 62-166890 A), and pEK0, pEC5 and pEKEx1 derived from the same (Eikmanns, B. J. et al., A family of Corynebacterium glutamicum/Escherichia coli shuttle vectors for cloning, controlled gene expression, and promoter probing. Gene, 102: 93-98 (1991)); etc.

Examples of a preferred promoter include promoter PgapA as a promoter of the glyceraldehyde-3-phosphate dehydrogenase A gene (gapA), promoter Pmdh as a promoter of the malate dehydrogenase gene (mdh), and promoter PldhA as a promoter of lactate dehydrogenase A gene (ldhA), all of which are derived from Corynebacterium glutamicum R, and inter alia, PgapA is preferred.

Examples of a preferred terminator include terminator rrnB T1T2 of Escherichia coli rRNA operon, terminator trpA of Escherichia coli, and terminator trp of Brevibacterium lactofermentum, and inter alia, terminator rrnB T1T2 is preferred.

Transformation

As a method of transformation, any publicly known method can be used without limitation. Examples of such a known method include the calcium chloride/rubidium chloride method, the calcium phosphate method, DEAE-dextran transfection, and electroporation. Inter alia, preferred for *Corynebacterium glutamicum* is electroporation, which can be performed by a known method (Kurusu, Y. et al., Electroporation-transformation system for Coryneform bacteria by auxotrophic complementation., Agric. Biol. Chem. 54:443-447 (1990); and Vertes A. A. et al., Presence of mrr- and mcr-like restriction systems in Coryneform bacteria. Res. Microbiol. 144:181-185 (1993)).

The transformant is cultured using a culture medium usually used for culture of microorganisms. The culture medium may be a natural or synthetic medium containing a carbon source, a nitrogen source, inorganic salts, other nutritional substances, etc.

Examples of the carbon source include carbohydrates and sugar alcohols such as glucose, fructose, sucrose, mannose, maltose, mannitol, xylose, arabinose, galactose, starch, molasses, sorbitol and glycerol; organic acids such as acetic acid, citric acid, lactic acid, fumaric acid, maleic acid and gluconic acid; and alcohols such as ethanol and propanol. Hydrocarbons, such as normal paraffin, etc. may also be used as desired. These carbon sources may be used alone or as a mixture of two or more thereof. The concentration of these carbon sources in the culture medium is usually about 0.1 to 10 w/v %.

Examples of the nitrogen source include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N—Z-amine, protein hydrolysate, amino acid, etc. may also be used. These nitrogen sources may be used alone or as a mixture of two or more thereof. The concentration of these nitrogen sources in the culture medium varies depending on the kind of the nitrogen compound, but is usually about 0.1 to 10 w/v %.

Examples of the inorganic salts include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. These inorganic salts may be used alone or as a mixture of two or more thereof. The concentration of the inorganic salts in the culture medium varies depending on the kind of the inorganic salts, but is usually about 0.01 to 1 w/v %.

Examples of the nutritional substances include meat extract, peptone, polypeptone, yeast extract, dry yeast, corn steep liquor, skim milk powder, defatted soybean hydrochloric acid hydrolysate, and extract from animals, plants or microorganisms, and degradation products thereof. The concentration of the nutritional substances in the culture medium varies depending on the kind of the nutritional substances, but is usually about 0.1 to 10 w/v %. Further, vitamins may be added as needed. Examples of the vitamins include biotin, thiamine (vitamin B1), pyridoxine (vitamin B6), pantothenic acid, inositol, nicotinic acid, etc.

The pH of the culture medium is preferably about 5 to 8.

Examples of the preferable microbial culture medium include A medium (Inui, M. et al., Metabolic analysis of *Corynebacterium glutamicum* during lactate and succinate productions under oxygen deprivation conditions. J. Mol. Microbiol. Biotechnol. 7:182-196 (2004)), BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)), etc.

The culture temperature is about 15 to 45° C., and the culture period is about 1 to 7 days.

Disruption or Deletion in Host Chromosomal Gene

In *Corynebacterium glutamicum* as a host, the gene which encodes an enzyme having phenol 2-monooxygenase activity (poxF) on the chromosome preferably has a disruption or deletion for further efficient phenol production. In addition, in *Corynebacterium glutamicum* as a host, the gene which encodes an enzyme having 4-hydroxybenzoate hydroxylase activity (pobA) on the chromosome preferably has a disruption or deletion for further efficient phenol production.

Particularly preferred is that both of poxF and pobA have a disruption or deletion.

Replacement of a gene on the chromosome with the corresponding gene having an disruption or deletion can be achieved by creating a gene with deletion mutation for not allowing production of a normally functioning enzyme protein, and transforming a bacterium with a DNA comprising the mutated gene for recombination in which the gene on the chromosome and the mutated gene are exchanged. An enzyme protein encoded by a gene having a disruption or deletion, even when produced, has a conformation different from that of the wild type, and has no or reduced function. The gene deletion or gene disruption by way of gene replacement through such homologous recombination has already been established, and examples thereof include a method using a plasmid containing a temperature sensitive replication origin or a plasmid capable of conjugal transfer, and a method using a suicide vector not having a replication origin that works in a host (U.S. Pat. No. 6,303,383 and JP 05-007491 A).

Specifically, by the method described in Example 1, *Corynebacterium glutamicum* in which poxF is disrupted or deleted can be obtained. In addition, in a similar way, *Corynebacterium glutamicum* in which pobA is disrupted or deleted can be obtained.

(II) Process for Producing Phenol

Phenol can be produced by a process comprising a step of allowing the above-described transformant of the present invention to react in a reaction mixture containing 4-hydroxybenzoate, and a step of collecting phenol from the reaction mixture.

Proliferation of Microorganism

Before the reaction, the transformant is preferably cultured and proliferated under aerobic conditions at about 25 to 38° C. for about 12 to 48 hours.

Culture Medium

The culture medium used for aerobic culture of the transformant before the reaction may be a natural or synthetic medium containing a carbon source, a nitrogen source, inorganic salts, other nutritional substances, etc.

Examples of the carbon source that can be used include saccharides (monosaccharides such as glucose, fructose, mannose, xylose, arabinose, and galactose; disaccharides such as sucrose, maltose, lactose, cellobiose, xylobiose, and trehalose; polysaccharides such as starch; and molasses); sugar alcohols such as mannitol, sorbitol, xylitol, and glycerol; organic acids such as acetic acid, citric acid, lactic acid, fumaric acid, maleic acid and gluconic acid; alcohols such as ethanol and propanol; and hydrocarbons such as normal paraffin.

These carbon sources may be used alone or as a mixture of two or more thereof.

Examples of the nitrogen source that can be used include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N—Z-amine, protein hydrolysate, amino acid, etc. may also be used. These nitrogen sources may be used alone or as a mixture of two or more thereof. The concentration of these nitrogen sources in the culture medium varies depending on the kind of the nitrogen compound, but is usually about 0.1 to 10 w/v %.

Examples of the inorganic salts include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. These inorganic salts may be used alone or as a mixture of two or more thereof. The concentration of the inorganic salts in the culture medium varies depending on the kind of the inorganic salts, but is usually about 0.01 to 1 w/v %.

Examples of the nutritional substances include meat extract, peptone, polypeptone, yeast extract, dry yeast, corn steep liquor, skim milk powder, defatted soybean hydrochloric acid hydrolysate, and extract from animals, plants or microorganisms, and degradation products thereof. The concentration of the nutritional substances in the culture medium varies depending on the kind of the nutritional substances, but is usually about 0.1 to 10 w/v %.

Further, vitamins may be added as needed. Examples of the vitamins include biotin, thiamine (vitamin B1), pyridoxine (vitamin B6), pantothenic acid, inositol, nicotinic acid, etc.

The pH of the culture medium is preferably about 6 to 8.

Specific examples of the preferable culture medium for *Corynebacterium glutamicum* include A medium (Inui, M. et al., Metabolic analysis of *Corynebacterium glutamicum* during lactate and succinate productions under oxygen deprivation conditions. J. Mol. Microbiol. Biotechnol. 7:182-196 (2004)), BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)), etc. Such a culture medium can be used after prepared so as to contain a saccharide at a concentration in the above-mentioned range.

Reaction Mixture

As the reaction mixture, water, a buffer solution, an inorganic salt medium, or the like, containing a phenol precursor (raw material for phenol) can be used. As the precursor, 4-hydroxybenzoate is used. Examples of the 4-hydroxybenzoate include salts, such as a sodium salt and a potassium salt; esters with alcohols having 1 to 4 carbon atoms; etc. Inter alia, preferred are salts, and more preferred is a sodium salt. The precursor may be used alone or a mixture of two or more kinds.

The concentration of the 4-hydroxybenzoate in the reaction mixture is preferably about 0.5 to 20 w/v %, more preferably about 1 to 10 w/v %, and still more preferably about 2 to 5 w/v %. As an aromatic compound, 4-hydroxybenzoate has a negative effect on cell viability. However, when the 4-hydroxybenzoate concentration is in the above range, phenol can be efficiently produced.

Examples of the buffer solution include a phosphate buffer, a Tris buffer, a carbonate buffer, etc. The concentration of the buffer solution is preferably about 10 to 150 mM.

Examples of the inorganic salt medium include a medium containing one or more kinds of inorganic salts including potassium dihydrogen phosphate, dipotassiumhydrogenphosphate, magnesium sulfate, sodium chloride, iron(II) nitrate, manganese sulfate, zinc sulfate, cobalt sulfate, and calcium carbonate. Inter alia, preferred is a medium containing magnesium sulfate. Specific example of the inorganic salt medium include BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)) etc.

The concentration of the inorganic salts in the culture medium varies depending on the kind of the inorganic salts, but is usually about 0.01 to 1 w/v %.

The pH of the reaction mixture is preferably about 6 to 8. During the reaction, the pH of the reaction mixture is preferably kept nearly neutral, in particular at around 7 with the use of aqueous ammonia, aqueous sodium hydroxide, or the like, under the control of a pH controller (for example, Type: DT-1023 made by Able).

Reaction Conditions

The reaction temperature, that is, the temperature for keeping the transformant alive during the reaction is preferably about 20 to 50° C., and more preferably about 25 to 47° C. When the temperature is in the above range, phenol can be efficiently produced.

The reaction period is preferably about 1 to 7 days, and more preferably about 1 to 3 days.

The culture may be a batch process, a fed-batch process, or a continuous process. Inter alia, a batch process is preferred.

<Reducing Conditions>

The reaction may be performed under aerobic conditions or reducing conditions, but preferably is performed under reducing conditions. Under reducing conditions, *Corynebacterium glutamicum* does not substantially proliferate and can further efficiently produce phenol.

The "reducing conditions" is defined based on the oxidation-reduction potential of the reaction mixture. The oxidation-reduction potential of the reaction mixture is preferably about −200 mV to −500 mV, and more preferably about −250 mV to −500 mV.

The reducing conditions of the reaction mixture can be simply estimated with the use of resazurin indicator (in reducing conditions, decolorization from blue to colorless is observed). However, for precise measurement, a redox-potential meter (for example, ORP Electrodes made by BROADLEY JAMES) is used.

As a method of preparing a reaction mixture under reducing conditions, any publicly known method can be used without limitation. For example, as a liquid medium for preparation of the reaction mixture, an aqueous solution for a reaction mixture may be used instead of distilled water or the like. As reference for preparation of the aqueous solution for a reaction mixture, for example, the method for preparing a culture medium for strictly anaerobic microorganisms, such as sulfate-reducing microorganisms (Pfennig, N. et al.: The dissimilatory sulfate-reducing bacteria, In The Prokaryotes, A Handbook on Habitats, Isolation and Identification of Bacteria, Ed. by Starr, M. P. et al. Berlin, Springer Verlag, 926-940, 1981, or *Nogeikagaku Jikkensho*, Ed. by Kyoto Daigaku Nogakubu Nogeikagaku Kyoshitsu, Vol. 3, Sangyo Tosho, 1990, Issue 26) may be used, and such a method provides an aqueous solution under desired reducing conditions.

Specifically, by treating distillated water or the like with heat or under reduced pressure for removal of dissolved gases, an aqueous solution for a reaction mixture under reducing conditions can be obtained. In this case, for removal of dissolved gases, especially dissolved oxygen, distillated water or the like may be treated under reduced pressure of about 10 mmHg or less, preferably about 5 mmHg or less, more preferably about 3 mmHg or less, for about 1 to 60 minutes, preferably for about 5 to 40 minutes.

Alternatively, by adding a suitable reducing agent (for example, thioglycolic acid, ascorbic acid, cysteine hydrochloride, mercaptoacetic acid, thiol acetic acid, glutathione, sodium sulfide, etc.), an aqueous solution for a reaction mixture under reducing conditions can be prepared.

These methods may be suitably combined to prepare an effective aqueous solution for a reaction mixture under reducing conditions.

It is preferred to maintain the reducing conditions of the reaction mixture during the reaction. For maintenance of reducing conditions, it is preferred that oxygen from the outside of the reaction system is prevented to the utmost extent from entering the system. Specific examples of the method employed for this purpose include a method comprising encapsulating the reaction system with inert gas, such as nitrogen gas, carbon dioxide gas, etc. In some cases, for allowing the metabolic functions in the cells of the aerobic bacterium of the present invention to work effectively during the reaction, addition of a solution of various nutrients or a reagent solution for adjusting and maintaining the pH of the reaction system may be needed. In such a case, for more effective prevention of oxygen incorporation, it is effective to remove oxygen in the solutions to be added, in advance.

Collection of Phenol

Through the culture performed in the above manner, phenol is produced in the reaction mixture. Phenol can be collected by collecting the reaction mixture, and it is also feasible to isolate phenol from the reaction mixture by a known method. Examples of such a known method include distillation, the membrane permeation method, and the organic solvent extraction method.

EXAMPLES

Hereinafter, the present invention will be illustrated in more detail by Examples, but is not limited thereto.

Example 1

Cloning and Expression of Phenol-producing Genes (1) Extraction of Chromosomal DNA from Microorganisms To extract chromosomal DNA from *Corynebacterium glutamicum* R (FERM P-18976), the bacterium was inoculated, with the use of a platinum loop, into A medium (2 g of $(NH_2)_2CO_3$ 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O+0.042\%$ (w/v) $MnSO_4.2H_2O$, 1 mL of 0.02% (w/v) biotin solution, 2 mL of 0.01% (w/v) thiamin solution, 2 g of yeast extract, and 7 g of vitamin assay casamino acid were dissolved in 1 L of distilled water), which was supplemented with 50% (w/v) glucose as a carbon source to a final concentration of 4%, and cultured with shaking at 33° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Bacillus subtilis* NBRC 14144, the bacterium was inoculated into NBRC Medium No. 802 (10 g of polypeptone, 2 g of yeast extract, and 1 g of $MgSO_4.7H_2O$ were dissolved in 1 L of distilled water) with the use of a platinum loop, and cultured with shaking at 37° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Bacillus atrophaeus* JCM 9070, the bacterium was inoculated into JCM Medium No. 22 (10 g of polypeptone, 10 g of beef extract, and 5 g of NaCl were dissolved in 1 L of distilled water) with the use of a platinum loop, and cultured with shaking at 30° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Bacillus subtilis* subsp. spizizenii NBRC 101239, the bacterium was inoculated into NBRC Medium No. 802 (10 g of polypeptone, 2 g of yeast extract, and 1 g of $MgSO_4.7H_2O$ were dissolved in 1 L of distilled water) with the use of a platinum loop, and cultured with shaking at 37° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

The chromosomal DNA of *Citrobacter koseri* ATCC BAA-895 (catalog No. BAA-895D-5) was obtained from American Type Culture Collection (ATCC).

To extract chromosomal DNA from *Enterobacter aerogenes* NBRC 13534, the bacterium was inoculated into NBRC Medium No. 802 (10 g of polypeptone, 2 g of yeast extract, and 1 g of $MgSO_4.7H_2O$ were dissolved in 1 L of distilled water) with the use of a platinum loop, and cultured with shaking at 37° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Enterobacter cloacae* NBRC 13535, the bacterium was inoculated into NBRC Medium No. 802 (10 g of polypeptone, 2 g of yeast extract, and 1 g of $MgSO_4.7H_2O$ were dissolved in 1 L of distilled water) with the use of a platinum loop, and cultured with shaking at 37° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Enterobacter hormaechei* ATCC 49162, the bacterium was inoculated into Tryptic Soy Broth Medium (30 g of Tryptic Soy Broth (made by Becton Dickinson and Company, catalog No. 211825) was dissolved in 1 L of distilled water) with the use of a platinum loop, and cultured with shaking at 30° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

The chromosomal DNA of *Enterobacter* sakazakii ATCC BAA-894 (catalog No. BAA-894D-5) was obtained from American Type Culture Collection (ATCC).

To extract chromosomal DNA from *Escherichia coli* W NBRC 13500, the bacterium was inoculated into NBRC Medium No. 802 (10 g of polypeptone, 2 g of yeast extract, and 1 g of $MgSO_4.7H_2O$ were dissolved in 1 L of distilled water) with the use of a platinum loop, and cultured with shaking at 30° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Escherichia fergusonii* NBRC 102419, the bacterium was inoculated into NBRC Medium No. 802 (10 g of polypeptone, 2 g of yeast extract, and 1 g of MgSO$_4$.7H$_2$O were dissolved in 1 L of distilled water) with the use of a platinum loop, and cultured with shaking at 30° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Paenibacillus polymyxa* NBRC 15309, the bacterium was inoculated into NBRC Medium No. 802 (10 g of polypeptone, 2 g of yeast extract, and 1 g of MgSO$_4$.7H$_2$O were dissolved in 1 L of distilled water) with the use of a platinum loop, and cultured with shaking at 30° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

To extract chromosomal DNA from *Pantoea ananatis* LMG 20103, the bacterium was inoculated into BCCM/LMG BateriCulture Medium No. 1 (1 g of beef extract, 2 g of yeast extract, 5 g of peptone, and 5 g of NaCl were dissolved in 1 L of distilled water) with the use of a platinum loop, and cultured with shaking at 30° C. until the logarithmic growth phase. After the bacterial cells were collected, chromosomal DNA was recovered from the collected cells with the use of a DNA extraction kit (trade name: GenomicPrep Cells and Tissue DNA Isolation Kit, made by Amersham) according to the instruction manual.

(2) Construction of Cloning Vectors

Construction of Cloning Vector pCRB22

A DNA fragment comprising a DNA replication origin sequence of pCASE1, a plasmid derived from *Corynebacterium casei* JCM12072 (hereinafter abbreviated as pCASE1-ori) and a DNA fragment comprising a cloning vector pHSG298 (made by Takara Bio, Inc.) were amplified by the following PCR method.

In the PCR, the following sets of primers were synthesized based on SEQ ID NO: 1 (pCASE1-ori sequence) and SEQ ID NO: 2 (cloning vector pHSG298) for cloning of the pCASE1-ori sequence and the cloning vector pHSG298, and were used.

Primers for pCASE1-ori sequence amplification

```
                                           (SEQ ID NO: 3)
   (a-1);    5'-AT AGATCT AGAACGTCCGTAGGAGC-3'

(SEQ ID NO: 4)
   (b-1);    5'-AT AGATCT GACTTGGTTACGATGGAC-3'
```

Primers (a-1) and (b-1) each have a BglII restriction enzyme site added thereto.

Primers for Cloning Vector pHSG298 Amplification

```
                                           (SEQ ID NO: 5)
   (a-2):    5'-AT AGATCT AGGTTTCCCGACTGGAAAG-3'

(SEQ ID NO: 6)
   (b-2):    5'-AT AGATCT CGTGCCAGCTGCATTAATGA-3'
```

Primers (a-2) and (b-2) each have a BglII restriction enzyme site added thereto.

As the template DNA, total DNA extracted from *Corynebacterium casei* JCM12072 obtained from Japan Collection of Microorganisms (JCM) and cloning vector pHSG298 (made by Takara Bio, Inc.) were used.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*$^)$ | 0.5 μL each (final conc.: 1 μM) |
| Sterile distilled water | 25.5 μL |

The above ingredients were mixed, and 50 μL of the reaction mixture was subjected to PCR.
*$^)$For amplification of the pCASE1-ori sequence, a combination of primers (a-1) and (b-1), and for amplification of the cloning vector pHSG298, a combination of primers (a-2) and (b-2) was used.

PCR Cycle:

Denaturation step: 94° C., 60 seconds

Annealing step: 52° C., 60 seconds

Extension step: 72° C.

pCASE1-ori sequence: 150 seconds

Cloning vector pHSG298: 180 seconds

A cycle consisting of the above 3 steps was repeated 30 times.

Using 10 μL of the above-produced reaction mixture, 0.8% agarose gel electrophoresis was performed. In the case of the pCASE1-ori sequence, an about 1.4-kb DNA fragment was detected. In the case of the cloning vector pHSG298, an about 2.7-kb DNA fragment was detected.

10 μL of the about 1.4-kb DNA fragment comprising the pCASE1-ori sequence derived from *Corynebacterium casei*, and 10 μL of the about 2.7-kb DNA fragment comprising the cloning vector pHSG298, both amplified by the above PCR, were each cut with the use of restriction enzyme BglII and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named Ligation Liquid A.

With the use of the Ligation Liquid A, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of restriction enzyme BglII to confirm the inserted fragment. As a result, in addition to an about 2.7-kb DNA fragment of the cloning vector pHSG298, an about 1.4-kb DNA fragment of the pCASE-ori sequence was confirmed.

The cloning vector comprising the pCASE1-ori sequence was named pCRB22.

Construction of Cloning Vector pCRB207

A DNA fragment comprising a promoter sequence of the gapA gene encoding the glyceraldehyde-3-phosphate dehydrogenase (hereinafter abbreviated as PgapA) derived from *Corynebacterium glutamicum* R, and a DNA fragment comprising an rrnBT1T2 bidirectional terminator sequence (hereinafter abbreviated as terminator sequence) derived from a cloning vector pKK223-3 (made by Pharmacia) were amplified by the following method.

In the PCR, the following sets of primers were synthesized based on SEQ ID NO: 7 (PgapA sequence) and SEQ ID NO: 8 (terminator sequence) for cloning of the PgapA sequence and the terminator sequence, and were used.

Primers for PgapA Sequence Amplification

```
                                              (SEQ ID NO:9)
(a-3);   5'-CTCT GTCGAC CCGAAGATCTGAAGATTCCTG-3'

(SEQ ID NO: 10)
(b-3);   5'-CTCT GTCGAC GGATCC CCATGG
         TGTGTCTCCTCTAAAGATTGTAGG-3'
```

Primer (a-3) has a SalI restriction enzyme site added thereto, and primer (b-3) has SalI, BamHI, and NcoI restriction enzyme sites added thereto.

Primers for Terminator Sequence Amplification

```
                                              (SEQ ID NO: 11)
(a-4);   5'-CTCT GCATGC CCATGG CTGTTTTGGCGGATGAG
         AGA-3'

(SEQ ID NO: 12)
(b-4);   5'-CTCT GCATGC TCATGA AAGAGTTTGTAGAAACG
         CAAAAAGG-3'
```

Primer (a-4) has SphI and NcoI restriction enzyme sites added thereto, and primer (b-4) has SphI and BspHI restriction enzyme sites added thereto.

As the template DNA, the chromosomal DNA extracted from *Corynebacterium glutamicum* R (FERM P-18976) and the plasmid pKK223-3 (made by Pharmacia) were used.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*$^{)}$ | 0.5 μL each (final conc.: 1 μM) |
| Sterile distilled water | 25.5 μL |

The above ingredients were mixed, and 50 μL of the reaction mixture was subjected to PCR.
*$^{)}$For amplification of the PgapA sequence, a combination of primers (a-7) and (b-7), and for amplification of the terminator sequence, a combination of primers (a-8) and (b-8) was used.

PCR Cycle:
Denaturation step: 94° C., 60 seconds
Annealing step: 52° C., 60 seconds
Extension step: 72° C.
PgapA sequence: 45 seconds
Terminator sequence: 30 seconds
A cycle consisting of the above 3 steps was repeated 30 times.

Using 10 μL of the above-produced reaction mixture, 0.8% agarose gel electrophoresis was performed. In the case of the PgapA sequence, an about 0.6-kb DNA fragment was detected. In the case of the terminator sequence, an about 0.4-kb DNA fragment was detected.

10 μL of the about 0.6-kb DNA fragment comprising the PgapA sequence derived from *Corynebacterium glutamicum* R, which was amplified by the above PCR, and the about 4.1-kb cloning vector pCRB22 were each cut with the use of restriction enzyme SalI and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 and the mixture was allowed to react at 15° C. for 3 hours for ligation. This was named Ligation Liquid B.

With the use of the Ligation Liquid B, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of restriction enzyme SalI to confirm the inserted fragment. As a result, in addition to an about 4.1-kb DNA fragment of the cloning vector pCRB22, an about 0.6-kb DNA fragment of the PgapA sequence was confirmed.

The cloning vector comprising the PgapA sequence was named pCRB206.

10 μL of the about 0.4-kb DNA fragment comprising the terminator sequence derived from the plasmid pKK223-3, which was amplified by the above PCR, was cut with the use of restriction enzymes NcoI and BspHI, 2 μL of the above cloning vector pCRB206 was cut with the use of restriction enzyme NcoI, and both were processed at 70° C. for 10 minutes for deactivation of the restriction enzymes. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named Ligation Liquid C.

With the use of the Ligation Liquid C, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of the restriction enzyme to confirm the inserted fragment. As a result, in addition to an about 4.7-kb DNA fragment of the cloning vector pCRB206, an about 0.4-kb DNA fragment of the terminator sequence was confirmed.

The cloning vector comprising the rrnBT1T2 terminator sequence was named pCRB207.

Construction of Cloning Vector pCRB209

A DNA fragment comprising a promoter sequence of the gapA (glyceraldehyde 3-phosphate dehydrogenase A) gene (hereinafter abbreviated as PgapA) derived from *Corynebacterium glutamicum* R was amplified by the following method.

In the PCR, the following set of primers was synthesized based on SEQ ID NO: 13 (pCRB207) for cloning of the pCRB207 sequence, and was used.

Primers for pCRB207 Sequence Amplification

```
                                              (SEQ ID NO: 14)
(a-5);   5'-CTCT CATATG CTGTTTTGGCGGATGAGAG-3'

(SEQ ID NO: 15)
(b-5);   5'-CTCT CATATG GTGTCTCCTCTAAAGATTGTAGG-3'
```

Primers (a-5) and (b-5) each have an NdeI restriction enzyme site added thereto.

As the template DNA, the cloning vector pCRB207 comprising a gapA promoter and a rrnBT1T2 terminator sequence was used.

Actual PCR was performed with the use of a thermal cycler, GeneAmp PCR System 9700 (made by Applied Biosystems) and TaKaRa LA Taq (made by Takara SHUZO) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg²⁺ free) | 5 μL |
| 25 mM MgCl₂ | 5 μL |
| dNTP Mixture (2.5 mM each) | 8 μL |
| Template DNA | 5 μL (DNA content: 1 μg or less) |
| The above 2 primers*⁾ | 0.5 μL each (final conc.: 1 μM) |
| Sterile distilled water | 25.5 μL |

The above ingredients were mixed, and 50 μL of the reaction mixture was subjected to PCR.
*⁾For amplification of the pCRB207 sequence, a combination of primers (a-5) and (b-5) was used.

The above ingredients were mixed, and 50 μL of the reaction mixture was subjected to PCR.

*) For amplification of the pCRB207 sequence, a combination of primers (a-5) and (b-5) was used.

PCR Cycle:
Denaturation step: 94° C., 60 seconds
Annealing step: 52° C., 60 seconds
Extension step: 72° C., 307 seconds
A cycle consisting of the above 3 steps was repeated 30 times.

Using 10 μL of the above-produced reaction mixture, 0.8% agarose gel electrophoresis was performed, and an about 5.1-kb DNA fragment comprising the cloning vector pCRB207 was detected.

10 μL of the about 5.1-kb DNA fragment comprising the gene derived from pCRB207, which was amplified by the above PCR, was cut with the use of restriction enzyme NdeI and processed at 70° C. for 10 minutes for deactivation of the restriction enzyme. To this, 1 μL of T4 DNA ligase 10× buffer solution and 1 unit of T4 DNA ligase (made by Takara SHUZO) were added. Sterile distilled water was added thereto so that the total volume was 10 μL, and the mixture was allowed to react at 15° C. for 3 hours for ligation. This was named Ligation Liquid D.

With the use of the Ligation Liquid D, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of restriction enzyme NdeI to confirm the inserted restriction enzyme site.

The cloning vector comprising the PgapA sequence and the rrnBT1T2 terminator sequence was named pCRB209.

(3) Cloning of Phenol-producing Genes

Cloning of Phenol-producing Gene Derived from *Bacillus subtilis*

A DNA fragment comprising the bsdBCD gene which is derived from *Bacillus subtilis* and which encodes a gene having 4-hydroxybenzoate decarboxylase activity was amplified by the PCR method as described below.

In the PCR, the following set of primers was synthesized based on SEQ ID NO: 16 (the bsdBCD gene of *Bacillus subtilis*) with the use of "394 DNA/RNA Synthesizer" made by Applied Biosystems for cloning of the bsdBCD gene, and was used.

Primers for bsdBCD Gene Amplification

```
                                        (SEQ ID NO: 17)
(a-6);   5'-CTCT CATATG AAAGCAGAATTCAAGCGTAAAG-3'

(SEQ ID NO: 18)
(b-6);   5'-CTCT CATATG GATCAAGCCTTTCGTTCCG-3'
```

Primers (a-6) and (b-6) each have an NdeI restriction enzyme site added thereto.

Cloning of Phenol-producing Gene Derived from *Bacillus atrophaeus*

A DNA fragment comprising the dca gene which is derived from *Bacillus atrophaeus* and which encodes a gene having 4-hydroxybenzoate decarboxylase activity was amplified by the PCR method as described below.

In the PCR, the following set of primers was synthesized based on SEQ ID NO: 23 (the dca gene of *Bacillus* atrophaeus) with the use of "394 DNA/RNA Synthesizer" made by Applied Biosystems for cloning of the dca gene, and was used.

Primers for dca Gene Amplification

```
(a-9);
                                        (SEQ ID NO: 24)
5'-CTCT CATATG AAACTCGTTGTCGGGATG-3'

(b-9);
                                        (SEQ ID NO: 25)
5'-CTCT CATATG TCAGGCCTTTCTTTCC-3'
```

Primers (a-9) and (b-9) each have an NdeI restriction enzyme site added thereto.

Cloning of Phenol-producing Gene Derived from *Bacillus subtilis* Subsp. spizizenii A DNA fragment comprising the dca gene which is derived from *Bacillus subtilis* subsp. spizizenii and which encodes a gene having 4-hydroxybenzoate decarboxylase activity was amplified by the PCR method as described below.

In the PCR, the following set of primers was synthesized based on SEQ ID NO: 26 (the dca gene of *Bacillus subtilis* subsp. spizizenii) with the use of "394 DNA/RNA Synthesizer" made by Applied Biosystems for cloning of the dca gene, and was used.

Primers for dca Gene Amplification

```
(a-10);
                                        (SEQ ID NO: 27)
5'-CTCT CATATG AAAGCAGAATTCAAGCGTAAAG-3'

(b-10);
                                        (SEQ ID NO: 28)
5'-CTCT CATATG TCAAGCCTTTCGTTCCGG-3'
```

Primers (a-10) and (b-10) each have an NdeI restriction enzyme site added thereto.

Cloning of Phenol-producing Gene Derived from *Citrobacter koseri*

A DNA fragment comprising the dca gene which is derived from *Citrobacter koseri* and which encodes a gene having 4-hydroxybenzoate decarboxylase activity was amplified by the PCR method as described below.

In the PCR, the following set of primers was synthesized based on SEQ ID NO: 29 (the dca gene of *Citrobacter koseri*)

with the use of "394 DNA/RNA Synthesizer" made by Applied Biosystems for cloning of the dca gene, and was used.
Primers for dca Gene Amplification (a-11);
(SEQ ID NO: 30)
5'-CTCT CATATG AAACTCGTTGTCGGGATG-3'

(b-11);
(SEQ ID NO: 31)
5'-CTCT CATATG TCAGGCCTTTCTTTCC-3'

Primers (a-11) and (b-11) each have an NdeI restriction enzyme site added thereto.
Cloning of Phenol-producing Gene Derived from *Enterobacter aerogenes*

A DNA fragment comprising the dca gene which is derived from *Enterobacter aerogenes* and which encodes a gene having 4-hydroxybenzoate decarboxylase activity was amplified by the PCR method as described below.

In the PCR, the following set of primers was synthesized based on SEQ ID NO: 32 (the dca gene of *Enterobacter aerogenes*) with the use of "394 DNA/RNA Synthesizer" made by Applied Biosystems for cloning of the dca gene, and was used.
Primers for dca Gene Amplification (a-12);
(SEQ ID NO: 33)
5'-CTCT CATATG AAACTGATTATTGGGATGACCG-3'

(b-12);
(SEQ ID NO: 34)
5'-CTCT CATATG TTAACGCTTATCTGCCGCC-3'

Primers (a-12) and (b-12) each have an NdeI restriction enzyme site added thereto.
Cloning of Phenol-producing Gene Derived from *Enterobacter cloacae*

A DNA fragment comprising the dca gene which is derived from *Enterobacter cloacae* and which encodes a gene having 4-hydroxybenzoate decarboxylase activity was amplified by the PCR method as described below.

In the PCR, the following set of primers was synthesized based on SEQ ID NO: 35 (the dca gene of *Enterobacter cloacae*) with the use of "394 DNA/RNA Synthesizer" made by Applied Biosystems for cloning of the dca gene, and was used. Primers for dca Gene Amplification (a-13);
(SEQ ID NO: 36)
5'-CTCT CATATG AGATTGATCGTGGGAATGAC-3'

(b-13);
(SEQ ID NO: 37)
5'-CTCT CATATG TTACAGCAATGGCGGAATGG-3'

Primers (a-13) and (b-13) each have an NdeI restriction enzyme site added thereto.
Cloning of Phenol-producing Gene Derived from *Enterobacter hormaechei*

A DNA fragment comprising the dca gene which is derived from *Enterobacter hormaechei* and which encodes a gene having 4-hydroxybenzoate decarboxylase activity was amplified by the PCR method as described below.

In the PCR, the following set of primers was synthesized based on SEQ ID NO: 38 (the dca gene of *Enterobacter hormaechei*) with the use of "394 DNA/RNA Synthesizer" made by Applied Biosystems for cloning of the dca gene, and was used. Primers for dca gene amplification (a-14);
(SEQ ID NO: 39)
5'-CTCT CATATG AGATTGATTGTGGGAATGAC-3'

(b-14);
(SEQ ID NO: 40)
5'-CTCT CATATG GAGTCTGGTTTAGTTCTCTGC-3'

Primers (a-14) and (b-14) each have an NdeI restriction enzyme site added thereto.
Cloning of Phenol-producing Gene Derived from *Enterobacter sakazakii*

A DNA fragment comprising the dca gene which is derived from *Enterobacter sakazakii* and which encodes a gene having 4-hydroxybenzoate decarboxylase activity was amplified by the PCR method as described below.

In the PCR, the following set of primers was synthesized based on SEQ ID NO: 41 (the dca gene of *Enterobacter sakazakii*) with the use of "394 DNA/RNA Synthesizer" made by Applied Biosystems for cloning of the dca gene, and was used. Primers for dca gene amplification (a-15);
(SEQ ID NO: 42)
5'-CTCT CATATG AGGCTAATTGTCGGAATGAC-3'

(b-15);
(SEQ ID NO: 43)
5'-CTCT CATATG TTAACGCTTACCATCCGCC-3'

Primers (a-15) and (b-15) each have an NdeI restriction enzyme site added thereto.
Cloning of Phenol-producing Gene Derived from *Escherichia coli*

A DNA fragment comprising the dca gene which is derived from *Escherichia coli* and which encodes a gene having 4-hydroxybenzoate decarboxylase activity was amplified by the PCR method as described below.

In the PCR, the following set of primers was synthesized based on SEQ ID NO: 44 (the dca gene of *Escherichia coli*) with the use of "394 DNA/RNA Synthesizer" made by Applied Biosystems for cloning of the dca gene, and was used.
Primers for dca Gene Amplification (a-16);
(SEQ ID NO: 45)
5'-CTCT CATATG AAACTGATCGTCGGGATG-3'

(b-16);
(SEQ ID NO: 46)
5'-CTCT CATATG TTAGCGCTTACCTTCCGC-3'

Primers (a-16) and (b-16) each have an NdeI restriction enzyme site added thereto.
Cloning of Phenol-producing Gene Derived from *Escherichia fergusonii*

A DNA fragment comprising the dca gene which is derived from *Escherichia fergusonii* and which encodes a gene having 4-hydroxybenzoate decarboxylase activity was amplified by the PCR method as described below.

In the PCR, the following set of primers was synthesized based on SEQ ID NO: 47 (the dca gene of *Escherichia fergusonii*) with the use of "394 DNA/RNA Synthesizer" made by Applied Biosystems for cloning of the dca gene, and was used.

Primers for dca Gene Amplification

```
(a-17);
                                         (SEQ ID NO: 48)
5'-CTCT CATATG AGACTGATCGTCGGGAT-3'

(b-17);
                                         (SEQ ID NO: 49)
5'-CTCT CATATG TTAGCGCTTATCTGCCGC-3'
```

Primers (a-17) and (b-17) each have an NdeI restriction enzyme site added thereto.

Cloning of Phenol-producing Gene Derived from *Paenibacillus polymyxa*

A DNA fragment comprising the dca gene which is derived from *Paenibacillus polymyxa* and which encodes a gene having 4-hydroxybenzoate decarboxylase activity was amplified by the PCR method as described below.

In the PCR, the following set of primers was synthesized based on SEQ ID NO: 50 (the dca gene of *Paenibacillus polymyxa*) with the use of "394 DNA/RNA Synthesizer" made by Applied Biosystems for cloning of the dca gene, and was used.

Primers for dca Gene Amplification

```
(a-18);
                                         (SEQ ID NO: 51)
5'-CTCT CATATG AAGAAAATCATTGTAGGAATATCGG-3'

(b-18);
                                         (SEQ ID NO: 52)
5'-CTCT CATATG CTATATCCGCTCTGGAATAGG-3'
```

Primers (a-18) and (b-18) each have an NdeI restriction enzyme site added thereto.

Cloning of Phenol-producing Gene Derived from *Pantoea ananatis*

A DNA fragment comprising the dca gene which is derived from *Pantoea ananatis* and which encodes a gene having 4-hydroxybenzoate decarboxylase activity was amplified by the PCR method as described below.

In the PCR, the following set of primers was synthesized based on SEQ ID NO: 53 (the dca gene of *Pantoea* ananatis) with the use of "394 DNA/RNA Synthesizer" made by Applied Biosystems for cloning of the dca gene, and was used.

Primers for Dca Gene Amplification

```
(a-19);
                                         (SEQ ID NO: 54)
5'-CTCT CATATG AGTAGATTACTGTTAATTTCATTCGTAC-3'

(b-19);
                                         (SEQ ID NO: 55)
5'-CTCT CATATG TTACTTAGCTAACAGAGGAGGG-3'
```

Primers (a-19) and (b-19) each have an NdeI restriction enzyme site added thereto.

As the template DNA for *Bacillus subtilis*, the chromosomal DNA extracted from *Bacillus subtilis* NBRC 14144 obtained from NITE (National Institute of Technology and Evaluation) Biological Resource Center (NBRC) was used.

For *Bacillus atrophaeus*, the chromosomal DNA extracted from *Bacillus atrophaeus* JCM 9070 obtained from Japan Collection of Microorganisms (JCM) was used.

For *Bacillus subtilis* subsp. spizizenii, the chromosomal DNA extracted from *Bacillus subtilis* subsp. spizizenii NBRC 101239 obtained from NITE (National Institute of Technology and Evaluation) Biological Resource Center (NBRC) was used.

For *Citrobacter koseri*, the *Citrobacter koseri* chromosomal DNA obtained from American Type Culture Collection (ATCC) (catalog No. BAA-895D-5) was used.

For *Enterobacter aerogenes*, the chromosomal DNA extracted from *Enterobacter aerogenes* NBRC 13534 obtained from NITE (National Institute of Technology and Evaluation) Biological Resource Center (NBRC) was used.

For *Enterobacter cloacae*, the chromosomal DNA extracted from *Enterobacter cloacae* NBRC 13535 obtained from NITE (National Institute of Technology and Evaluation) Biological Resource Center (NBRC) was used.

For *Enterobacter hormaechei*, the chromosomal DNA extracted from *Enterobacter hormaechei* ATCC 49162 obtained from American Type Culture Collection (ATCC) was used.

For *Enterobacter sakazakii*, the *Enterobacter sakazakii* chromosomal DNA obtained from American Type Culture Collection (ATCC) (catalog No. BAA-894D-5) was used.

For *Escherichia coli* W, the chromosomal DNA extracted from *Escherichia coli* W NBRC 13500 obtained from NITE (National Institute of Technology and Evaluation) Biological Resource Center (NBRC) was used.

For *Escherichia fergusonii*, the chromosomal DNA extracted from *Escherichia fergusonii* NBRC 102419 obtained from NITE (National Institute of Technology and Evaluation) Biological Resource Center (NBRC) was used.

For *Paenibacillus polymyxa*, the chromosomal DNA extracted from *Paenibacillus polymyxa* NBRC 15309 obtained from NITE (National Institute of Technology and Evaluation) Biological Resource Center (NBRC) was used.

For *Pantoea* ananatis, the chromosomal DNA extracted from *Pantoea ananatis* LMG 20103 obtained from BCCM/LMG (Belgian Coordinated Collections of Microorganisms/Laboratory for Microbiology, University of Gent) was used.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II ($Mg^{2+}$ free) | 5 μL |
| 25 mM $MgCl_2$ | 5 μL |
| dNTP Mixture (2.5 mM each) | 8 μL |
| Template DNA | 5 μL (DNA content: 1 μg or less) |
| The above 2 primers*) | 0.5 μL each (final conc.: 1 μM) |
| Sterile distilled water | 25.5 μL |

The above ingredients were mixed, and 50 μL of the reaction mixture was subjected to PCR.

*)For amplification of the bsdBCD gene of *Bacillus subtilis*, a combination of primers (a-6) and (b-6); for amplification of the dca gene *Bacillus atrophaeus*, a combination of primers (a-9) and (b-9); for amplification of the dca gene of *Bacillus subtilis* subsp. *spizizenii*, a combination of primers (a-10) and (b-10); for amplification of the dca gene of *Citrobacter koseri*, a combination of primers (a-11) and (b-11); for amplification of the dca gene of *Enterobacter aerogenes*, a combination of primers (a-12) and (b-12); for amplification of the dca gene of *Enterobacter cloacae*, a combination of primers (a-13) and (b-13); for amplification of the dca gene of *Enterobacter hormaechei*, a combination of primers (a-14) and (b-14); for amplification of the dca gene of *Enterobacter sakazakii*, a combination of primers (a-15) and (b-15); for amplification of the dca gene of *Escherichia coli* W, a combination of primers (a-16) and (b-16); for amplification of the dca gene of *Escherichia fergusonii*, a combination of primers (a-17) and (b-17); for amplification of the dca gene of *Paenibacillus polymyxa*, a combination of primers (a-18) and (b-18); and for amplification of the dca gene of *Pantoea ananatis*, a combination of primers (a-19) and (b-19) were used.

PCR Cycle:
Denaturation step: 94° C., 60 seconds
Annealing step: 52° C., 60 seconds
Extension step: 72° C.

| | |
|---|---|
| *Bacillus subtilis* bsdBCD gene | 137 seconds |
| *Bacillus atrophaeus* dca gene | 135 seconds |

-continued

| | |
|---|---|
| Bacillus subtilis subsp. spizizenii dca gene | 137 seconds |
| Citrobacter koseri dca gene | 136 seconds |
| Enterobacter aerogenes dca gene | 136 seconds |
| Enterobacter cloacae dca gene | 135 seconds |
| Enterobacter hormaechei dca gene | 141 seconds |
| Enterobacter sakazakii dca gene | 137 seconds |
| Escherichia coli W dca gene | 136 seconds |
| Escherichia fergusonii dca gene | 136 seconds |
| Paenibacillus polymyxa dca gene | 138 seconds |
| Pantoea ananatis dca gene | 139 seconds |

A cycle consisting of the above 3 steps was repeated 30 times.

With the use of 10 μL of the reaction mixture produced above, 0.8% agarose gel electrophoresis was performed. As a result, detected were an about 2.3-kb DNA fragment in the case of the *Bacillus subtilis* bsdBCD gene, an about 2.3-kb DNA fragment in the case of the *Bacillus* atrophaeus bsdBCD gene, an about 2.3-kb DNA fragment in the case of the *Bacillus subtilis* subsp. spizizenii dca gene, an about 2.3-kb DNA fragment in the case of the *Citrobacter koseri* dca gene, an about 2.3-kb DNA fragment in the case of the *Enterobacter aerogenes* dca gene, an about 2.3-kb DNA fragment in the case of the *Enterobacter cloacae* dca gene, an about 2.4-kb DNA fragment in the case of the *Enterobacter hormaechei* dca gene, an about 2.3-kb DNA fragment in the case of the *Enterobacter sakazakii* dca gene, an about 2.3-kb DNA fragment in the case of the *Escherichia coli* W dca gene, an about 2.3-kb DNA fragment in the case of the *Escherichia fergusonii* dca gene, an about 2.3-kb DNA fragment in the case of the *Paenibacillus polymyxa* dca gene, and an about 2.3-kb DNA fragment in the case of the *Pantoea ananatis* dca gene.

(4) Construction of Phenol-producing Gene Expression Plasmids

Cloning of Phenol-producing Genes to pCRB209

10 μL of the about 2.3-kb DNA fragment comprising the bsdBCD gene derived from *Bacillus subtilis*, the about 2.3-kb DNA fragment comprising the dca gene derived from *Bacillus atrophaeus*, the about 2.3-kb DNA fragment comprising the dca gene derived from *Bacillus subtilis* subsp. spizizenii, the about 2.3-kb DNA fragment comprising the dca gene derived from *Citrobacter koseri*, the about 2.3-kb DNA fragment comprising the dca gene derived from *Enterobacter aerogenes*, the about 2.3-kb DNA fragment comprising the dca gene derived from *Enterobacter cloacae*, the about 2.4-kb DNA fragment comprising the dca gene derived from *Enterobacter hormaechei*, the about 2.3-kb DNA fragment comprising the dca gene derived from *Enterobacter sakazakii*, the about 2.3-kb DNA fragment comprising the dca gene derived from *Escherichia coli* W, the about 2.3-kb DNA fragment comprising the dca gene derived from *Escherichia fergusonii*, the about 2.3-kb DNA fragment comprising the dca gene derived from *Paenibacillus polymyxa*, or the about 2.3-kb DNA fragment comprising the dca gene derived from *Pantoea ananatis*, each amplified by the PCR in the above (3), and 2 μL of the cloning vector pCRB209 comprising promoter PgapA were each cut with the use of restriction enzyme NdeI, and were processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. The resulting liquid was named Ligation Liquids E, G, H, I, J, K, L, M, N, O, P, or Q.

With the use of each of the obtained 12 kinds of Ligation Liquids E, G, H, I, J, K, L, M, N, O, P, and Q, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of restriction enzyme to confirm the inserted fragment. As a result, in addition to an about 5.1-kb DNA fragment of the plasmid pCRB209, confirmed were an about 2.3-kb inserted fragment in the case of the bsdBCD gene derived from *Bacillus subtilis* (Ligation Liquid E), an about 2.3-kb inserted fragment in the case of the dca gene derived from *Bacillus atrophaeus* (Ligation Liquid G), an about 2.3-kb inserted fragment in the case of the dca gene derived from *Bacillus subtilis* subsp. *spizizenii* (Ligation Liquid H), an about 2.3-kb inserted fragment in the case of the dca gene derived from *Citrobacter koseri* (Ligation Liquid I), an about 2.3-kb inserted fragment in the case of the dca gene derived from *Enterobacter aerogenes* (Ligation Liquid J), an about 2.3-kb inserted fragment in the case of the dca gene derived from *Enterobacter cloacae* (Ligation Liquid K), an about 2.4-kb inserted fragment in the case of the dca gene derived from *Enterobacter hormaechei* (Ligation Liquid L), an about 2.3-kb inserted fragment in the case of the dca gene derived from *Enterobacter sakazakii* (Ligation Liquid M), an about 2.3-kb inserted fragment in the case of the dca gene derived from *Escherichia coli* W (Ligation Liquid N), an about 2.3-kb inserted fragment in the case of the dca gene derived from *Escherichia fergusonii* (Ligation Liquid 0), an about 2.3-kb inserted fragment in the case of the dca gene derived from *Paenibacillus polymyxa* (Ligation Liquid P), and an about 2.3-kb inserted fragment in the case of the dca gene derived from *Pantoea ananatis*was (Ligation Liquid Q).

The plasmid comprising the bsdBCD gene derived from *Bacillus subtilis* was named pCRB209-bsdBCD/BS (FIG. 1), the plasmid comprising the dca gene derived from *Bacillus atrophaeus* was named pCRB209-dca/BAE, the plasmid comprising the dca gene derived from *Bacillus subtilis* subsp. spizizenii was named pCRB209-dca/BSS, the plasmid comprising the dca gene derived from *Citrobacter koseri* was named pCRB209-dca/CKO, the plasmid comprising the dca gene derived from *Enterobacter aerogenes* was named pCRB209-dca/EAE, the plasmid comprising the dca gene derived from *Enterobacter cloacae* was named pCRB209-dca/ECL, the plasmid comprising the dca gene derived from *Enterobacter hormaechei* was named pCRB209-dca/EHO, the plasmid comprising the dca gene derived from *Enterobacter sakazakii* was named pCRB209-dca/ESA, the plasmid comprising the dca gene derived from *Escherichia coli* W was named pCRB209-dca/ECK, the plasmid comprising the dca gene derived from *Escherichia fergusonii* was named pCRB209-dca/EFE, the plasmid comprising the dca gene derived from *Paenibacillus polymyxa* was named pCRB209-dca/PPY, and the plasmid comprising the dca gene derived from *Pantoea ananatis* was named pCRB209-dca/PAM.

(5) Construction of Plasmids for *Corynebacterium glutamicum* Chromosomal Gene Disruption Construction of Plasmid for *Corynebacterium glutamicum* poxF Gene Disruption A DNA fragment required for constructing a plasmid for markerless disruption of the poxF gene on the chromosome of *Corynebacterium glutamicum* was amplified by the PCR method as described below.

In the PCR, the following sets of primers were synthesized based on the sequence of *Corynebacterium glutamicum* R with the use of "394 DNA/RNA Synthesizer" made by Applied Biosystems, and were used.
Primers for Amplification of poxF-1 Region (a-7);
(SEQ ID NO: 19)
5'-CTCT TCTAGA TACGTCCTAAACACCCGAC-3'

(b-7);
(SEQ ID NO: 20)
5'-GACCAACCATTGCTGACTTGCGTATCCATAGTCAGGCTTC-3'

Primer (a-7) has an XbaI restriction enzyme site added thereto.
Primers for Amplification of poxF-2 Region (a-8);
(SEQ ID NO: 21)
5'-CAAGTCAGCAATGGTTGGTC-3'

(b-8);
(SEQ ID NO: 22)
5'-CTCT TCTAGA TGATCAGTACCAAGGGTGAG-3'

Primer (b-8) has an XbaI restriction enzyme site added thereto.

As the template DNA, the chromosomal DNA extracted from *Corynebacterium glutamicum* R was used.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.
Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*$^{)}$ | 0.5 μL each (final conc.: 1 μM) |
| Sterile distilled water | 25.5 μL |

The above ingredients were mixed, and 50 μL of the reaction mixture was subjected to PCR.
*$^{)}$For amplification of the poxF-1 region, a combination of primers (a-7) and (b-7), and for amplification of the poxF-2 region, a combination of primers (a-8) and (b-8) were used.

PCR Cycle:
Denaturation step: 94° C., 60 seconds
Annealing step: 52° C., 60 seconds
Extension step: 72° C.
poxF-1 region: 50 seconds
poxF-2 region: 50 seconds
A cycle consisting of the above 3 steps was repeated 30 times.

Using 10 μL of the above-produced reaction mixture, 0.8% agarose gel electrophoresis was performed. An about 0.8-kb DNA fragment in the case of the *Corynebacterium glutamicum* poxF-1 region, and an about 0.8-kb DNA fragment in the case of the poxF-2 region were detected.

Subsequently, 1 μL each of the poxF-1 region fragment and the poxF-2 region fragment, which were amplified by the above PCR, were mixed and subjected to PCR for ligation.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.
Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| The above 2 fragments*$^{)}$ | 1 μL each |
| Sterile distilled water | 29.5 μL |

The above ingredients were mixed, and 50 μL of the reaction mixture was subjected to PCR.
*$^{)}$ poxF-1 region fragment and poxF-2 region fragment were used.

PCR Cycle:
Denaturation step: 95° C., 20 seconds
Annealing step: 52° C., 5 seconds
Extension step: 72° C., 50 seconds
A cycle consisting of the above 3 steps was repeated 30 times.

Further, using, as the template DNA, the obtained fragment in which poxF-1 and poxF-2 were ligated, a poxF deletion fragment was amplified by PCR.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.
Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*$^{)}$ | 0.5 μL each (final conc.: 1 μM) |
| Sterile distilled water | 25.5 μL |

The above ingredients were mixed, and 50 μL of the reaction mixture was subjected to PCR.
*$^{)}$For amplification of the poxF deletion fragment, a combination of primers (a-7) and (b-8) was used.

PCR Cycle:
Denaturation step: 95° C., 20 seconds
Annealing step: 52° C., 5 seconds
Extension step: 72° C., 97 seconds
A cycle consisting of the above 3 steps was repeated 30 times.

Using 10 μL of the above-produced reaction mixture, 0.8% agarose gel electrophoresis was performed, and an about 1.6-kb fragment of the poxF deletion fragment was detected.

10 μL of the about 1.7-kb DNA fragment of the poxF deletion fragment derived from *Corynebacterium glutamicum* R, which was amplified by the above PCR, and 2 μL of an about 4.4-kb plasmid pCRA725 for markerless chromosomal gene transfection (J. Mol. Microbiol. Biotechnol., Vol. 8, 243-254, 2004 (JP 2006-124440 A)) were each cut with the use of restriction enzyme XbaI, and processed at 70° C. for 10 minutes for deactivation of the restriction enzyme. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named Ligation Liquid F.

With the use of the Ligation Liquid F, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of restriction enzyme XbaI to confirm the inserted fragment. As a result, in addition to an about 4.4-kb DNA fragment of the plasmid pCRA725, an about 1.7-kb inserted fragment of the pheA deletion gene derived from *Corynebacterium glutamicum* (Ligation Liquid F) were confirmed.

The plasmid comprising the poxF deletion gene derived from *Corynebacterium glutamicum* was named pCRA725-poxF/CG.

Construction of Plasmid for *Corynebacterium glutamicum* pobA Gene Disruption

A DNA fragment required for constructing a plasmid for markerless disruption of the pobA gene on the chromosome of *Corynebacterium glutamicum* was amplified by the PCR method as described below.

In the PCR, the following sets of primers were synthesized based on the sequence of *Corynebacterium glutamicum* R with the use of "394 DNA/RNA Synthesizer" made by Applied Biosystems, and were used.

Primers for Amplification of pobA-1 Region

```
(a-20);
                                             (SEQ ID NO: 56)
5'-CTCT TCTAGA GAAACGATCAAGTGCACCAG-3'

(b-20);
                                             (SEQ ID NO: 57)
5'-GACACGAGCGTTTATACCTCTAATTGCCACTGGTACGTGG-3'
```

Primer (a-20) has an XbaI restriction enzyme site added thereto.

Primers for Amplification of pobA-2 Region

```
(a-21);
                                             (SEQ ID NO: 58)
5'-GAGGTATAAACGCTCGTGTC-3'

(b-21);
                                             (SEQ ID NO: 59)
5'-CTCT GAGCTC GAGAACACGAACCATACGAG-3'
```

Primer (b-21) has a SadI restriction enzyme site added thereto.

As the template DNA, the chromosomal DNA extracted from *Corynebacterium glutamicum* R was used.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*$^)$ | 0.5 μL each (final conc.: 1 μM) |
| Sterile distilled water | 25.5 μL |

The above ingredients were mixed, and 50 μL of the reaction mixture was subjected to PCR.
*$^)$ For amplification of the pobA-1 region, a combination of primers (a-20) and (b-20), and for amplification of the pobA-2 region, a combination of primers (a-21) and (b-21) were used.

PCR Cycle:
Denaturation step: 94° C., 60 seconds
Annealing step: 52° C., 60 seconds
Extension step: 72° C., pobA-1 region: 60 seconds
pobA-2 region: 60 seconds A cycle consisting of the above 3 steps was repeated 30 times.

Using 10 μL of the above-produced reaction mixture, 0.8% agarose gel electrophoresis was performed. An about 1.0-kb DNA fragment in the case of the *Corynebacterium glutamicum* pobA-1 region, and an about 1.0-kb DNA fragment in the case of the pobA-2 region were detected.

Subsequently, 1 μL each of the pobA-1 region fragment and the pobA-2 region fragment, which were amplified by the above PCR, were mixed and subjected to PCR for ligation.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| The above 2 fragments*$^)$ | 1 μL each |
| Sterile distilled water | 29.5 μL |

The above ingredients were mixed, and 50 μL of the reaction mixture was subjected to PCR.
*$^)$ pobA-1 region fragment and pobA-2 region fragment were used.

PCR Cycle:
Denaturation step: 95° C., 20 seconds
Annealing step: 52° C., 5 seconds
Extension step: 72° C., 50 seconds A cycle consisting of the above 3 steps was repeated 30 times.

Further, using, as the template DNA, the obtained fragment in which pobA-1 and pobA-2 were ligated, a pobA deletion fragment was amplified by PCR.

Actual PCR was performed with the use of a thermal cycler, GeneAmp PCR System 9700 (made by Applied Biosystems) and TaKaRa LA Taq (made by Takara Bio, Inc.) as a reaction reagent under the conditions described below.

Reaction Mixture:

| | |
|---|---|
| TaKaRa LA Taq ™ (5 units/μL) | 0.5 μL |
| 10× LA PCR ™ Buffer II (Mg$^{2+}$ free) | 5 μL |
| 25 mM MgCl$_2$ | 5 μL |
| dNTP Mixture (2.5 mM each) | 8 μL |
| Template DNA | 5 μL (DNA content: 1 μg or less) |
| The above 2 primers*$^)$ | 0.5 μL each (final conc.: 1 μM) |
| Sterile distilled water | 25.5 μL |

The above ingredients were mixed, and 50 μL of the reaction mixture was subjected to PCR.
*$^)$ For amplification of the pobA deletion fragment, a combination of primers (a-20) and (b-21) was used.

PCR Cycle:
Denaturation step: 95° C., 20 seconds
Annealing step: 52° C., 5 seconds
Extension step: 72° C., 97 seconds A cycle consisting of the above 3 steps was repeated 30 times.

Using 10 μL of the above-produced reaction mixture, 0.8% agarose gel electrophoresis was performed, and an about 2.0-kb fragment of the pobA deletion fragment was detected.

10 μL of the about 2.0-kb DNA fragment of the pobA deletion fragment derived from *Corynebacterium glutamicum* R, which was amplified by the above PCR, and 2 μL of an about 4.4-kb plasmid, pCRA725 for markerless chromosomal gene transfection (J. Mol. Microbiol. Biotechnol., Vol. 8, 243-254, 2004 (JP 2006-124440 A)) were each cut with the use of restriction enzymes XbaI and SacI, and processed at 70° C. for 10 minutes for deactivation of the restriction enzymes. Both were mixed, and 1 μL of T4 DNA ligase 10× buffer solution and 1 unit of T4 DNA ligase (made by Takara Bio, Inc.) were added thereto. Sterile distilled water was added thereto so that the total volume was 10 μL, and the mixture was allowed to react at 15° C. for 3 hours for ligation. This was named Ligation Liquid R.

With the use of the Ligation Liquid R, *Escherichia coli* JM109 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture and cut with the use of restriction enzymes XbaI and SacI to confirm the inserted fragment. As a result, in addition to an about 4.4-kb DNA fragment of the plasmid pCRA725, an about 2.0-kb inserted fragment of the pobA deletion gene derived from *Corynebacterium glutamicum* (Ligation Liquid N) was confirmed.

The plasmid comprising the pobA deletion gene derived from *Corynebacterium glutamicum* was named pCRA725-pobA/CG.

(6) Construction of by-product Formation Pathway Disputants

Construction of *Corynebacterium glutamicum* poxF Gene Disputant

Vector pCRA725 for markerless chromosomal gene transfection is a plasmid that cannot be replicated within *Corynebacterium glutamicum* R. With the use of the plasmid pCRA725-poxF/CG, transformation of *Corynebacterium glutamicum* R was performed by electroporation (Agric. Biol. Chem., Vol. 54, 443-447 (1990) and Res. Microbiol., Vol. 144, 181-185 (1993)), and the strain was applied to A agar medium (A liquid medium and 1.5% agar) containing 50 μg/mL of kanamycin. The single crossover strain obtained on the above medium was applied to BT agar medium (2 g of $(NH_2)_2CO_3$ 7 g of $(NH_4)_2SO_4$, 0.5 g of $KH_2PO_4$, 0.5 g of $K_2HPO_4$, 0.5 g of $MgSO_4 \cdot 7H_2O$, 1 mL of 0.06% (w/v) $Fe_2SO_4 \cdot 7H_2O$+0.042% (w/v) $MnSO_4 \cdot 2H_2O$, 1 mL of 0.02% (w/v) biotin solution, 2 mL of 0.01% (w/v) thiamin solution dissolved in 1 L of distilled water, and 1.5% agar) containing 10% (w/v) sucrose.

In the case of a strain having a single crossover of the plasmid pCRA725-poxF/CG with the homologous region on the chromosome, the strain shows kanamycin resistance resulting from the expression of the kanamycin resistance gene on the pCRA725-poxF/CG and mortality on a culture medium containing sucrose resulting from the expression of the *Bacillus subtilis* sacR-sacB gene. In the case of a strain having a double crossover of the plasmid pCRA725-poxF/CG, the strain shows kanamycin sensitivity resulting from the loss of the kanamycin resistance gene on the pCRA725-poxF/CG and growing ability on a culture medium containing sucrose resulting from the loss of the sacR-sacB gene. The markerless chromosomal gene disruptant shows kanamycin sensitivity and growing ability on a culture medium containing sucrose. Therefore, a strain that showed kanamycin sensitivity and growing ability on a culture medium containing sucrose was selected.

The Obtained Markerless poxF Gene Disruptant of *Corynebacterium glutamicum* R was named *Corynebacterium glutamicum* ΔpoxF.

Construction of *Corynebacterium glutamicum* poxF and pobA Gene Disruptant

Vector pCRA725 for markerless chromosomal gene transfection is a plasmid that cannot be replicated within *Corynebacterium glutamicum* R. With the use of the plasmid pCRA725-pobA/CG, transformation of *Corynebacterium glutamicum* ΔpoxF was performed by electroporation (Agric. Biol. Chem., Vol. 54, 443-447 (1990) and Res. Microbiol., Vol. 144, 181-185 (1993)), and the strain was applied to A agar medium (A liquid medium and 1.5% agar) containing 50 μg/mL of kanamycin. The single crossover strain obtained in the above medium was applied to BT agar medium (2 g of $(NH_2)_2CO_3$ 7 g of $(NH_4)_2SO_4$, 0.5 g of $KH_2PO_4$, 0.5 g of $K_2HPO_4$, 0.5 g of $MgSO_4 \cdot 7H_2O$, 1 mL of 0.06% (w/v) $Fe_2SO_4 \cdot 7H_2O$+0.042% (w/v) $MnSO_4 \cdot 2H_2O$, 1 mL of 0.02% (w/v) biotin solution, 2 mL of 0.01% (w/v) thiamin solution dissolved in 1 L of distilled water, and 1.5% agar) containing 10% (w/v) sucrose.

In the case of a strain having a single crossover of the plasmid pCRA725-pobA/CG with the homologous region on the chromosome, the strain shows kanamycin resistance resulting from the expression of the kanamycin resistance gene on the pCRA725-pobA/CG and mortality on a culture medium containing sucrose resulting from the expression of the *Bacillus subtilis* sacR-sacB gene. In the case of a strain having a double crossover of the plasmid pCRA725-pobA/CG, the strain shows kanamycin sensitivity resulting from the loss of the kanamycin resistance gene on the pCRA725-pobA/CG and growing ability on a culture medium containing sucrose resulting from the loss of the sacR-sacB gene. The markerless chromosomal gene disruptant shows kanamycin sensitivity and growing ability on a culture medium containing sucrose. Therefore, a strain that showed kanamycin sensitivity and growing ability on a culture medium containing sucrose was selected.

The obtained markerless pobA gene disruptant of *Corynebacterium glutamicum* ΔpoxF was named *Corynebacterium glutamicum* ΔpoxFΔpobA.

(7) Construction of Transgenic Strains for Phenol Production Gene

Transfection of Phenol-producing Genes into *Corynebacterium glutamicum* ΔpoxF

With the use of each of the above-described 12 kinds of plasmids pCRB209-bsdBCD/BS, pCRB209-dca/BAE, pCRB209-dca/BSS, pCRB209-dca/CKO, pCRB209-dca/EAE, pCRB209-dca/ECL, pCRB209-dca/EHO, pCRB209-dca/ESA, pCRB209-dca/ECK, pCRB209-dca/EFE, pCRB209-dca/PPY, and pCRB209-dca/PAM, transformation of *Corynebacterium glutamicum* ΔpoxF was performed by electroporation (Agric. Biol. Chem., Vol. 54, 443-447 (1990) and Res. Microbiol., Vol. 144, 181-185 (1993)), and the strain was applied to A agar medium containing 50 μg/mL of kanamycin.

A growing strain on the culture medium was subjected to liquid culture in the usual manner. Plasmid DNA was extracted from the culture and cut with the use of a restriction enzyme to confirm the inserted plasmid. As a result, transfection of the above-constructed plasmids pCRB209-bsdBCD/BS, pCRB209-dca/BAE, pCRB209-dca/BSS, pCRB209-dca/CKO, pCRB209-dca/EAE, pCRB209-dca/ECL, pCRB209-dca/EHO, pCRB209-dca/ESA, pCRB209-dca/ECK, pCRB209-dca/EFE, pCRB209-dca/PPY, and pCRB209-dca/PAM was confirmed.

The strain in which transfection of pCRB209-bsdBCD/BS had been confirmed was named *Corynebacterium glutamicum* PHE21, the strain in which transfection of pCRB209-dca/BAE had been confirmed was named *Coryne-* bacterium glutamicum PHE21-2, the strain in which transfection of pCRB209-dca/BSS had been confirmed was named *Corynebacterium glutamicum* PHE21-3, the strain in which transfection of pCRB209-dca/CKO had been confirmed was named *Corynebacterium glutamicum* PHE21-4, the strain in which transfection of pCRB209-dca/EAE had been confirmed was named *Corynebacterium glutamicum* PHE21-5, the strain in which transfection of pCRB209-dca/ECL had been confirmed was named *Corynebacterium glutamicum* PHE21-6, the strain in which transfection of pCRB209-dca/EHO had been confirmed was named *Corynebacterium glutamicum* PHE21-7, the strain in which transfection of pCRB209-dca/ESA had been confirmed was named *Corynebacterium glutamicum* PHE21-8, the strain in which transfection of pCRB209-dca/ECK had been confirmed was named *Corynebacterium glutamicum* PHE21-9, the strain in which transfection of pCRB209-dca/EFE had been confirmed was named *Corynebacterium glutamicum* PHE21-10, the strain in which transfection of pCRB209-dca/PPY had been confirmed was named *Corynebacterium glutamicum* PHE21-11, and the strain in which transfection of pCRB209-dca/PAM had been confirmed was named *Corynebacterium glutamicum* PHE21-12. The outline of gene recombination in the above-obtained strains is shown in Table 1.

*Corynebacterium glutamicum* PHE21 was deposited in Incorporated Administrative Agency National Institute of Technology and Evaluation, NITE Patent Microorganisms Depositary (2-5-8 Kazusakamatari, Kisarazu-shi, Chiba 292-0818 Japan) under Accession Number NITE BP-996 on Oct. 21, 2010.

TABLE 1

Transfection of phenol-producing gene into *Corynebacterium glutamicum* ΔpoxF

| Strain | Transfected plasmid | Origin of transfected gene | Host strain |
|---|---|---|---|
| PHE21 | pCRB209-bsdBCD/BS | *Bacillus subtilis* | *Corynebacterium glutamicum* ΔpoxF |
| PHE21-2 | pCRB209-dca/BAE | *Bacillus atrophaeus* | |
| PHE21-3 | pCRB209-dca/BSS | *Bacillus subtilis* subsp. *spizizenii* | |
| PHE21-4 | pCRB209-dca/CKO | *Citrobacter koseri* | |
| PHE21-5 | pCRB209-dca/EAE | *Enterobacter aerogenes* | |
| PHE21-6 | pCRB209-dca/ECL | *Enterobacter cloacae* | |
| PHE21-7 | pCRB209-dca/EHO | *Enterobacter hormaechei* | |
| PHE21-8 | pCRB209-dca/ESA | *Enterobacter sakazakii* | |
| PHE21-9 | pCRB209-dca/ECK | *Escherichia coli* W | |
| PHE21-10 | pCRB209-dca/EFE | *Escherichia fergusonii* | |
| PHE21-11 | pCRB209-dca/PPY | *Paenibacillus polymyxa* | |
| PHE21-12 | pCRB209-dca/PAM | *Pantoea ananatis* | |

Transfection of Phenol-producing Genes into *Corynebacterium glutamicum* ΔpoxFΔpobA With the use of each of the above-described 12 kinds of plasmids pCRB209-bsdBCD/BS, pCRB209-dca/BAE, pCRB209-dca/BSS, pCRB209-dca/CKO, pCRB209-dca/EAE, pCRB209-dca/ECL, pCRB209-dca/EHO, pCRB209-dca/ESA, pCRB209-dca/ECK, pCRB209-dca/EFE, pCRB209-dca/PPY, and pCRB209-dca/PAM, transformation of *Corynebacterium glutamicum* ΔpoxFΔpobA was performed by electroporation (Agric. Biol. Chem., Vol. 54, 443-447 (1990) and Res. Microbiol., Vol. 144, 181-185 (1993)), and the strain was applied to A agar medium containing 50 μg/mL of kanamycin.

A growing strain on the culture medium was subjected to liquid culture in the usual manner. Plasmid DNA was extracted from the culture and cut with the use of a restriction enzyme to confirm the inserted plasmid. As a result, transfection of the above-constructed plasmids pCRB209-bsdBCD/BS, pCRB209-dca/BAE, pCRB209-dca/BSS, pCRB209-dca/CKO, pCRB209-dca/EAE, pCRB209-dca/ECL, pCRB209-dca/EHO, pCRB209-dca/ESA, pCRB209-dca/ECK, pCRB209-dca/EFE, pCRB209-dca/PPY, and pCRB209-dca/PAM was confirmed.

The strain in which transfection of pCRB209-bsdBCD/BS had been confirmed was named *Corynebacterium glutamicum* PHE22-1, the strain in which transfection of pCRB209-dca/BAE had been confirmed was named *Corynebacterium glutamicum* PHE22-2, the strain in which transfection of pCRB209-dca/BSS had been confirmed was named *Corynebacterium glutamicum* PHE22-3, the strain in which transfection of pCRB209-dca/CKO had been confirmed was named *Corynebacterium glutamicum* PHE22-4, the strain in which transfection of pCRB209-dca/EAE had been confirmed was named *Corynebacterium glutamicum* PHE22-5, the strain in which transfection of pCRB209-dca/ECL had been confirmed was named *Corynebacterium glutamicum* PHE22-6, the strain in which transfection of pCRB209-dca/EHO had been confirmed was named *Corynebacterium glutamicum* PHE22-7, the strain in which transfection of pCRB209-dca/ESA had been confirmed was named *Corynebacterium glutamicum* PHE22-8, the strain in which transfection of pCRB209-dca/ECK had been confirmed was named *Corynebacterium glutamicum* PHE22-9, the strain in which transfection of pCRB209-dca/EFE had been confirmed was named *Corynebacterium glutamicum* PHE22-10, the strain in which transfection of pCRB209-dca/PPY had been confirmed was named *Corynebacterium glutamicum* PHE22-11, and the strain in which transfection of pCRB209-dca/PAM had been confirmed was named *Corynebacterium glutamicum* PHE22-12. The outline of gene recombination in the above-obtained strains is shown in Table 2.

TABLE 2

Transfection of phenol-producing gene into *Corynebacterium glutamicum* ΔpoxFΔpobA

| Strain | Transfected plasmid | Origin of transfected gene | Host strain |
|---|---|---|---|
| PHE22-1 | pCRB209-bsdBCD/BS | *Bacillus subtilis* | *Corynebacterium glutamicum* ΔpoxFΔpobA |
| PHE22-2 | pCRB209-dca/BAE | *Bacillus atrophaeus* | |
| PHE22-3 | pCRB209-dca/BSS | *Bacillus subtilis* subsp. *spizizenii* | |
| PHE22-4 | pCRB209-dca/CKO | *Citrobacter koseri* | |
| PHE22-5 | pCRB209-dca/EAE | *Enterobacter aerogenes* | |
| PHE22-6 | pCRB209-dca/ECL | *Enterobacter cloacae* | |
| PHE22-7 | pCRB209-dca/EHO | *Enterobacter hormaechei* | |
| PHE22-8 | pCRB209-dca/ESA | *Enterobacter sakazakii* | |
| PHE22-9 | pCRB209-dca/ECK | *Escherichia coli* W | |
| PHE22-10 | pCRB209-dca/EFE | *Escherichia fergusonii* | |
| PHE22-11 | pCRB209-dca/PPY | *Paenibacillus polymyxa* | |
| PHE22-12 | pCRB209-dca/PAM | *Pantoea ananatis* | |

Transfection of Phenol-producing Genes into *Corynebacterium glutamicum* R

With the use of each of the above-described 12 kinds of plasmids pCRB209-bsdBCD/BS, pCRB209-dca/BAE, pCRB209-dca/BSS, pCRB209-dca/CKO, pCRB209-dca/EAE, pCRB209-dca/ECL, pCRB209-dca/EHO, pCRB209-dca/ESA, pCRB209-dca/ECK, pCRB209-dca/EFE, pCRB209-dca/PPY, and pCRB209-dca/PAM, transformation of *Corynebacterium glutamicum* R was performed by electroporation (Agric. Biol. Chem., Vol. 54, 443-447 (1990) and Res. Microbiol., Vol. 144, 181-185 (1993)), and the strain was applied to A agar medium containing 50 μg/mL of kanamycin.

A growing strain on the culture medium was subjected to liquid culture in the usual manner. Plasmid DNA was extracted from the culture and cut with the use of a restriction enzyme to confirm the inserted plasmid. As a result, transfection of the above-constructed plasmids pCRB209-bsdBCD/BS, pCRB209-dca/BAE, pCRB209-dca/BSS, pCRB209-dca/CKO, pCRB209-dca/EAE, pCRB209-dca/ECL, pCRB209-dca/EHO, pCRB209-dca/ESA, pCRB209-dca/ECK, pCRB209-dca/EFE, pCRB209-dca/PPY, and pCRB209-dca/PAM was confirmed.

The strain in which transfection of pCRB209-bsdBCD/BS had been confirmed was named *Corynebacterium glutamicum* PHE23-1, the strain in which transfection of pCRB209-dca/BAE had been confirmed was named *Corynebacterium glutamicum* PHE23-2, the strain in which transfection of pCRB209-dca/BSS had been confirmed was named *Corynebacterium glutamicum* PHE23-3, the strain in which transfection of pCRB209-dca/CKO had been confirmed was named *Corynebacterium glutamicum* PHE23-4, the strain in which transfection of pCRB209-dca/EAE had been confirmed was named *Corynebacterium glutamicum* PHE23-5, the strain in which transfection of pCRB209-dca/ECL had been confirmed was named *Corynebacterium glutamicum* PHE23-6, the strain in which transfection of pCRB209-dca/EHO had been confirmed was named *Corynebacterium glutamicum* PHE23-7, the strain in which transfection of pCRB209-dca/ESA had been confirmed was named *Corynebacterium glutamicum* PHE23-8, the strain in which transfection of pCRB209-dca/ECK had been confirmed was named *Corynebacterium glutamicum* PHE23-9, the strain in which transfection of pCRB209-dca/EFE had been confirmed was named *Corynebacterium glutamicum* PHE23-10, the strain in which transfection of pCRB209-dca/PPY had been confirmed was named *Corynebacterium glutamicum* PHE23-11, and the strain in which transfection of pCRB209-dca/PAM had been confirmed was named *Corynebacterium glutamicum* PHE23-12. The outline of gene recombination in the above-obtained strains is shown in Table 3.

TABLE 3

Transfection of phenol-producing gene into *Corynebacterium glutamicum* R

| Strain | Transfected plasmid | Origin of transfected gene | Host strain |
|---|---|---|---|
| PHE23-1 | pCRB209-bsdBCD/BS | *Bacillus subtilis* | *Corynebacterium glutamicum* R |
| PHE23-2 | pCRB209-dca/BAE | *Bacillus atrophaeus* | |
| PHE23-3 | pCRB209-dca/BSS | *Bacillus subtilis* subsp. *spizizenii* | |
| PHE23-4 | pCRB209-dca/CKO | *Citrobacter koseri* | |
| PHE23-5 | pCRB209-dca/EAE | *Enterobacter aerogenes* | |
| PHE23-6 | pCRB209-dca/ECL | *Enterobacter cloacae* | |
| PHE23-7 | pCRB209-dca/EHO | *Enterobacter hormaechei* | |
| PHE23-8 | pCRB209-dca/ESA | *Enterobacter sakazakii* | |
| PHE23-9 | pCRB209-dca/ECK | *Escherichia coli* W | |
| PHE23-10 | pCRB209-dca/EFE | *Escherichia fergusonii* | |
| PHE23-11 | pCRB209-dca/PPY | *Paenibacillus polymyxa* | |
| PHE23-12 | pCRB209-dca/PAM | *Pantoea ananatis* | |

Example 2

Experiment of Phenol Production Using *Corynebacterium glutamicum* By-product Formation Pathway Disruptants and *Corynebacterium glutamicum* R (Wild Strain) Transfected with a Phenol-producing Gene Each of the *Corynebacterium glutamicum* ΔpoxF/phenol-producing gene transgenic strains prepared in Example 1 (see Table 1) was applied to A agar medium (2 g of $(NH_2)_2CO_3$ 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar were suspended in 1 L of distilled water) containing 50 μg/mL of kanamycin, and left stand in the dark at 28° C. for 20 hours.

An inoculation loop of the *Corynebacterium glutamicum* ΔpoxF/phenol-producing gene transgenic strain grown on a plate as above was inoculated into a test tube containing 10 mL of A liquid medium containing 50 μg/mL of kanamycin, and aerobically cultured with shaking at 28° C. for 15 hours.

The *Corynebacterium glutamicum* ΔpoxF/phenol-producing gene transgenic strain grown in the above conditions was inoculated into a 2 L-conical flask containing 500 mL of A liquid medium containing 50 μg/mL of kanamycin, and aerobically cultured with shaking at 28° C. for 15 hours.

The bacterial cells of each strain cultured and proliferated as above were collected by centrifugation (5,000×g at 4° C. for 15 minutes). The obtained bacterial cells were suspended in 50 mL of BT (-urea) liquid medium (0.7% ammonium sulfate, 0.05% potassium dihydrogen phosphate, 0.05% dipotassium hydrogen phosphate, 0.05% magnesium sulfate heptahydrate, 0.0006% iron sulfate heptahydrate, 0.00042% manganese sulfate hydrate, 0.00002% biotin and 0.00002% thiamine hydrochloride) so that the final concentration of the bacterial cell was 10%. To a 100-mL medium bottle, the cell suspension was transferred, sodium 4-hydroxybenzoate as a substrate was added so as to be 250 mM in concentration, and the reaction was allowed to proceed under reducing conditions (the ORP of the reaction mixture: −450 mV) in a water bath kept at 33° C. with stirring. During the reaction, the pH of the reaction mixture was kept at or above 7.0 through addition of 2.5 N aqueous ammonia controlled by a pH controller (Type: DT-1023 made by Able).

A sample of the reaction mixture was centrifuged (15,000×g at 4° C. for 10 minutes), and the obtained supernatant was used for quantitative determination of phenol.

As a result, in the reaction under reducing conditions, *Corynebacterium glutamicum* PHE21 had produced 65 mM (6 g/L) of phenol in an hour and 180 mM (17 g/L) of phenol in four hours (Table 4). Results for the *Corynebacterium glutamicum* strains PHE21-2 to PHE-21-12 under the same conditions are also shown in Table 4.

TABLE 4

Experiment of phenol production using *Corynebacterium glutamicum* ΔpoxF transfected with phenol-producing gene

| Strain | Transfected plasmid | Host strain | Amount of production (mM) 1 hour | 4 hours |
|---|---|---|---|---|
| PHE21 | pCRB209-bsdBCD/BS | *Corynebacterium glutamicum* ΔpoxF | 65 | 180 |
| PHE21-2 | pCRB209-dca/BAE | | 62 | 175 |
| PHE21-3 | pCRB209-dca/BSS | | 63 | 174 |
| PHE21-4 | pCRB209-dca/CKO | | 145 | 179 |
| PHE21-5 | pCRB209-dca/EAE | | 145 | 180 |
| PHE21-6 | pCRB209-dca/ECL | | 150 | 180 |
| PHE21-7 | pCRB209-dca/EHO | | 148 | 180 |
| PHE21-8 | pCRB209-dca/ESA | | 149 | 180 |
| PHE21-9 | pCRB209-dca/ECK | | 149 | 180 |
| PHE21-10 | pCRB209-dca/EFE | | 149 | 180 |
| PHE21-11 | pCRB209-dca/PPY | | 60 | 170 |
| PHE21-12 | pCRB209-dca/PAM | | 62 | 172 |

*) Abbreviations in the table stand for the following.
<Abbreviation for gene origin>
BS; *Bacillus subtilis*
BAE; *Bacillus atrophaeus*
BSS; *Bacillus subtilis* subsp. *spizizenii*
CKO; *Citrobacter koseri*
EAE; *Enterobacter aerogenes*
ECL; *Enterobacter cloacae*
EHO; *Enterobacter hormaechei*
ESA; *Enterobacter sakazakii*
ECK; *Escherichia coli* W
EFE; *Escherichia fergusonii*
PPY; *Paenibacillus polymyxa*
PAM; *Pantoea ananatis*

Subsequently, each of the *Corynebacterium glutamicum* ΔpoxFΔpobA/phenol-producing gene transgenic strains prepared in Example 1 (see Table 2) was applied to A agar medium (2 g of $(NH_2)_2CO_3$ 7 g of $(NH_4)_2SO_4$, 0.5 g of $KH_2PO_4$, 0.5 g of $K_2HPO_4$, 0.5 g of $MgSO_4 \cdot 7H_2O$, 1 mL of 0.06% (w/v) $Fe_2SO_4 \cdot 7H_2O$+0.042% (w/v) $MnSO_4 \cdot 2H_2O$, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar were suspended in 1 L of distilled water) containing 50 μg/mL of kanamycin, and left stand in the dark at 28° C. for 20 hours.

An inoculation loop of the *Corynebacterium glutamicum* ΔpoxFΔpobA/phenol-producing gene transgenic strain grown on a plate as above was inoculated into a test tube containing 10 mL of A liquid medium containing 50 μg/mL of kanamycin, and aerobically cultured with shaking at 28° C. for 15 hours.

The *Corynebacterium glutamicum* ΔpoxFΔpobA/phenol-producing gene transgenic strain grown in the above conditions was inoculated into a 2 L-conical flask containing 500 mL of A liquid medium containing 50 μg/mL of kanamycin, and aerobically cultured with shaking at 28° C. for 15 hours.

Each kind of the bacterial cells cultured and proliferated as above was collected by centrifugation (5,000×g at 4° C. for 15 minutes). The obtained bacterial cells were suspended in 50 mL of BT (-urea) liquid medium (0.7% ammonium sulfate, 0.05% potassium dihydrogen phosphate, 0.05% dipotassium hydrogen phosphate, 0.05% magnesium sulfate heptahydrate, 0.0006% iron sulfate heptahydrate, 0.00042% manganese sulfate hydrate, 0.00002% biotin and 0.00002% thiamine hydrochloride) so that the final concentration of the bacterial cell was 10%. To a 100-mL medium bottle, the cell suspension was transferred, sodium 4-hydroxybenzoate as a substrate was added so as to be 250 mM in concentration, and the reaction was allowed to proceed under reducing conditions (the ORP of the reaction mixture: −450 mV) in a water bath kept at 33° C. with stirring. During the reaction, the pH of the reaction mixture was kept at or above 7.0 through addition of 2.5 N aqueous ammonia controlled by a pH controller (Type: DT-1023 made by Able).

A sample of the reaction mixture was centrifuged (15,000×g at 4° C. for 10 minutes), and the obtained supernatant was used for quantitative determination of phenol.

As a result, in the reaction under reducing conditions, *Corynebacterium glutamicum* strains PHE22-1 to PHE22-12 had produced phenol in an hour in such amounts as shown in Table 5.

The results show that poxA-gene disruption improved the phenol productivity.

TABLE 5

Experiment of phenol production using *Corynebacterium glutamicum* ΔpoxFΔpobA transfected with phenol-producing gene

| Strain | Transfected plasmid | Host strain | Amount of production (mM) (1 hour) |
|---|---|---|---|
| PHE22-1 | pCRB209-bsdBCD/BS | *Corynebacterium glutamicum* ΔpoxFΔpobA | 100 |
| PHE22-2 | pCRB209-dca/BAE | | 98 |
| PHE22-3 | pCRB209-dca/BSS | | 95 |
| PHE22-4 | pCRB209-dca/CKO | | 168 |
| PHE22-5 | pCRB209-dca/EAE | | 170 |
| PHE22-6 | pCRB209-dca/ECL | | 170 |
| PHE22-7 | pCRB209-dca/EHO | | 169 |
| PHE22-8 | pCRB209-dca/ESA | | 170 |
| PHE22-9 | pCRB209-dca/ECK | | 169 |
| PHE22-10 | pCRB209-dca/EFE | | 169 |
| PHE22-11 | pCRB209-dca/PPY | | 94 |
| PHE22-12 | pCRB209-dca/PAM | | 95 |

*) Abbreviations in the table stand for the following.
<Abbreviation for gene origin>
BS; *Bacillus subtilis*
BAE; *Bacillus atrophaeus*
BSS; *Bacillus subtilis* subsp. *spizizenii*
CKO; *Citrobacter koseri*
EAE; *Enterobacter aerogenes*
ECL; *Enterobacter cloacae*
EHO; *Enterobacter hormaechei*
ESA; *Enterobacter sakazakii*
ECK; *Escherichia coli* W
EFE; *Escherichia fergusonii*
PPY; *Paenibacillus polymyxa*
PAM; *Pantoea ananatis*

Further, as Comparative Example, each of the *Corynebacterium glutamicum* R/phenol-producing gene transgenic strains prepared in Example 1 (see Table 3) was applied to A agar medium (2 g of $(NH_2)_2CO_3$ 7 g of $(NH_4)_2SO_4$, 0.5 g of $KH_2PO_4$, 0.5 g of $K_2HPO_4$, 0.5 g of $MgSO_4 \cdot 7H_2O$, 1 mL of 0.06% (w/v) $Fe_2SO_4 \cdot 7H_2O$+0.042% (w/v) $MnSO_4 \cdot 2H_2O$, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar were suspended in 1 L of distilled water) containing 50 μg/mL of kanamycin, and left stand in the dark at 28° C. for 20 hours.

An inoculation loop of the *Corynebacterium glutamicum* R/phenol-producing gene transgenic strain grown on a plate as above was inoculated into a test tube containing 10 mL of A liquid medium containing 50 µg/mL of kanamycin, and aerobically cultured with shaking at 28° C. for 15 hours.

The *Corynebacterium glutamicum* R/phenol-producing gene transgenic strain grown in the above conditions was inoculated into a 2 L-conical flask containing 500 mL of A liquid medium containing 50 µg/mL of kanamycin, and aerobically cultured with shaking at 28° C. for 15 hours.

Each kind of the bacterial cells cultured and proliferated as above was collected by centrifugation (5,000×g at 4° C. for 15 minutes). The obtained bacterial cells were suspended in 50 mL of BT (-urea) liquid medium (0.7% ammonium sulfate, 0.05% potassium dihydrogen phosphate, 0.05% dipotassium hydrogen phosphate, 0.05% magnesium sulfate heptahydrate, 0.0006% iron sulfate heptahydrate, 0.00042% manganese sulfate hydrate, 0.00002% biotin and 0.00002% thiamine hydrochloride) so that the final concentration of the bacterial cell was 10%. To a 100-mL medium bottle, the cell suspension was transferred, sodium 4-hydroxybenzoate as a substrate was added so as to be 250 mM in concentration, and the reaction was allowed to proceed under reducing conditions (the ORP of the reaction mixture: −450 mV) in a water bath kept at 33° C. with stirring. During the reaction, the pH of the reaction mixture was kept at or above 7.0 through addition of 2.5 N aqueous ammonia controlled by a pH controller (Type: DT-1023 made by Able).

A sample of the reaction mixture was centrifuged (15,000×g at 4° C. for 10 minutes), and the obtained supernatant was used for quantitative determination of phenol.

As a result, in the reaction under reducing conditions, *Corynebacterium glutamicum* strains PHE23-1 to PHE23-12 had produced phenol in an hour in such amounts as shown in Table 6. The results show that, when transfected with a phenol-producing gene, *Corynebacterium glutamicum* ΔpoxF (Table 4) exhibited higher phenol productivity than *Corynebacterium glutamicum* R (wild strain), and *Corynebacterium glutamicum* ΔpoxFΔpobA (Table 5) exhibited further higher productivity, and therefore revealed that poxF-gene disruption and pobA-gene disruption have a positive effect on the phenol productivity.

TABLE 6

Experiment of phenol production using *Corynebacterium glutamicum* R transfected with phenol-producing gene

| Strain | Transfected plasmid | Host strain | Amount of production (mM) (1 hour) |
|---|---|---|---|
| PHE23-1 | pCRB209-bsdBCD/BS | *Corynebacterium glutamicum* R | 43 |
| PHE23-2 | pCRB209-dca/BAE | | 41 |
| PHE23-3 | pCRB209-dca/BSS | | 42 |
| PHE23-4 | pCRB209-dca/CKO | | 96 |
| PHE23-5 | pCRB209-dca/EAE | | 97 |
| PHE23-6 | pCRB209-dca/ECL | | 100 |
| PHE23-7 | pCRB209-dca/EHO | | 100 |
| PHE23-8 | pCRB209-dca/ESA | | 99 |
| PHE23-9 | pCRB209-dca/ECK | | 100 |
| PHE23-10 | pCRB209-dca/EFE | | 97 |
| PHE23-11 | pCRB209-dca/PPY | | 40 |
| PHE23-12 | pCRB209-dca/PAM | | 42 |

*) Abbreviations in the table stand for the following.
<Abbreviation for gene origin>
BS; *Bacillus subtilis*
BAE; *Bacillus atrophaeus*
BSS; *Bacillus subtilis* subsp. *spizizenii*
CKO; *Citrobacter koseri*
EAE; *Enterobacter aerogenes*
ECL; *Enterobacter cloacae*
EHO; *Enterobacter hormaechei*
ESA; *Enterobacter sakazakii*

TABLE 6-continued

Experiment of phenol production using *Corynebacterium glutamicum* R transfected with phenol-producing gene

| Strain | Transfected plasmid | Host strain | Amount of production (mM) (1 hour) |
|---|---|---|---|

ECK; *Escherichia coli* W
EFE; *Escherichia fergusonii*
PPY; *Paenibacillus polymyxa*
PAM; *Pantoea ananatis*

Example 3

Test for Suitability as a Host for Phenol Production Influence of Phenol on Aerobic Proliferation A growth inhibition test in aerobic culture was performed to examine the influence of phenol on *Corynebacterium glutamicum*, *Escherichia coli*, and *Pseudomonas putida*. *Pseudomonas putida* S12, which was used for the test, is reported to be a solvent-resistant strain. In the report, disclosed is an unparalleled technology using the strain as a host in phenol production.

*Corynebacterium glutamicum* R was applied to A agar medium (2 g of $(NH_2)_2CO_3$ 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, 40 g of glucose, and 15 g of agar were suspended in 1 L of distilled water) and was left stand in the dark at 33° C. for 15 hours.

An inoculation loop of the *Corynebacterium glutamicum* R grown on a plate as above was inoculated into a test tube containing 10 mL of A liquid medium (2 g of $(NH_2)_2CO_3$ 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, and 40 g of glucose were suspended in 1 L of distilled water) and was aerobically cultured with shaking at 33° C. for 13 hours.

The *Corynebacterium glutamicum* R grown in the above conditions was inoculated into 100 mL of A liquid medium in such a way that the initial bacterial cell concentration would be $OD_{610}$=0.05, phenol was added at the same time in such a way that the final concentration would be 0, 0.16, 0.2, 0.24, or 0.32 mM, and aerobic culture was performed with shaking at 33° C. The growth of bacterial cells was determined by absorbance measurement at $OD_{610}$.

*Escherichia coli* JM109 was applied to LB agar medium (1% polypeptone, 0.5% yeast extract, 0.5% NaCl and 1.5% agar) and was left stand in the dark at 37° C. for 15 hours.

An inoculation loop of the *Escherichia coli* JM109 grown on a plate as above was inoculated into a test tube containing 10 mL of LB liquid medium (1% polypeptone, 0.5% yeast extract, and 0.5% NaCl), and aerobic culture was performed with shaking at 37° C. for 13 hours.

The *Escherichia coli* JM109 grown in the above conditions was inoculated into 100 mL of LB liquid medium in such a way that the initial bacterial cell concentration would be $OD_{610}$=0.05, phenol was added at the same time in such a way that the final concentration would be 0, 0.16, or 0.20 mM, and aerobic culture was performed with shaking at 37° C. The growth of bacterial cells was determined by absorbance measurement at $OD_{610}$.

Pseudomonas putida F1 and S12 were applied to LB agar medium (1% polypeptone, 0.5% yeast extract, 0.5% NaCl and 1.5% agar) and were left stand in the dark at 30° C. for 15 hours.

An inoculation loop of each of the *Pseudomonas putida* F1 and S12 grown on a plate as above was inoculated into a test tube containing 10 mL of LB (+glucose) liquid medium (1% polypeptone, 0.5% yeast extract, 0.5% NaCl and 0.4% glucose), and aerobic culture was performed with shaking at 30° C. for 13 hours.

The *Pseudomonas putida* F1 and S12 grown in the above conditions were each inoculated into 100 mL of LB (+glucose) liquid medium in such a way that the initial bacterial cell concentration would be $OD_{610}$=0.05, phenol was added at the same time in such a way that the final concentration would be 0, 0.10, or 0.20 mM, and aerobic culture was performed with shaking at 30° C.

Figure 2:
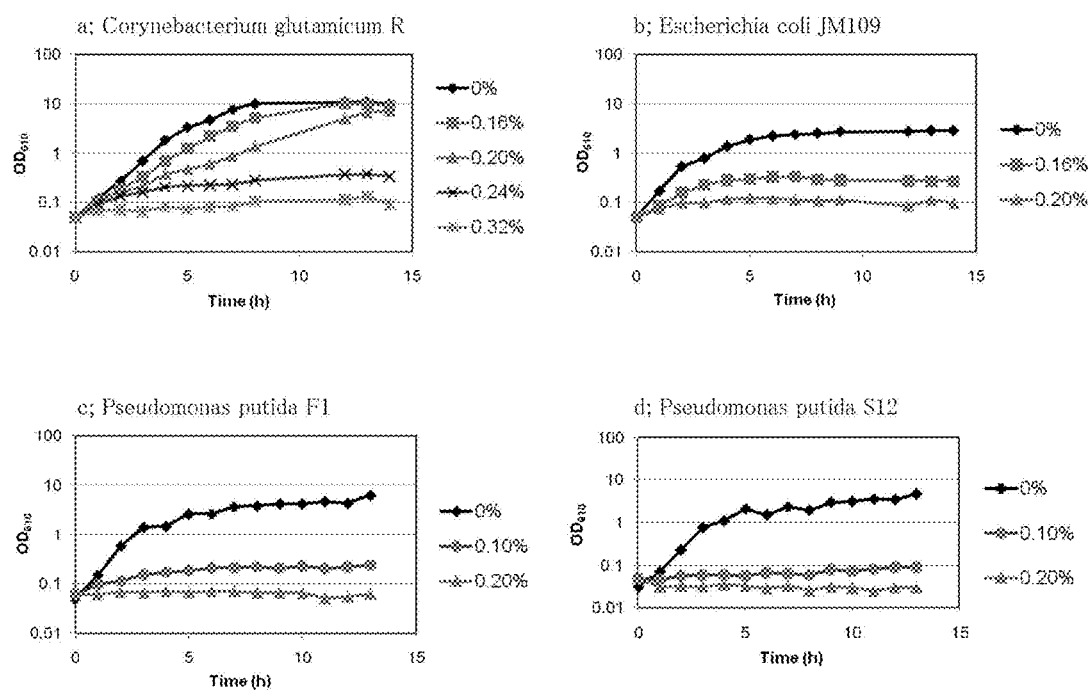
FIG. 2 shows the influence of phenol on proliferation of various microorganisms under aerobic conditions.

The growth of bacterial cells was determined by absorbance measurement at $OD_{610}$. FIG. 2 shows analysis results of the influence of phenol addition on aerobic proliferation.

The proliferation of *Escherichia coli* was significantly affected by 0.16% phenol and completely inhibited by 0.20% phenol.

*Pseudomonas putida* F1, and *Pseudomonas putida* S12, which was reported as a solvent-resistant strain, showed a similar tendency, and the proliferation thereof was significantly affected by 0.10% phenol and completely inhibited by 0.20% phenol.

In contrast, the proliferation of *Corynebacterium glutamicum* was hardly affected by 0.16% phenol, which significantly affected the proliferation of *Escherichia coli*. Even in the presence of 0.20% phenol, which completely inhibited the proliferation of *Escherichia coli* and *Pseudomonas putida*, *Corynebacterium glutamicum* showed favorable growth. Further, *Corynebacterium glutamicum* was able to proliferate in the presence of 0.24% phenol.

Thus, it was shown that *Corynebacterium glutamicum* has a higher resistance to phenol as compared with *Escherichia coli* and *Pseudomonas putida*, and is highly suitable as a host in phenol production.

Industrial Applicability

According to the process of the present invention, phenol can be produced from 4-hydroxybenzoate with a practical efficiency using microorganisms.

The invention claimed is:

1. An isolated phenol-producing transformant constructed by transferring a gene which encodes an enzyme having 4-hydroxybenzoate decarboxylase activity into *Corynebacterium glutamicum* as a host, wherein the gene which encodes an enzyme having 4-hydroxybenzoate decarboxylase activity is the DNA consisting of the nucleotide sequence of SEQ ID NO:35.

2. The transformant of claim 1, wherein the *Corynebacterium glutamicum* as the host is a strain of *Corynebacterium glutamicum* in which a gene which encodes an enzyme having phenol 2-monooxygenase activity on the chromosome is disrupted or deleted.

3. The transformant of claim 1, wherein the *Corynebacterium glutamicum* as the host is a strain of *Corynebacterium glutamicum* in which a gene which encodes an enzyme having 4-hydroxybenzoate hydroxylase activity on the chromosome is disrupted or deleted.

4. The transformant of claim 1, wherein the *Corynebacterium glutamicum* as the host is *Corynebacterium glutamicum* R ATCC13032, or ATCC13869.

5. The transformant of claim 1, wherein the *Corynebacterium glutamicum* as the host is a strain of *Corynebacterium glutamicum* R ATCC13032, or ATCC13869 in which a gene which encodes an enzyme having phenol 2-monooxygenase activity on the chromosome is disrupted or deleted.

6. The transformant of claim 1, wherein the *Corynebacterium glutamicum* as the host is a strain of *Corynebacterium glutamicum* R ATCC13032, or ATCC13869 in which a gene which encodes an enzyme having 4-hydroxybenzoate hydroxylase activity on the chromosome is disrupted or deleted.

7. An isolated *Corynebacterium glutamicum* transformant PHE22-6.

8. A process for producing phenol, which comprises a step of allowing the transformant of claim 1 to react in a reaction mixture containing 4-hydroxybenzoate or a salt thereof under reducing conditions, and a step of collecting phenol from the reaction mixture.

9. The process of claim 8, wherein the transformant does not substantially proliferate in the reaction step.

10. The process of claim 8, wherein the oxidation-reduction potential of the reaction mixture under reducing conditions is -200 mV to -500 mV.

* * * * *

UNITED STATES PATENT AND TRADEMARK OFFICE
CERTIFICATE OF CORRECTION

PATENT NO. : 9,090,900 B2  
APPLICATION NO. : 13/884536  
DATED : July 28, 2015  
INVENTOR(S) : Hideaki Yukawa et al.

Page 1 of 1

It is certified that error appears in the above-identified patent and that said Letters Patent is hereby corrected as shown below:

On the Title Page:

At item (75), line 1, "Kizugawa (JP);" should be -- Kyoto (JP); --.

At item (75), line 2, "Kizugawa (JP)" should be -- Kyoto (JP) --.

Signed and Sealed this  
Thirty-first Day of May, 2016

Michelle K. Lee  
*Director of the United States Patent and Trademark Office*